(12) United States Patent
Morse et al.

(10) Patent No.: US 10,045,493 B2
(45) Date of Patent: Aug. 14, 2018

(54) STABILIZATION OF POLLEN PRODUCTION IN MAIZE

(71) Applicant: Monsanto Technology LLC, St. Louis, MO (US)

(72) Inventors: Jennifer Morse, St. Louis, MO (US); Michael S. Olsen, Minneapolis, MN (US); Chongqing Xie, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 78 days.

(21) Appl. No.: 14/812,240

(22) Filed: Jul. 29, 2015

(65) Prior Publication Data

US 2016/0050865 A1  Feb. 25, 2016

Related U.S. Application Data

(60) Provisional application No. 62/039,316, filed on Aug. 19, 2014, provisional application No. 62/101,298, filed on Jan. 8, 2015.

(51) Int. Cl.
| | | |
|---|---|---|
| *A01H 1/04* | (2006.01) | |
| *A01H 1/02* | (2006.01) | |
| *A01H 5/10* | (2018.01) | |
| *C12Q 1/68* | (2018.01) | |
| *C12Q 1/6895* | (2018.01) | |

(52) U.S. Cl.
CPC ............ *A01H 1/04* (2013.01); *A01H 5/10* (2013.01); *C12Q 1/6895* (2013.01); *A01H 1/02* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 7,321,087 B1 | 1/2008 | Carlson | |
| 7,705,220 B2 | 4/2010 | Holthaus | |
| 7,807,893 B2 | 10/2010 | Page | |
| 8,119,880 B2 | 2/2012 | Boerboom | |
| 8,410,257 B2 | 4/2013 | Jackson et al. | |
| 2008/0078003 A1* | 3/2008 | Zuo-Yu | A01H 1/04 800/275 |
| 2009/0031438 A1* | 1/2009 | Kennard | A01H 1/00 800/267 |
| 2010/0037342 A1* | 2/2010 | Johnson | A01H 1/02 800/263 |
| 2011/0105347 A1* | 5/2011 | Wu | C12Q 1/6895 506/9 |
| 2011/0154528 A1* | 6/2011 | Ragot | A01H 5/10 800/275 |

FOREIGN PATENT DOCUMENTS

| | | |
|---|---|---|
| WO | WO 01/90343 A2 | 11/2001 |
| WO | WO 2015/127248 | 8/2015 |
| WO | WO 2016/048686 | 3/2016 |

OTHER PUBLICATIONS

Arizona Genomics Institute, Maize Genomic Map, Chromosomes 2-3 and 5 (2008).*
Mickelson et al. Crop Science 42(6): 1902-1909 (2002).*
Upadyayula et al. Theoretical and Applied Genetics 113: 1395-1407 (2006a).*
Upadyayula et al. Theoretical and Applied Genetics 112: 592-606 (2006b).*
Puchta et al. Trends in Plant Science 1(10): 340-348 (1996).*
Arizona Genomics Institute B73 RefGen_v2 sequence, available at http://www.genome.arizona.edu/modules/publisher/item.php?itemid=16, accessed Nov. 11, 2016.
IBM2 2008 Neighbors Maize Genomic Map, available at http://www.maizegdb.org, accessed Nov. 11, 2016.
Upadyayula et al., "Quantitate trait loci analysis of phenotypic traits and principal components of maize tassel inflorescence architecture," *Theor Appl Genet*, 113:1395-1407, 2006.
Westerbergh et al., "Morphological traits defining species differences in wild relatives of maize are controlled by multiple quantitative trait loci," *Evolution*, 55:273-283, 2002.

* cited by examiner

*Primary Examiner* — David T Fox
(74) *Attorney, Agent, or Firm* — Dentons US LLP; Matthew Madsen, Esq.

(57) ABSTRACT

The present invention provides methods and compositions for producing elite lines of corn exhibiting reduced tassel skeletonization severity (TSS). Also provided in the present invention are corn plants exhibiting reduced TSS resulting from such methods, and methods for breeding corn such that the reduced tassel skeletonization traits may be transferred to a desired genetic background.

36 Claims, No Drawings

```
                    SEQUENCE LISTING

<160> NUMBER OF SEQ ID NOS: 297

<210> SEQ ID NO 1
<211> LENGTH: 878
<212> TYPE: DNA
<213> ORGANISM: Zea mays
<220> FEATURE:
<221> NAME/KEY: misc_feature
<222> LOCATION: (453)..(453)
<223> OTHER INFORMATION: n is a, c, g, or t

<400> SEQUENCE: 1
tatgttgtct attaaatgtt ctctttcaag tacatatttt aagtgatcat aaatgtttgt      60
agtgacaaca caaagtcact gaacaaagtt gtgctacatg ttaggtcttc tgctgttgtc     120
agagaagccc acagtcccat actaaggagc cgaacacggt ctcgagcaaa ggtattacac     180
tgtcatgata tggtttttgc ttgtgatgat cttatgtcct cttactgatg ctggtttgtt     240
gaaactggtg acatttaggc ggcttcaaca agtatcacat cagttcttta tctgaaagat     300
ggtgtctcca ttgctacttc tggagctgca gacaagtaag ttgcactttc atttttattc     360 tgcatttaa tttattaccc actttcatac ttttgtatgg tttgcaatag cttattgatt      420
ttatgatatt attgtgaaca taatgcactt gcntgacgat gagtgagcct gatatcatct     480
actctctgtt tcttgttttt ttttaaaatt ttgtagagta accaacgttt atatatttta     540
aatactaata ttgtaccttg taaattgtat gccagtgttg tgaaaatatg ggatacacga     600
aacctgaaag tgccgttctc caacaaaaac tctcaagcag gggcccaacc tttggtaaac     660
atctctactc actaaagaat gttaaactat cagtacaaaa agcaattgaa tcgtgcaatt     720
cagagtataa tcatgtctat caaattgagt caacaattat ggaatgttgt gtttccgtag     780
ctcaaatctg gacaatctct gaacaaacat actggtcttt tgtctctgaa ggaggggggtg    840 aaacatggca tctcttgcct gtctcaagat tcgtatgg                              878

<210> SEQ ID NO 2
<211> LENGTH: 485
```

```
<212> TYPE: DNA
<213> ORGANISM: Zea mays
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (53)..(202)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t

<400> SEQUENCE: 2
gatatccant angatatcca ttaggcttgt tcnggtagct ctcaatctat atnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnttgttact attttattgt acataacagt ttattattat     240
tctgacggaa cgtgcaacgt tccggaaacc cacaattata cagatgcatg cgattgccgt     300
ataaggaagc taaagaccaa agatatgttt gtcattaggt ctgcacatag tcatcntccc     360
taccagcggc tgagatgaaa gagacggcgg gctttggatc gctcttcacc actaaactca     420
gcacctcagg tcgcgagtag tggcccacca cgtcaaaatc aaacttggct cgaacaatct     480
ctcca                                                                  485

<210> SEQ ID NO 3
<211> LENGTH: 1690
<212> TYPE: DNA
<213> ORGANISM: Zea mays
<220> FEATURE:
<221> NAME/KEY: misc_feature
<222> LOCATION: (1493)..(1493)
<223> OTHER INFORMATION: n is a, c, g, or t

<400> SEQUENCE: 3
tttatattgg atttatacat cctcttgaag ttcttgtatc accgcaccta gagaattgtt      60
tacttcagtt atatggcatt atggaccatt tcatttagg agacttctga ttttatccat      120
gctttacata attacattac atatttcagg ctcttttgca ttcatcacat tgggttcctc     180
gagcccggcg ggcttttgca caccatggag ttaagttttc aagtctggaa gtggacctcc     240
cagccatgat ggctcagaaa gacaaagctg tggcaggact aacaaaggga attgaagggc     300
tctttaaaaa gaacaaggtg acttatgtta aaggctttgg aaaactgtca tccccctcag     360
aagtgtcagt tgatttgatt gatggtggta gcaccattgt caaaggaaaa aacataataa     420
ttgcaactgg gtctgatgta aaatcacttc caggaataac aattgatgag aagaaagttg     480
tttcatctac tggtgcactg tgcttgtcag agatcccgaa aaaactggtg gtaatcggag     540
caggttatat tggccttgag atgggttcag tctggaaccg ccttggttca gaggtcactg     600
ttgttgaatt tgccccggat atagtaccat caatggatgg cgaggtcagg aagcagttcc     660
aacgcatgct agaaaaacag aaattcaagt tcatgctcaa gacaaaggtt gttgggtgtg     720
```

| | |
|---|---|
| ataccagtgg agatggcgta aagctgacac tggagcctgc agctggtggt gagcagacca | 780 |
| tccttgaagc agatgttgtt cttgtctctg ctggcagaag cccatttact tctgggattg | 840 |
| ggcttgaaac tcttggtgtt gagacagaca aggctggcag gatccttgtt gataagcgct | 900 |
| tcatgaccaa tgtgaaggga gtctatgcaa tcggggatgc catccctggt cccatgcttg | 960 |
| cccataaagc tgaagaggat ggtgtcgcat gcgtagaatt cattgctgga aagaaggcc | 1020 |
| atgttgacta tggcacagtt cctggtgtgg tctatacaca tccagaagtt gcatctgttg | 1080 |
| gcaagactga ggagcaggtg aaggctctag gaattgccta taatgtgggg aagtttccac | 1140 |
| ttttggctaa cagtcgtgcg aaggccattg atgacgctga aggggtagtt aaggtgatcg | 1200 |
| cagagaagga aacagataag attctgggcg tgcacattat ggcacccaat gctggtgaga | 1260 |
| tcatccacga agctgtcgtc gccttgcagt atggagcatc cagtgaggac gttgctcgaa | 1320 |
| catgccacgc acaccctacc gtgagtgaag ccctcaagga ggcttgcttg caaaccttcg | 1380 |
| ataaagcaat ccacatataa tttctcattt tttgtgtcca aactccaaag tttgtggtaa | 1440 |
| ttttgggtct gttggaaaaa aggccctga ttgtccttt gttttgtcg gcnatactgt | 1500 |
| gaattgaccc tttgagttgt ccatcttagc ggggttttgt gcttccttgg cttggtttat | 1560 |
| ccatccaaat aataacctga tactatgttt tacattttat gcccatgaac cattgatgga | 1620 |
| tatacatttc taaggttcca gtaaccgcag tgttttgcga tgtttacatg tgactgttgc | 1680 |
| tgtgagggcc | 1690 |

<210> SEQ ID NO 4
<211> LENGTH: 1060
<212> TYPE: DNA
<213> ORGANISM: Zea mays
<220> FEATURE:
<221> NAME/KEY: misc_feature
<222> LOCATION: (770)..(770)
<223> OTHER INFORMATION: n is a, c, g, or t

<400> SEQUENCE: 4

| | |
|---|---|
| cagtagtatc ttgaacgtcg agccctcccg gcccgccgcc gcagtccaca aatccgcacc | 60 |
| caaagcaagc ccaacgaaac ccagacggca acgagacagt tgtcatctca ctccaccgca | 120 |
| ccgtccgcgc acggctcgcc ggccgtcact cacacaacca gcacgacacc atccgttcct | 180 |
| ggccttcctc ccgtgcaact accactcgcg tcaccgcgga aattaacccc gaaatccagc | 240 |
| gccttcggca cgagcacgac caggcctgcg caggagatgg ggcggagagg ggagccctac | 300 |
| tacgtcgagg cggtgccgcc ggtggacgtg aacaagaaca cagagtggtt catgtacccg | 360 |
| ggcgtctgga ccacctacat cctcatgctc ttcttcgcct ggcttctcgt cctctccgtc | 420 |
| tctggttgct ccccggggc agcctggacc gtcgtcaacc tcgcgcactt cgccatcact | 480 |
| taccacttct tccattggaa gaaaggaacc ccttttgctg ctgatgacca aggcatctac | 540 |
| agcagattga catggtggga gcaaattgac aatggtcagc agcttactcg gaacaggaag | 600 |
| tttttaactg tggtacctgt ggtgctgtat ctgattgcgt cgcacttgac cgactacaag | 660 |
| cagccgatgt ttttctcaa cacgattgca gttttcgtgc tggtcgtggc aaaattgccg | 720 |
| aacatgcaca aggtccgcat atttggaatc aatgcagaca tctgaggacn gctgcaagaa | 780 |
| gtacatggat gcgatgccat gatgttatga acaagcagtg tgtttctcaa actcgacaca | 840 |
| actgcctgta atatatgtac aggtttagaa agaactgtaa atgaatgata ctctaggata | 900 |
| caaggtttgc ctgcagactg ctctgtgttg ccgttgccgc tgctttcttt tgagtttcac | 960 |
| tgaaagtgga aaccataact tgggtaaatg taacgttcgg ttttcagctt cagcaagaca | 1020 |

```
ataatttacc agcaaaaatg tttcaaaaaa aaaaaaaaaa                              1060
```

<210> SEQ ID NO 5
<211> LENGTH: 483
<212> TYPE: DNA
<213> ORGANISM: Zea mays
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (220)..(220)
<223> OTHER INFORMATION: n is a, c, g, or t
<220> FEATURE:
<221> NAME/KEY: misc_feature
<222> LOCATION: (376)..(380)
<223> OTHER INFORMATION: n is a, c, g, or t
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t

<400> SEQUENCE: 5

```
caccgannnn ctgaggttcc tgtcgtcgaa gcaggccctg ttcgacctgg ccgtcttccg         60
gcagtactat caggtttaat taattaattg gcattgtgtt gcctgattca gcaactcgtg        120
cttcatgtgc tggaanaatc gtgagccttt ctctgttttt cctttttnct tttcccggta        180
ggaatcgctg aatgcccggt acaaccgatc aggtttcgan acccctggt tcgtcatcgg         240
ggtctcctac tccggcgctc tcagcgcctg gttcaggctc aagttccccc atttgacatg        300
tgggagcctc gcgagctcag gggtggttct tgcagtgtac aactacaccg actttgacaa        360
gcaggttgat agtccnnnnn gggcataggt ggagacggcg caaatnaatt ctntctgttt        420
gatgtacttc tacccaattc aggtctccat atgtgacagc ctttattatg taggttggag        480
agt                                                                     483
```

<210> SEQ ID NO 6
<211> LENGTH: 331
<212> TYPE: DNA
<213> ORGANISM: Zea mays
<220> FEATURE:
<221> NAME/KEY: misc_feature
<222> LOCATION: (237)..(237)
<223> OTHER INFORMATION: n is a, c, g, or t

<400> SEQUENCE: 6

```
ctggacacag ctgcctccac atcatccttt gtcactgtaa cctcctcttg ttcatgcccc         60
cattgtgtca ccccttgac tccaacctcc accccagttt tcagcacgtc caccaccagc        120
ctctcgttca caaactgctc tgcaaagtgt ggccatgtga tcatgggcac gcctgcacag        180
actccctcta atgtcgagtt ccacccacag tgtgtcatga aacctccaac agatctntgc        240
cacaggatca taacctgcgg cgcccagccc cttatgatca agcctctgtc cttcacccgt        300
```

```
tcttcaaacc catccgcgag ccattcctca a                                          331
```

<210> SEQ ID NO 7
<211> LENGTH: 312
<212> TYPE: DNA
<213> ORGANISM: Zea mays
<220> FEATURE:
<221> NAME/KEY: misc_feature
<222> LOCATION: (238)..(238)
<223> OTHER INFORMATION: n is a, c, g, or t

<400> SEQUENCE: 7

```
gtccagtgtc atgaagatca ccaagaagct cgaagggaag agtgcaagcg ccgcgcttgc           60
tgctaaacgg tcgggaaaaa cgaagcacaa aaagaacaaa taagtggggt acagggtag           120
tggcgaagct tcctactttg taggagccga ccagatgatt ttttttggaga aatttgctac         180
cattttttt ggtgggtagg ggtggatttc ggtctgtaca gttcgggaat tcagaacncc           240
gtagttcttg tcttttcgga taagttttgt attagaagct tgacactttg gtgtttgtat          300
tagactggat cg                                                              312
```

<210> SEQ ID NO 8
<211> LENGTH: 356
<212> TYPE: DNA
<213> ORGANISM: Zea mays
<220> FEATURE:
<221> NAME/KEY: misc_feature
<222> LOCATION: (49)..(49)
<223> OTHER INFORMATION: n is a, c, g, or t

<400> SEQUENCE: 8

```
catatataat aactactgta ggcagcggca tctcctgctg ggacgaagnt tcaagaagct           60
agctaagaga gaagggcata acgagataat aagcagcgcg cgaagatgca agactgggcg         120
ccggtgttcg tctcgctggt gctcttcatc ctgctgtcgc cgggcctgct gttccagatg         180
ccgggcaagt gccggatcat cgagttcggc aacttccaga ccagcgccat ctccatcctc         240
gtccacgcca tcctcttctt cgccctcgcc gccatcttcc tcgtcgccgt cggggtgcac         300
atgtacctcg gctcctaggc ggcggcgcgg ggcgccgtac cttctctccc tctcta             356
```

<210> SEQ ID NO 9
<211> LENGTH: 708
<212> TYPE: DNA
<213> ORGANISM: Zea mays
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (309)..(310)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (484)..(484)
<223> OTHER INFORMATION: n is a, c, g, or t
<220> FEATURE:
<221> NAME/KEY: misc_feature
<222> LOCATION: (565)..(566)
<223> OTHER INFORMATION: n is a, c, g, or t
<220> FEATURE:
<221> NAME/KEY: misc_feature
<222> LOCATION: (578)..(580)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (604)..(604)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (650)..(652)
<223> OTHER INFORMATION: n is a, c, g, or t
<220> FEATURE:
<221> NAME/KEY: misc_feature
<222> LOCATION: (659)..(662)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (668)..(682)
<223> OTHER INFORMATION: n is a, c, g, or t
<220> FEATURE:
<221> NAME/KEY: misc_feature
<222> LOCATION: (685)..(696)
<223> OTHER INFORMATION: n is a, c, g, or t
<220> FEATURE:
<221> NAME/KEY: misc_feature
<222> LOCATION: (698)..(699)
<223> OTHER INFORMATION: n is a, c, g, or t
<220> FEATURE:
<221> NAME/KEY: misc_feature
<222> LOCATION: (703)..(704)
<223> OTHER INFORMATION: n is a, c, g, or t

<400> SEQUENCE: 9
tctgatgaca gaagctgaaa gaaaactgaa ataaacagtg tctttacagg tggcaaatgt    60
gatggatcat ttctttaccc gtcattcagc ttctaacaca atcgctacag taaaagaacc   120
ttatcggttt gtctcatcgc ttttgaaaca attaagctcc cgtccactca aatgggtca   180 ttcgttgtgc nctagcgcct gccattctcc accaccgcca ccccacatca gattagantt   240

```
gcatctaatc tgtggtttgt gtctttaatc tcactttctg atggcgtagc agcctatcgt    300
ctaaaggann ttcatatttg aaacanagta aaaaatagaa tatgtagaac taaaaataaa    360
taaagntaga aaatataggg attgaaaaac aaggaaatt  ttanaggagt nagtgttagt    420
gtttggaaca cntgaatata agaatatgtn tattcctcta ttctagtgaa taaaggcttg    480
ctcntcattc tatcatgtat agaatatttt taaggaatga gaacttgatt aggtgtacaa    540
attttacttt ctctatatca cgaannaaaa cgagcctnnn actggaaaaa taaaacttaa    600
ntcnttcatt ctaaacanta catgatgtaa aagtagaaat tggatttttn nnaaatgtnn    660
nngnancnnn nnnnnnnnnn nnctnnnnnn nnnnnngnnc tannactc                 708
```

```
<210> SEQ ID NO 10
<211> LENGTH: 137
<212> TYPE: DNA
<213> ORGANISM: Zea mays
<220> FEATURE:
<221> NAME/KEY: misc_feature
<222> LOCATION: (66)..(66)
<223> OTHER INFORMATION: n is a, c, g, or t

<400> SEQUENCE: 10
ttttacaacc tcacatgtaa ccagagatgt aattttatgc aaccaatcta agacttgcta     60
gcctanacca taaaggcata gaccattctc aagatggact gaaaaaaaat ctaacctcaa    120
caactaatct cacttcc                                                   137
```

```
<210> SEQ ID NO 11
<211> LENGTH: 1475
<212> TYPE: DNA
<213> ORGANISM: Zea mays
<220> FEATURE:
<221> NAME/KEY: misc_feature
<222> LOCATION: (999)..(999)
<223> OTHER INFORMATION: n is a, c, g, or t

<400> SEQUENCE: 11
tccccttccg atggttaagg agatatgccg ccatgtgctc attggccttg attacctcca     60
ccgtacactt tctattattc acactgacct taaaccagag aacatattgc ttgtgtctac    120
cattgatccc acaaaggacc ctcggaaatc aggcgtaccc ctagttccgc cttcaatgag    180
gacagacgag ccacctccta aggtgcctgc acaatcagga aatggtggcc tcaccaagaa    240
ccagaagaag aagatccgga agaaagctaa acgtgcagtt gctgcaactt cagaaggaag    300
tagtgctgtg gcatctgcgg acacagatgg gtcagatgac cgaggagatc tgggtacaac    360
aaatgagggt agtcctagac aggatggagc taagaagcgg gtgacacgag ataggcgcgg    420
tagcaaaggg gccaagaaga tgatggcaat gaaggctgat ctaaaatgca agctggttga    480
ctttggaaac gcatgttgga catacaagca gttcacaaac gacattcaaa caaggcagta    540
cagatgtcct gaggttatac ttggttccaa gtattctaca tctgctgaca tgtggtcctt    600
tgcatgcatt tgctttgagc ttgccactgg ggatgtgcta ttcgatccac atagtggcga    660
taattttgac agagatgagg atcacctcgc gctgatgatg gagctgctag gaatgatgcc    720
tcgaaagatt gcgttgggtg tcggtattc  acgtgatttc ttcaatcggt atggggattt    780
gcggcacatc cgacgcttgc ggttctggcc tctcaacaag gtgctgatgg agaagtacga    840
gttcactgaa ataaatgcta atgggatggc agattttctt gtcccaatac ttgattttgt    900
tcctgagaag cgcccctacag ctgctcaatt gcttcagcat ccatggcttg atgttggtcc    960
cctccgacag caacctaaaa cacggccaga gtcagcacng agtccaggtg atggtgtttc   1020
```

-continued

```
agagaagcaa aagaaagaga aagaagaaag agaggcaatg gccgtagagt tagggaacat    1080
tgccatagat ggtgcttctt cttccaggat ggcaaatgac ccccaatcaa gcacaaataa    1140
aacaaccgct acctcttcta agaagtgagc tgcatttgat ttcatgagtt aagctgtaaa    1200
acttgttttc attcgagaat tgctccatga gtgggaaaca tatgtttttt tttaggtttg    1260
agatatgtta ggatagctac cgagggaaaa gaacagtagg ctaaatattt gttgtatggg    1320
gttgggtgga caaggttaga tttgtcgggg ttgcagtaac cctagcccct ttctttgaga    1380
acatattctt ttgtacaatt agaatccgcg atttgtttaa tggtagcatt gagcaactgg    1440
aaacccgaga cgagttttgc cttaaaaaaa aaaaa                               1475
```

<210> SEQ ID NO 12
<211> LENGTH: 772
<212> TYPE: DNA
<213> ORGANISM: Zea mays
<220> FEATURE:
<221> NAME/KEY: misc_feature
<222> LOCATION: (3)..(9)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (277)..(279)
<223> OTHER INFORMATION: n is a, c, g, or t
<220> FEATURE:
<221> NAME/KEY: misc_feature
<222> LOCATION: (295)..(296)
<223> OTHER INFORMATION: n is a, c, g, or t
<220> FEATURE:
<221> NAME/KEY: misc_feature
<222> LOCATION: (325)..(325)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (368)..(370)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (435)..(439)
<223> OTHER INFORMATION: n is a, c, g, or t
<220> FEATURE:
<221> NAME/KEY: misc_feature
<222> LOCATION: (451)..(453)
<223> OTHER INFORMATION: n is a, c, g, or t
<220> FEATURE:
<221> NAME/KEY: misc_feature
<222> LOCATION: (482)..(483)
<223> OTHER INFORMATION: n is a, c, g, or t
<220> FEATURE:
<221> NAME/KEY: misc_feature
<222> LOCATION: (545)..(546)
<223> OTHER INFORMATION: n is a, c, g, or t
<220> FEATURE:

```
<221> NAME/KEY: misc_feature
<222> LOCATION: (574)..(576)
<223> OTHER INFORMATION: n is a, c, g, or t
<220> FEATURE:
<221> NAME/KEY: misc_feature
<222> LOCATION: (614)..(658)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t
<220> FEATURE:
<221> NAME/KEY: misc_feature
<222> LOCATION: (663)..(665)
<223> OTHER INFORMATION: n is a, c, g, or t
<220> FEATURE:
<221> NAME/KEY: misc_feature
<222> LOCATION: (667)..(667)
<223> OTHER INFORMATION: n is a, c, g, or t
<220> FEATURE:
<221> NAME/KEY: misc_feature
<222> LOCATION: (671)..(674)
<223> OTHER INFORMATION: n is a, c, g, or t
<220> FEATURE:
<221> NAME/KEY: misc_feature
<222> LOCATION: (677)..(680)
<223> OTHER INFORMATION: n is a, c, g, or t
<220> FEATURE:
<221> NAME/KEY: misc_feature
<222> LOCATION: (682)..(684)
<223> OTHER INFORMATION: n is a, c, g, or t
<220> FEATURE:
<221> NAME/KEY: misc_feature
<222> LOCATION: (703)..(708)
<223> OTHER INFORMATION: n is a, c, g, or t
<220> FEATURE:
<221> NAME/KEY: misc_feature
<222> LOCATION: (711)..(713)
<223> OTHER INFORMATION: n is a, c, g, or t
<220> FEATURE:
<221> NAME/KEY: misc_feature
<222> LOCATION: (715)..(771)
<223> OTHER INFORMATION: n is a, c, g, or t

<400> SEQUENCE: 12
tannnnnnnt ggcttctagt acaagtaaga ttgcgactga tcgagaacaa aaggagcacg      60
tctttcttgc ctacttggtt tgggaactat tgtancaaca ctgggatcag gaatcagagg     120
aaacnccttc agtgtgaatc cctaccttgc gtgttggtca tgccagattc tgatgcaatc     180
atagggggag ttagttagat atgcattcag atgctagaat tagttgggta ctgaaattcc     240
atcantctag gattactcga aatgtctaga tctgacnnnt gacccttctc cttanngaa      300 agaaaaagac aggtaactgc ataancaaaa acttttactt taaggcgnac tggtttttgt     360
ttgcatannn actaaaaaaa cttttgtgat gctcctgttg agttggtcta acatccatcc     420
tgcttgcaac tantnnnnnt cactgaatag nnnggctgta ttatcctgtg atctaatatt     480
anntgaatag ttgaaaaacc tataaacaat gatatattgc catgtaagac ctcctatttg     540
tttgnntatc tttgtgttat gcactacata ttthnnntgaa aatgcgagca tgatgattct     600
tccataggtg ggtnnnnnnn nnnnnnnnnn nnnnnnnnnn nnnnnnnnnn nnnnnnnnaa     660
ntnnntntaa nnnngcnnnn gnnnacattc tcttgagctt acnnnnnnca nnntnnnnnn     720
nnnnnnnnnn nnnnnnnnnn nnnnnnnnnn nnnnnnnnnn nnnnnnnnnn nt             772

<210> SEQ ID NO 13
<211> LENGTH: 1183
<212> TYPE: DNA
<213> ORGANISM: Zea mays
<220> FEATURE:
<221> NAME/KEY: misc_feature
```

-continued

```
<222> LOCATION: (102)..(102)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (210)..(211)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (242)..(245)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (249)..(250)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t
<220> FEATURE:
<221> NAME/KEY: misc_feature
<222> LOCATION: (577)..(577)
<223> OTHER INFORMATION: n is a, c, g, or t
<220> FEATURE:
<221> NAME/KEY: misc_feature
<222> LOCATION: (579)..(582)
<223> OTHER INFORMATION: n is a, c, g, or t
<220> FEATURE:
<221> NAME/KEY: misc_feature
<222> LOCATION: (586)..(587)
<223> OTHER INFORMATION: n is a, c, g, or t
<220> FEATURE:
<221> NAME/KEY: misc_feature
<222> LOCATION: (615)..(619)
<223> OTHER INFORMATION: n is a, c, g, or t
<220> FEATURE:
<221> NAME/KEY: misc_feature
<222> LOCATION: (627)..(635)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (649)..(649)
<223> OTHER INFORMATION: n is a, c, g, or t
<220> FEATURE:
<221> NAME/KEY: misc_feature
<222> LOCATION: (712)..(715)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
```

<221> NAME/KEY: misc_feature
<222> LOCATION: (771)..(774)
<223> OTHER INFORMATION: n is a, c, g, or t
<220> FEATURE:
<221> NAME/KEY: misc_feature
<222> LOCATION: (787)..(788)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (837)..(841)
<223> OTHER INFORMATION: n is a, c, g, or t
<220> FEATURE:
<221> NAME/KEY: misc_feature
<222> LOCATION: (899)..(899)
<223> OTHER INFORMATION: n is a, c, g, or t
<220> FEATURE:
<221> NAME/KEY: misc_feature
<222> LOCATION: (925)..(925)
<223> OTHER INFORMATION: n is a, c, g, or t
<220> FEATURE:
<221> NAME/KEY: misc_feature
<222> LOCATION: (929)..(933)
<223> OTHER INFORMATION: n is a, c, g, or t
<220> FEATURE:
<221> NAME/KEY: misc_feature
<222> LOCATION: (1164)..(1166)
<223> OTHER INFORMATION: n is a, c, g, or t
<220> FEATURE:
<221> NAME/KEY: misc_feature
<222> LOCATION: (1174)..(1176)
<223> OTHER INFORMATION: n is a, c, g, or t

<400> SEQUENCE: 13

```
aaaggagtga cgggcacgtc ggcgtggcag gtggcgcggc gccattgggc ggggccgccg    60
atcgacgacc tgcgtgcgcg cgcggcggga gaggctgtta cnaaaacaga gaagctcaca   120
tcggccaagt ggtttcgcca tctccgccgc ccctggatca ctcggtgctc tcctctccta   180
ctctcccatt cagattctnt aanaaaaaan ngtctagatc tagcgagatc gtgntgtagt   240
annnntngnn ttgcttggcg catcgttgtt tgttaacatt acatgcttac tgttgcccgt   300
gtgcgtgtat caccantgta tccatccatc catgtttgtt tctgcatgaa acggtgcgtg   360
cgcgcgtgtt gtcccgggtg tagaaggctg ccgcgcgctc tggacgaagc aggctcatct   420
cgtgctccag tgcggcagtg caatgcaaaa actgcaaggc caacctgaag ccttgaaacc   480
atggggccgg caaggcggca aggcatcggc acgnccgaaa gttgatggat catgcgtctc   540
gcgtctcatg tgtattattc gcatggcgaa atcgccncnn nngtgnntat atataattat   600
ttatttacgc actgnnnnnc gaccgannnn nnnnncgtgc gtgtngncng gtagggggggg   660 tggcaaacgc tttggcgcgt ggtccggtgc tcggttgctt accagctaga gnnnnaaagg   720
tgagacgctg ttgttttag atgcatgcct tttgcgtgca gnggagagcg nnnnaaggat   780
agctagnnag anggccnctc cattgcctgt agtgcagggt gttcatggct gctggtnnnn   840
ntggtcatac agtatgatcg acgacggcga gacacattca tttggtagaa catacgccnc   900
ccgccccgat aagaaaaaaa aaaancgcnn nnntaggttg ccgagaatgc acgccttcag   960
gttgtactcc ctccgtttct ttttatttgt cactggatag tgtaattttg cactatccag  1020
cgacaaataa aaagaaacgg agggagtata aattattaat gctatatagg acatggagtt  1080
cagagttttt tatttcaaag aaaaaatcag agagataaag agagagagcg ctgctgatct  1140
```
gtatatagaa agtagctagg tcgnnncttc ctannnccta cta         1183

<210> SEQ ID NO 14
<211> LENGTH: 654
<212> TYPE: DNA
<213> ORGANISM: Zea mays
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (494)..(496)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (543)..(544)
<223> OTHER INFORMATION: n is a, c, g, or t
<220> FEATURE:
<221> NAME/KEY: misc_feature
<222> LOCATION: (552)..(553)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (569)..(572)
<223> OTHER INFORMATION: n is a, c, g, or t
<220> FEATURE:
<221> NAME/KEY: misc_feature
<222> LOCATION: (574)..(579)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (592)..(607)
<223> OTHER INFORMATION: n is a, c, g, or t
<220> FEATURE:
<221> NAME/KEY: misc_feature
<222> LOCATION: (610)..(615)
<223> OTHER INFORMATION: n is a, c, g, or t
<220> FEATURE:
<221> NAME/KEY: misc_feature
<222> LOCATION: (617)..(619)
<223> OTHER INFORMATION: n is a, c, g, or t
<220> FEATURE:
<221> NAME/KEY: misc_feature
<222> LOCATION: (628)..(629)
<223> OTHER INFORMATION: n is a, c, g, or t
<220> FEATURE:
<221> NAME/KEY: misc_feature
<222> LOCATION: (631)..(643)
<223> OTHER INFORMATION: n is a, c, g, or t
<220> FEATURE:
<221> NAME/KEY: misc_feature
<222> LOCATION: (646)..(646)

```
<223> OTHER INFORMATION: n is a, c, g, or t
<220> FEATURE:
<221> NAME/KEY: misc_feature
<222> LOCATION: (649)..(650)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t

<400> SEQUENCE: 14
aggtattttt tgggggcttt gttaatctca atcaatcaat agaggacaca ggcaaaaagc      60
aagtataagt tgtggtactt tgctttcaag gagagattct gtcagcttga gtttctcagc     120
catcttctcc aattcatctg taagctgcca tcaaaataca atctcataag aaataaaagg     180
gagtnatttg catccaggtt tctttttta ctaaaaaagt acatatagcc agtaattcag      240
aagcatattt ctttcaaagt gaagaaattt agaacccata tgagctggaa cacttcatcc     300
gtcatttcat ttttttaat gtgccattcc tcccatgacc caagtgcgga ggcacaaaag     360
aagtatattt caaaatcaag taaatttaac tatgtcttaa accctaacag tcactttaag    420
ttcttgacaa ccaaataata ctcaaaaaca tcactccatt aaacaaaatt caattataga    480
ttcagtctct cncnnnaaag caaccttgtg cgaccgngca aaaaaaccgn aacccgaaca    540
acnngaaaaa cnngaacgac aattanggnn nngnnnnnng atacccgnan tnnnnnnnnn    600
nnnnnnnatn nnnnntnnnt ctctcgcnnc nnnnnnnnnn nnnttnacnn anat         654

<210> SEQ ID NO 15
<211> LENGTH: 877
<212> TYPE: DNA
<213> ORGANISM: Zea mays
<220> FEATURE:
<221> NAME/KEY: misc_feature
<222> LOCATION: (237)..(237)
<223> OTHER INFORMATION: n is a, c, g, or t

<400> SEQUENCE: 15
gagtatgaac agctctattc catcttacta tcccactatt tgttttttc ttgcaaatga      60 cctgaagttg tcctgagaac aaagtgtaat ggaaaccaac attggtctga cattttaaac    120
aatatatctg tgttttttc ttagttattg tattgctgta ttatgtcgtt tactaaactt    180
gtatgcgcgt ggagtgggct agccattttg cggatctatc agttaatttt catgcantta    240
ctcttcagat cataattgcc ctgttctttt taccaaattt caggttggcc ctaccctgc     300 tcttattaag gctgaagtgc cctggtcagc ccgaagaggc aatctctcgg agaaagaaag    360
agtcttgaaa acggtgaaag ggtaatataa tgattttacc ttcctgatcg gttatttaag    420
cgtgttgatt gccttaaaac ttcctagttc cttgtttctc cattatgttt tgtttaattg    480
ctcttaatta tgcagtatac tgaacaaact tacaccagag aaattcgatc ttttaaaggg    540
tcaactaatg gaagctggaa ttactactgc tgatatattg aaggtatgtt ttatttacca    600
ccatctattt acagccttt ccctttgtt ttttgacgtc ttccctactg cttttgttca     660
ggatgttata tctctcatat ttgagaaggc agttttgag cccactttct gtccaatgta    720
tgctcaactt tgttctgatc tcaatgaaaa gcttccgaca ttcccttctg aagagccagg    780
tggcaaagag atcacattca agcgcgtgat attgaacaat tgtcaggaag cctttgaagg    840
tgctagcaac ttaagagctg agattgctaa attaact                             877

<210> SEQ ID NO 16
<211> LENGTH: 602
```

<212> TYPE: DNA
<213> ORGANISM: Zea mays
<220> FEATURE:
<221> NAME/KEY: misc_feature
<222> LOCATION: (216)..(217)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (440)..(449)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t

<400> SEQUENCE: 16

```
ccagcagacc aaatgtcaat cgctgtggta tactcagtgg caccaaatat gagctctgga      60
gccctatagt atcgggagca gatgtacgat atgtttggtt ccccccttgac cagaactttt    120 gcactgccaa agtcacatag tttaagctgg tgggtgtgtg ggttcacctg tagtgaagtt    180
tgaacatcaa tttcaaagta caaatcattt ctttannaaa agatacagta gcaaaatagc    240
agattttnca gcataccaga aggttttgtg gcttaatatc tctgtggcag acaccaatag    300
tgccatgaat gtaagccaat gccctacata tctgccaaaa nccaatataa tatcaaatat    360 tgaaaagaa ctagcacatt cattggagca gacaatattt aggngaaatg aaatatgntt     420
tnagtttcaa catcaaacan nnnnnnnnng ngcccaaaac ataagcttta aggtataatt    480
aaaacaacag canaaaggaa caggacaaac cattacctgg tacatataca gcttcacata    540
aataagtggc atgcgttggt tcatcttgtt gtgatgcttc acaactcgat gaactgtctc    600
tg                                                                    602
```

<210> SEQ ID NO 17
<211> LENGTH: 883
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (120)..(120)

```
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t
<220> FEATURE:
<221> NAME/KEY: misc_feature
<222> LOCATION: (744)..(745)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (819)..(820)
<223> OTHER INFORMATION: n is a, c, g, or t
<220> FEATURE:
<221> NAME/KEY: misc_feature
<222> LOCATION: (836)..(836)
<223> OTHER INFORMATION: n is a, c, g, or t
<220> FEATURE:
<221> NAME/KEY: misc_feature
<222> LOCATION: (849)..(850)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t
<220> FEATURE:
<221> NAME/KEY: misc_feature
<222> LOCATION: (872)..(878)
<223> OTHER INFORMATION: n is a, c, g, or t

<400> SEQUENCE: 17
```

```
aganaaaaag tagctataaa aaggacagtc aagtgacatt agctagaaat acagncattt      60
caattaaaac ttgcaccaga gtgcacttcc ataattacaa ccatgagcaa ttaagcaaan     120
gatctcanaa tatccacccc naaattangg tttcangctt gcangacctt ttacttgtct     180
ctgtgcaact aagaagtgac tacangttac cattcattaa acgcactgag agtcaatcag     240
accaaatgca acccaaactt acaaggtaac tatctaacct agctgtgagc cccagagcag     300
ttagtgacta gatgagcata gtancgctga cacaatttgt actgaaacna agacccgacg     360
tgatcatacc tgcggcaana ctgcagctgg tcgcagattg gcaaagaccc caagtccggc     420
acggagctgc agcagcccgg tctcaggctt gaggtgcttc tcattgttat cccacttata     480
gctacaacca cngaacatca tctaagtact catagtgcag gcgtgagagc gcaattccaa     540
ctaaaaggat gcaattcgct gcagtgccaa tattggggc tctgtgtctg ctgctgaaaa     600
tgacaataag tcaataacaa atccgctcac cctccaatgg cgccgaggag gacggcgtcg     660
gaacccttgg ccgcgtcgag tgtctcgtcg gggagcggcn cgccggtggc gtccagggcc     720
gagccaccca caagcttctc ctgnnaccgg agctcgacgc ctgcggcggg cgcaaggaag     780
caaacaaggg nggtcatgat cntgctacgt gctcgcgcnn aagagttcag ggagcnaagg     840
cagcgagcnn tggatgntga tgaagcagct tnnnnnnnag ggc                      883
```

```
<210> SEQ ID NO 18
<211> LENGTH: 475
<212> TYPE: DNA
<213> ORGANISM: Zea mays
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t

<400> SEQUENCE: 18
```

```
ggaaccaccc atctcctttt aagctcttca ataccgggc agccattatt ccaccaggaa      60
gcaagattcc ccaggcaaca acatcataa acccatgaac agccaggaca ggacgcaaat     120
cctgttctgc ctcagctgaa cctctcaaca acaaaacacg tataggccga ctgcttgtga     180
ctgaatgcat gttactgtct gtcagatcat ctcccgacca gcttgcaccc atggcccaga     240
caaccttaag tggtgtagtt ggatcgatga tgttcttgca ttctactttt ccggtacaag     300
aagggttaag agggcgagta aattcaaatg taataatgcc attttctgac ttacaccgaa     360
caaaagtgat gttctcngat gttgggtgaa tgcctgttgc actctttcca tcaatccaat     420
aagtttttac tcgcccaacc cnatcnttgc ccacccaagc aacataggtg aagct          475
```

```
<210> SEQ ID NO 19
<211> LENGTH: 2865
<212> TYPE: DNA
<213> ORGANISM: Zea mays
<220> FEATURE:
<221> NAME/KEY: misc_feature
<222> LOCATION: (1671)..(1671)
<223> OTHER INFORMATION: n is a, c, g, or t

<400> SEQUENCE: 19
```

```
gcacgagacc attacctacc cgccggccgg cgcggcagtt cgccaccatc gtgctccgta      60
cacgctccgc tccggccatg gccgccgccg cggcctcctt ttcggccctg ccgttccttc     120 tactttgct gctggtgccg tcgctcgacg gcgcctccaa tgtgacgtac gaccaccgct      180
ccctcatcat ctccgccgc cgccgcctcg tcatctccac ctccatccac tacccccgca     240
gcgtccccga gatgtggccc aagctggtgg ctgaagccaa ggacggcggc gccgactgca     300
tcgagaccta cgtcttctgg aacggccatg agatcgcccc aggccagtac tacttcgagg     360
accggtttga cctggtgcgg ttcgtgaagg tcgttagaga cgctgggctg ctcttgatcc     420
tgcgcatcgg gccctatgtc gccgccgagt ggaattatgg aggcgtgccg gtgtggttgc     480
actacgtgcc aggaacggtt tcaggacaa caacgagcc attcaagaac catatgaaga      540
gtttcacgac atacatcgtg gatatgatga agaaagagca gctcttcgct tctcagggag     600
ggaacattat cctagctcag atagagaacg aatatggaga ttattatgaa caagcgtatg     660
gagctggcgg caaaccatac gccatgtggg cagctagtat ggctcttgct caaaacactg     720
gtgtcccttg gattatgtgc caagagtctg atgcccctga tccgtgata aactcttgca      780 acggtttcta ctgcgatgga ttccagccaa attcgccaac caagccaaaa atttggactg     840
agaattggcc aggatggttc cagacttttg gtgaaagtaa tccccacaga ccacctgaag     900
atgttgcatt cgctgttgca cgttttttcg agaaaggtgg cagtgttcaa aattactatg     960
tgtatcatgg tggcacaaat tttggtcgca ctactggggg gccattcatt acaactagct    1020
acgactatga tgcaccaatt gatgaatatg gacttcggag atttccgaag tgggcacatc    1080
tgagggaact tcacaaatct ataagattgt gtgagcacac cctgctttat ggaaatacaa    1140 cgtttcttc tctgggtcct aaacaagagg ctgatattta cagtgatcag tctggaggct    1200
gtgttgcatt cctggcaaat attgattcag ccaatgacaa agttgtcact ttccgtaaca    1260
ggcaatatga tcttcctgct tggtcagtta gtattcttcc tgactgcagg aatgtggtgt    1320
tcaacactgc aaaggtgcaa tctcaaactt caatggtgac catggttcca gaaagtttgc    1380
aagcatcaaa acctgagcga tggagcattt tcagggagag aactgggatt tggggtaaaa    1440
atgactttgt ccggaatgga tttgtggacc atattaatac gacaaaggac tccaccgact    1500
acctatggta cacaacaagt tttagtgtgg atggaagtta ctcctcaaaa gggagccatg    1560
ctgtccttaa tatcgactcc aatggccatg tgtccatgc tttcttgaat aatgtgctca    1620
taggtagtgc atatggtaat ggctcacaat caagattcag tgtcaaattg nccatcaacc    1680
tgaggactgg aaagaatgaa cttgcccttc taagtatgac tgttggttta caaaatgcag    1740
gattcgctta tgaatggata ggagcaggct ttacaaatgt gaacatctct ggtgtgagaa    1800
ctggaatcat agacttgtct tcaaataatt gggcatacaa gattggactg aaggggaat    1860 attataattt gttcaagcct gatcagacaa ataaccaacg gtggatacca caatccgagc    1920
caccaaaaaa ccaaccttgt acatggtata aggtaaatgt tgatgttcca caaggagatg    1980
acccagttgg gatagacatg cagtctatgg ggaaaggctt ggcttggttg aatggaaatg    2040
ccatcgggcg gtattggccg aggaccagtt ctattaatga taggtgcact cccagttgta    2100
actacagggg aacatttatt ccagacaagt gcaggacagg ttgtggacag ccaactcaga    2160
gatggtacca tatcccacgg tcatggtttc atccctcagg gaacatcctc gtggtctttg    2220
aggagaaggg tggggatccc acgaagatca cattctcaag aagagctgtg acgagcgtgt    2280
gctcctttgt gtcagagcac ttcccttcca tagacttgga atcctgggat gaaagtgcca    2340
tgaacgaagg cacacccca gccaaagcac agctgtcttg ccccgagggt aaaagtatat    2400
```

```
cttccgtgaa gtttgcgagc ttgggaaacc ccagtggaac ctgtagatca taccaaatgg    2460
ggcgctgcca ccacccgaac tccttatctg ttgttgagaa ggcctgtctg aacaccaaca    2520
gctgtacagt ctccctgaca gacgagagct ttgggaagga tttatgccct ggagtcacca    2580
aaacactcgc catcgaagcg gactgttctt agtgacctac ggagtacgaa gtactcggtg    2640
tgcatctagg ttccactgca agtatgcccg tcaaaattct aaaattgtag tgcttgttgc    2700
acggcaatgc tattgtaacc tggatttgaa tgtatccatc tgagataggt tatgtttcag    2760
gagctttctt aaactaacgt tgttgctgag cagcatggat tgaaatagca ggctatggca    2820
aatgacggct aaaaaaaaaa aaaaaaaaaa aaaaaaaaaa aaaaa                    2865

<210> SEQ ID NO 20
<211> LENGTH: 379
<212> TYPE: DNA
<213> ORGANISM: Zea mays
<220> FEATURE:
<221> NAME/KEY: misc_feature
<222> LOCATION: (354)..(354)
<223> OTHER INFORMATION: n is a, c, g, or t

<400> SEQUENCE: 20
tcagcagttc aacagctttt aacagatcag tatatgttgg ttttggagga agtgattagg     60
aagaagaaac gatggaccac aatggtaagt gctcaccgtt cgtaaatata tgacaccgtt    120
gattttttta aaaaaaattt aatcactcgt tttattaaaa aataatgag ttatcattta     180 tttttatatg atttagtttg tgcttgactt aaaattttta cattttagaa taaatatttt    240
gaataagatg agtcgtcaaa gttttcaaaa aaatcaata gtgttatata tttatgaacg     300
gaggtagtac tcacttcgga ctgaattatt gtggaaagac catgaggatg tccngaaagt    360
cacagtcatg cttcagtat                                                 379

<210> SEQ ID NO 21
<211> LENGTH: 1139
<212> TYPE: DNA
<213> ORGANISM: Zea mays
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (276)..(278)
<223> OTHER INFORMATION: n is a, c, g, or t
<220> FEATURE:
<221> NAME/KEY: misc_feature
<222> LOCATION: (329)..(329)
```

```
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (616)..(616)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
<222> LOCATION: (692)..(692)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (786)..(787)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (844)..(844)
<223> OTHER INFORMATION: n is a, c, g, or t
<220> FEATURE:
<221> NAME/KEY: misc_feature
<222> LOCATION: (863)..(863)
<223> OTHER INFORMATION: n is a, c, g, or t
<220> FEATURE:
<221> NAME/KEY: misc_feature
<222> LOCATION: (896)..(898)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
```

<222> LOCATION: (916)..(916)
<223> OTHER INFORMATION: n is a, c, g, or t
<220> FEATURE:
<221> NAME/KEY: misc_feature
<222> LOCATION: (923)..(923)
<223> OTHER INFORMATION: n is a, c, g, or t
<220> FEATURE:
<221> NAME/KEY: misc_feature
<222> LOCATION: (938)..(942)
<223> OTHER INFORMATION: n is a, c, g, or t
<220> FEATURE:
<221> NAME/KEY: misc_feature
<222> LOCATION: (956)..(956)
<223> OTHER INFORMATION: n is a, c, g, or t
<220> FEATURE:
<221> NAME/KEY: misc_feature
<222> LOCATION: (961)..(961)
<223> OTHER INFORMATION: n is a, c, g, or t
<220> FEATURE:
<221> NAME/KEY: misc_feature
<222> LOCATION: (1137)..(1137)
<223> OTHER INFORMATION: n is a, c, g, or t

<400> SEQUENCE: 21

```
nnnnnnnncn nnnnntgccg angtgccaag tcgtgctcct gccttggtgt cctgcaccgg        60
cttggtgtct cctggacgct caggagattc tgtttcatcc gatgagacga tgtcgacttg       120
cgactccatg aaaagcccng actttgagta cgtagacaat caggacacnt cnatgctggc       180
ttcgttgcag cgacggacaa gtgaacatct gcgaatatca gaggatagag atgttgaagg       240
tctgctgaaa ttcatatacg atttgaattg tttaannngt gtgttttgtt atacttttg        300
ttgatccagt tgctttcttt tgcagaaant aagcggaaga aaaatgccgt ggccccaatg       360
gaaattgacc gcatctgtga tgttgacagt gaatatgagg atccacagct ntgcgctact       420
ctggcttctg acatttacat gcacttgcga gaggctgagg tgacacattc ttttctaatt       480
tctggtgacc aaatggtttc atntgagcac tgaacataag gaactttggg ttgactgcca       540
acgttgatgc aataagctag gctgcaatat gcttanatta agtctgttag atcgtactta       600
tgtaattgca gttcancagt gtggntgtaa tttctnattc ttntttatgt naagttttt       660
tngttggtgt attaatgaaa cttgatttga tngaaggact gtctatgttt tgttcaatgg       720
aactttggnc tacacttgaa attttctctt cttncttgat ttttactaat agtgctttac       780
ttnctnncag acgaagaaaa gaccgtcaac tgatttcatg gaaangattc aaaaagatgt       840
caanccaagc atgagagcaa ttntgataga ctggctcgtg gaagtaagtt tttttnnngt       900
ctnaaagtaa gaaaanccta aanaacaatc ttgtcaannn nnattcatta ttttcncctc       960
ntgcaggttg ctgaagaata tcgtcttgtt cctgatactt tgtacctgac agtcaactac      1020
attgaccgtt atctttctgg caacgaaatc agccgccaac ggctgcaatt acttggtgtt      1080
gcatgcatgc ttatagctgc gtaagattct gcttctcttt ccatttatta tccttantt      1139
```

<210> SEQ ID NO 22
<211> LENGTH: 508
<212> TYPE: DNA
<213> ORGANISM: Zea mays
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (464)..(477)
<223> OTHER INFORMATION: n is a, c, g, or t
<220> FEATURE:
<221> NAME/KEY: misc_feature
<222> LOCATION: (479)..(481)

<223> OTHER INFORMATION: n is a, c, g, or t
<220> FEATURE:
<221> NAME/KEY: misc_feature
<222> LOCATION: (492)..(496)
<223> OTHER INFORMATION: n is a, c, g, or t
<220> FEATURE:
<221> NAME/KEY: misc_feature
<222> LOCATION: (498)..(500)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t

<400> SEQUENCE: 22

```
gaacattctc ttgcagcaac agccatctca cgagcactaa catccttgga tggctcccac      60
agacttgcat ccttatggaa gagagtacca atcttctctc cttggagaac tctaacaatg     120
ctctgagatg caaatccact tcaagaataa aaaggaagtt aaaccaattc gctatccatc     180
atacagagac aaacatagat tacagcatat gaagtttact tggttctctc aaggtgacaa     240
ctgatgaaat gaacactgtt agacaagcat tactccatcc attttgcaat gtttgtccat     300
agcataccaa gcgcagagac tactgaagta ttgttccaag aaaaattcaa attaacatga     360
tacaactact cttcttcaa cacatctaat taggggagag tggaaacnta gcaataacta     420
cactcctgat atcctcaata gacaaacaat gtgcaacaca tttnnnnnnn nnnnnnnann     480
nacattgaaa annnnngnnn tntttgga                                       508
```

<210> SEQ ID NO 23
<211> LENGTH: 578
<212> TYPE: DNA
<213> ORGANISM: Zea mays
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (526)..(531)
<223> OTHER INFORMATION: n is a, c, g, or t
<220> FEATURE:
<221> NAME/KEY: misc_feature
<222> LOCATION: (540)..(541)
<223> OTHER INFORMATION: n is a, c, g, or t

```
<220> FEATURE:
<221> NAME/KEY: misc_feature
<222> LOCATION: (553)..(557)
<223> OTHER INFORMATION: n is a, c, g, or t
<220> FEATURE:
<221> NAME/KEY: misc_feature
<222> LOCATION: (560)..(562)
<223> OTHER INFORMATION: n is a, c, g, or t
<220> FEATURE:
<221> NAME/KEY: misc_feature
<222> LOCATION: (575)..(577)
<223> OTHER INFORMATION: n is a, c, g, or t

<400> SEQUENCE: 23
ctcatggagt gctgaagctc cagccncaca ccagaggctg ctggnattgg acacaacctc      60
cataatagcn tggatacacg accttgcagc atcgaacaca caagcattcc tgtgtttccg     120
taactcccaa gcatcagcgg aattctacaa aatattcaag attgtgctaa gctgtggggt     180
ttggctggag caaaagctct taaaaggctc tggccttaat ctaggnttta gttcccctgt     240
acttngaggt ttggtttttg tgtgtttagc tcagtttttt tnagtttctg ctgccattca     300
ttttggcggc ttgtacttgg tctattttag agctttctnt tcttaatata gtgatacaca     360
attctcctgc gtattcgaga agaaaaataa ctcccaagcg accaagatga tcaacaaatt     420
gagacaatga gacctttctt aaactccttt gaaactctct ttgacagtcc ggctccacca     480
accggagaaa ctattagtgt cagntagggg ggcagcagcc tgacannnnn nccctatgcn     540
naactgatgc ccnnnnntgn nnagagaaca tacannna                            578

<210> SEQ ID NO 24
<211> LENGTH: 595
<212> TYPE: DNA
<213> ORGANISM: Zea mays
<220> FEATURE:
<221> NAME/KEY: misc_feature
<222> LOCATION: (492)..(492)
<223> OTHER INFORMATION: n is a, c, g, or t

<400> SEQUENCE: 24
gcagcatcgt ccacatccca agggaataag agaacagcag gttggaaaca atagtgttgg      60
tgttactggg gcctgtatga ttttgtttaa actgtgtgca cgtttgtgtt ggcagtggag     120
gaggagagag cgaagctgtt tgaagggtca aacagtgcgg ataaaccgag aatgagaacg     180
cagcaggaga ttctaaccaa atataggttt ggcggggtaa gccatgaaca ttgcgttttc     240 ttttttttgat gtgtatcagt gtagagcatg gggtggggag ctaaatgtag taggtccatt     300
gcattgcagg acgccgccgc cgcagctgct catgcgaagg ataagctgat gcagaggcag     360
gagaaactgg aggtgcacat atggcttgta agcaattgct ttgggtgaga gcagtatgta     420
attctgtttg tttaatttgt ttaccagaga attagccaac aaaccgcgga gcttcagaat     480
ggagcggaga antttgcttc cctggcgcag gagctcgcga aaacaatgga gaacaagaag     540
tggtggaagc tataaactgg gtttgtttgt acgtatgtgt gttgttggat gacac          595

<210> SEQ ID NO 25
<211> LENGTH: 372
<212> TYPE: DNA
<213> ORGANISM: Zea mays
<220> FEATURE:
<221> NAME/KEY: misc_feature
<222> LOCATION: (108)..(108)
<223> OTHER INFORMATION: n is a, c, g, or t

<400> SEQUENCE: 25
```

```
tccttgactt catccttctt cttaccatcg cctgaaagca cccctctcca acttatctga      60
aaccatcaag ctaggattga tattgttgac atcgtgaact tggcattntc cctacagtgt     120
gggcgtgctt tcggctgatc cgctcacatg gtagttatgg gcagggtcgt ttgactgaca    180
ggttctcgcg tgtgatgatg tttgccttca tgttaacttt tgtaaaaaaa aaacattcat    240
tcatattatg tttctggctc ccttcgtcat caaaggggaa ttggtggtgg tggtggcttg    300
taaaatacac tcaaattttg tgcatggaca tgtcagaccc ttatcatgta tactagctga    360
tgtgatccgt tc                                                         372
```

<210> SEQ ID NO 26
<211> LENGTH: 1013
<212> TYPE: DNA
<213> ORGANISM: Zea mays
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (20)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (994)..(999)
<223> OTHER INFORMATION: n is a, c, g, or t
<220> FEATURE:
<221> NAME/KEY: misc_feature
<222> LOCATION: (1003)..(1003)
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t

<400> SEQUENCE: 26

```
nnnntgnnng agcctaagan nnntatantn agcatgatca gtgtgataga acaaattaag      60
```

```
caaaacagga tgaaaatgtt tactgtgcat atataaggaa caagcatgca tatatcactc      120
gtattatcta gcatctcata tggaaaagcnt ggggatgttc acagatctat atgagctcta      180
tagccctctt tacttcaggt ggcaatttca aagcattgag gctggcaact agcacgtggt      240
aattatgtat gttttgggca aacaagttca ntctatttcc tgtcgggtag gttcagtact      300
gaacgctaga tctgcaccaa atccaaccac cggccgctgc aactgccaaa agtagggtag      360
ctacctaagt tgtagatcta cagtggcaan ggggcgcgac gcttacgttg gggcagtgct      420
tggcgatggc agtgcacagc gccttaacga tgccggcgtt gatgttgaag aggtcgtccc      480
tggtcatgcc gggcttcctg ggcactcctg cggggatgat gacgatgtcg gagccctcca      540
gcgcctnccc gagctggtcg tccccatga accccttcac ctgcaggagc agaaaccagt      600
gagctcggat ccagtccagt tccgtccgag ccaagccaga ggagcgcgcc gagcagggag      660
gtaccagggc ggggnagttg atgtgggaga cgtcggccgc gacgccgggg gtgccggcga      720
tatcgtagag ggagagggag gaaacgagcg ggttgagctt catgaggagc gagagcggct      780
gcccgatgcc ncccgccgcg cccaggatgg ccaccttccg ctccggattg gccgaggacg      840
cgtagccgcg gctgcggcgg aggagctcgg ccgtggactt cagcagcgac ggcctcatgg      900
cggcggctgg gtcggggatc actcgctcgg gcgtgtctcg ctgtggattg gtgggggag      960 cggcagtggg cggcggcgag aagtgagggg agcnnnnnng ganaggatcn aaa           1013

<210> SEQ ID NO 27
<211> LENGTH: 359
<212> TYPE: DNA
<213> ORGANISM: Zea mays
<220> FEATURE:
<221> NAME/KEY: misc_feature
<222> LOCATION: (162)..(162)
<223> OTHER INFORMATION: n is a, c, g, or t

<400> SEQUENCE: 27
gcagctcaaa gcattcgtca agcaggatca acaagggacc ttgttattct tgttgatgac       60
accattagtg accaccaccg caaggggctg gaatctgctg ggtggaaggt tagaataata      120
cagaggatcc ggaatcccaa agcggaacgt gatgcctaca angaatggaa ctacagcaaa      180
ttccggctgt ggcagcttac agattacgac aaggtcattt tcattgatgc tgatctgctc      240
atcctgagga acattgattt cttgtttgca atgccggaaa tcaccgcaac tgggaacaat      300
gctacactct tcaactctgg ggtgatggtc attgagcctt caaactgcac gttccagtt      359

<210> SEQ ID NO 28
<211> LENGTH: 443
<212> TYPE: DNA
<213> ORGANISM: Zea mays
<220> FEATURE:
<221> NAME/KEY: misc_feature
<222> LOCATION: (393)..(393)
<223> OTHER INFORMATION: n is a, c, g, or t

<400> SEQUENCE: 28
cgtcggggat gaggtggttg ctcgagtcca ggcactcaac atcaggacga cggcggcggc       60
gacgaacagc tgcacggcaa gacgtatgt gtatgcacct gcaagccttg ctcccacctt      120
ttcattagtg aagatctcaa cctaacttaa ttatcgattg cgctgcgcag cgtcaagttc      180
gcaaccaaat gcttcatgga cgaagaggag ggctctgttg cgattgaagg cgaagcaatg      240
gctgtcctgc ctacactgga gctcagctct cagtcgacta gaaactagga gtggcctcaa      300
```

```
accgggtcac tagtcacaag ttgctgttgc ttaatcatac ccgacctggt aatccctctc    360
ttctgcaaca ctgtgtagaa tgcgtgtaaa ctnaacttag tgtagccttc acattataag    420
cgaggagtga aataaagctg ttg                                            443
```

```
<210> SEQ ID NO 29
<211> LENGTH: 773
<212> TYPE: DNA
<213> ORGANISM: Zea mays
<220> FEATURE:
<221> NAME/KEY: misc_feature
<222> LOCATION: (5)..(11)
<223> OTHER INFORMATION: n is a, c, g, or t
<220> FEATURE:
<221> NAME/KEY: misc_feature
<222> LOCATION: (392)..(392)
<223> OTHER INFORMATION: n is a, c, g, or t
<220> FEATURE:
<221> NAME/KEY: misc_feature
<222> LOCATION: (443)..(444)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (676)..(686)
<223> OTHER INFORMATION: n is a, c, g, or t
<220> FEATURE:
<221> NAME/KEY: misc_feature
<222> LOCATION: (688)..(699)
<223> OTHER INFORMATION: n is a, c, g, or t
<220> FEATURE:
<221> NAME/KEY: misc_feature
<222> LOCATION: (701)..(705)
<223> OTHER INFORMATION: n is a, c, g, or t
<220> FEATURE:
<221> NAME/KEY: misc_feature
<222> LOCATION: (709)..(712)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (729)..(731)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (737)..(737)
<223> OTHER INFORMATION: n is a, c, g, or t
<220> FEATURE:
<221> NAME/KEY: misc_feature
<222> LOCATION: (739)..(752)
<223> OTHER INFORMATION: n is a, c, g, or t
<220> FEATURE:
<221> NAME/KEY: misc_feature
<222> LOCATION: (754)..(760)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (769)..(770)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t
```

<400> SEQUENCE: 29

```
gcctnnnnnn ntctagagaa acataacacg tatgtatggg agagggagac gcctcaaaag      60
ttactaaaac taagttgtac agagcatcta acatgagatc tttaagcttt tgaaattgtg     120
agaataacac tggattttgc tggtggtact tatggcactt agatatattc tttactcctg     180
tcgttacatg agtactgctt ttgtctttga ataatttcc aaaatatata acaaaattag     240
ttttagccaa tctctgttgc aagatttatc ataatgcaat attaacttga ttcactgtaa     300
gtttcttagc tacattaaat ttgtatcatc tgtcaaacac atcaagtgct ggaggtattc     360
attttccctt tagacaaaac ttgtcaaaca cnttggtttt gcttggacaa atattgagg     420
acatatatac tttatttttt ttnncagtat caacgaagga tttcctggaa aggcctctag     480
caggttctca agtacagtta tgcttgctgg aaacaaatac gctcaacagt tggtctcgta     540
ttgatcctgg tacattccgg gtccgtggag caaactattt taggtaaatg tcattcttgc     600
agtatcaggt catacccatc atttatttat ttgaaactcc tggatgcttt atgggagtga     660
tcttagtntt gaatgnnnnn nnnnnngnnn nnnnnnnnng nnnnngctnn nnantatgct     720
gcatattann nanttgnann nnnnnnnnnn nnannnnnnn anaaactcnn tna            773
```

<210> SEQ ID NO 30
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 30

```
atctctttgt ggcttgtcca tcgctccaac ttagagcgac cccttctaga atcctcgtgg      60
ttttcgtcat ctgatatggc atcttcttcc acttcattca ncaatgaatt atctggctga     120
ggattctggc ccttcttgga taatgctgca tgacctctac tactctcttg ttcattcact     180
tcttttgttt caacctatat a                                              201
```

<210> SEQ ID NO 31
<211> LENGTH: 201
<212> TYPE: DNA
<213> ORGANISM: Zea mays
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t

<400> SEQUENCE: 31

```
tgataatata aggtttcaag catgacaact aaaaaaaagg aggaaanaga tgctcaccag      60
tccagtccat cccgtacacc ttgatgccga tatcattcaa ncgcctcgct aaatgatcgt     120
acctcccact gccacaccaa tcaaaggaag gtcagtgtca gccatccgca tgacaacaaa     180
ccagcatagc cagaaaantt c                                              201
```

<210> SEQ ID NO 32

```
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 32
tcctgaagca caatgaaatg caagtttcaa tgctaatatc ataaggagag atttactaat      60
atctgctcat gttatagggt ggatttactg aatgatgccc ntctgaagag cacaaacctg     120
atttctttca tataacatgt ggttcttagt gaaatatttg aaggtgtccc gtccctgtgc     180
aagcatagct tgttctatgg c                                                201

<210> SEQ ID NO 33
<211> LENGTH: 201
<212> TYPE: DNA
<213> ORGANISM: Zea mays
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 33
tctctagncc ttngtttcta tcacctattg ctccntaaaa cagcatcaca tggcaancat      60
tcagccacca cagcttgcaa gtatctccca ccagcacaag ngtgttacaa gacccagtgc     120
ttccaggcca cctgcacttc aaacaaaatc aacttgcagc aggggcactc cagcttcaaa     180
atgcagctca ttccgaaccc a                                                201

<210> SEQ ID NO 34
<211> LENGTH: 201
<212> TYPE: DNA
<213> ORGANISM: Zea mays
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
```

```
<220> FEATURE:
<221> NAME/KEY: misc_feature
<222> LOCATION: (200)..(200)
<223> OTHER INFORMATION: n is a, c, g, or t

<400> SEQUENCE: 34
gggggggggg catagaactc acaggttttnc tgtgcacata gtttgacgag cccacatggg      60
caagatctcc aaacagccac taaaaattat caaataatgt ntgcctatgt gcccattccc     120
acaagangtt gatctacaan gattctatct tttgccatgt ccaacaactt ctcccagaaa     180
catggatant agtttattcn t                                                201

<210> SEQ ID NO 35
<211> LENGTH: 201
<212> TYPE: DNA
<213> ORGANISM: Zea mays
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 35
cgggctngct atgtggagat atcggtcata tttcactatg gcccgacaac cgtgtagcaa      60
agggtctgac aaacttttg ggctcattga tgtagtgagc ngagccgaga tggctcattc     120
cgactcgcga gcaggctcat gagttgttat aaattaacca atccgtagaa taataatgga     180
tattggatag tttcgtagat n                                                201

<210> SEQ ID NO 36
<211> LENGTH: 344
<212> TYPE: DNA
<213> ORGANISM: Zea mays
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t

<400> SEQUENCE: 36
gctcaatatc aggataatgg cagttggtct ttacaaataa tgcgatgcca tanaactgcg      60
caaatcattg ataccatcgc atcagtaagg ggtgtggtaa cagcctagca tcattgtaca     120
agtctttccg aagcccanag acattcagac caganacgta aaccacgaac ctttctttac     180
ttaggatgac aatcttagct ggtcacaaaa tggtagctgg aatccacaaa gctctcaacg     240
tcccagagga atgatccgaa agtaacagcc tccaggacca gccttctcag cccggcaaag     300
cttatcctaa tgtgctcatc cttggatgaa ccaaccgtgc ctcc                      344

<210> SEQ ID NO 37
<211> LENGTH: 201
<212> TYPE: DNA
```

```
<213> ORGANISM: Zea mays
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 37
agagatggtg agagacngtt accggattaa cggaggaaac gcggtgagga ggcgaggtgc     60
ggtgagctca ggcaggcaga gaagagcaga ggaagagaga ncggtggagg cgatgattct    120
gtagggttgg gagagggtgg tatataaagc ccggcgcggg ggtggcgctg gcgctgcgcg    180
agcggaggag cgcgctcggc g                                              201

<210> SEQ ID NO 38
<211> LENGTH: 398
<212> TYPE: DNA
<213> ORGANISM: Zea mays
<220> FEATURE:
<221> NAME/KEY: misc_feature
<222> LOCATION: (250)..(250)
<223> OTHER INFORMATION: n is a, c, g, or t

<400> SEQUENCE: 38
gtcagacacc tacctgtcag gcatgaactg aaaaaggtgc aaaagaattg tcacttaact     60
tcaggtaccg ttagtgtctc atccagaaat tggtccagcg gccattagcg cgccactgca    120
ggatatgcag agaaacaatg gtggcaccgg agcaccatct gcaatgccga cacagcgtgt    180
atggtgccag acattgcatg catcgcatgc caccatgcgc tccccatcgt cgtcctgtgc    240
accacaaacn cactgcacct cccacgcatc tgcacctccc tggcaccgca gcccagtctc    300
catgtcagct ccgtggccgt gcacaccaat ggtgtcacca gactctgctc caccaagcat    360
caccggatcc catttatccc cagtaatgcc atccagtg                            398

<210> SEQ ID NO 39
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (166)..(168)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t

<400> SEQUENCE: 39
accttatatg ctgacaatgc tgtagctact tgaagtaatc tttcttgaat atccgaaacc     60
ttgccaagac tagattgtca agccaaaaac ataactcgca natcttggaa aatgattagc    120
aagcacccct agttganaat ttttttttat cgccagaagc tggcannntg gctagataca    180
ggaaccanat gagcatggcc g                                              201
```

-continued

```
<210> SEQ ID NO 40
<211> LENGTH: 201
<212> TYPE: DNA
<213> ORGANISM: Zea mays
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t

<400> SEQUENCE: 40
agtgaaagtg antaactcgc tcctaaagcc aaacaataaa tatgaangat gtaggttgtt      60
catttattta tgttcttgag cctaattgaa gcagactaac ntttctgttt ttaacatgtt     120
ctgaatatta tttttgggca aaagcaatca tcatcaaata caacntgcca actctaaaat    180
ttgccatttt cacatgtaga a                                               201

<210> SEQ ID NO 41
<211> LENGTH: 201
<212> TYPE: DNA
<213> ORGANISM: Zea mays
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 41
taccatcttt cctctaaaat gactctttag ttgtgaatga tgtattatat ggtagaatna      60
gctaattatn ncnaatgtat tttgcctgat gcatgtgcac ncccttatta tacttgggca    120
ttggcattgc ccttggttgt gacttgtgac ttacttctgg ctggaacctt ccataagaga    180
tactttaggt gctcactaag a                                               201

<210> SEQ ID NO 42
<211> LENGTH: 201
<212> TYPE: DNA
<213> ORGANISM: Zea mays
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (101)..(101)
```

<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t

<400> SEQUENCE: 42

```
ggttataggc agcttgttcc atgatgtatt atgtttatgt ggtgccattt tacttncatg      60
ctatgttact ntgcaaataa ataggaaata aaaatgatga nttacatttt agtctaatct     120
atgtactgct ttatttcgca actccaggtc tccacgttat gttgctgctg atatcaancc     180
atttgcccca cagatcattc a                                               201
```

<210> SEQ ID NO 43
<211> LENGTH: 201
<212> TYPE: DNA
<213> ORGANISM: Zea mays
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 43

```
aacgattaca cagtaagtaa ttagcaattc agcacgcctg cacntatttt ttcctacaaa      60
attaattaca ccatggatta gcttgatgaa acgagaggtc ntacagtact atccagtcag     120
gttgttccga attcaacaga gggagggagt caacaaaggc cctccattcg ggaatgaacg     180
tggcttgatt tgttaatggc g                                               201
```

<210> SEQ ID NO 44
<211> LENGTH: 201
<212> TYPE: DNA
<213> ORGANISM: Zea mays
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 44

```
ggagaagctn gtggttagaa tntgggtgtt tggatatnna nattctgata ttgtagattc      60
tgagtgaaan aatggaaaca gggaaagaca caataatcaa nacctcatta tcaacacctc     120
gttatgtaga taagctcgcc atacaaaaat ctaaattatt ccataattcc taaaataacg     180
ctgcatgcaa caaatatcgt a                                               201
```

<210> SEQ ID NO 45
<211> LENGTH: 201
<212> TYPE: DNA
<213> ORGANISM: Zea mays
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t

<400> SEQUENCE: 45

```
tgcatgtana acggtgnacg tgaccggaat gtccttgttc atatacgggg acggggctgc    60
accttccagt gaagttaaat agctccctcg gttaaatagc ntgcagttca gttcatcgga   120
gtattttaag aaaanaatta ttgtgtnatt gaacntnccg tgcaatcntc ntataattaa   180
acaacnaaaa nttataaaac a                                             201
```

<210> SEQ ID NO 46
<211> LENGTH: 201
<212> TYPE: DNA
<213> ORGANISM: Zea mays
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

```
<400> SEQUENCE: 46
gcccntggaa atgnagaaat ctgcagttta gtattcgcag ccattgcagg catcatcgat        60
tgctaaccct ggcgcgaaat ttgacaggaa gcatgcccaa ngaacctgaa gattggatct       120
agtgatctaa tcgcctctta tcaagacggg gctgtcaatt cgagttaatg acaagcatag       180
taacttgtac tagcagtaga g                                                 201

<210> SEQ ID NO 47
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 47
cctcaatttg atcaaaggtg ctcttgaagt taagttgaca gcagttgctt cgataaagtt        60
gctttgtgag tctgcggtcc tgttggatgc tgcagcagcc nagttatggg gtaaattact       120
tgacagtatt gtcacactat tgtccagaat gaatcaagat ggatcacaac aagagcataa       180
tgatggtact gatgcagtgg a                                                 201

<210> SEQ ID NO 48
<211> LENGTH: 844
<212> TYPE: DNA
<213> ORGANISM: Zea mays
<220> FEATURE:
<221> NAME/KEY: misc_feature
<222> LOCATION: (591)..(591)
<223> OTHER INFORMATION: n is a, c, g, or t

<400> SEQUENCE: 48
cccggtttaa aagttgggta cctcgaggcc ggccgggact tctagagttt agctatagcc        60
tcactgctag agcgccgcca tggctcaggt aaggggcagt gctcgtggca ctggcagtgg       120
cagcagcgcc gccgcgctgg cgctggtcct cctgtgcgcg ctcctccgcg gcgagttcgc       180
cgagtcggcg gtgtacacgg tcggcgaccg cggcgggtgg agcttcaaca ccgccagctg       240
gcccaacggc aagcgtttcc gcgccggcga cgtcctcgtg ttcaggtacg acgccagggc       300
gcacaacgtg gtgcccgtga gcgcggcggg gtacagctcg tgcagcgcgc ccgagggcgc       360
cagggcgctc gccaccggga acgaccgcgt cacgctgagg cgcggcgcca actacttcat       420
ctgcagcttc ccaggccact gccaggccgg catgaaggtc gccgtcaccg ccgcctaggc       480
actgcagggc ggccaatcag ccggcggaga gcgccgcgct cacggagtag taaagcacgt       540
agctaattag acggtgctgc ccttgttgtt caataatatc gtctgtcgtc ncgtacttca       600
taacctgcgc ggcgtgttag tagttgtttg gtggtgtttg gcgactggca ctataaagaa       660
gggtcagatc gagtgatgta cttgctacca ataaaggtat acgggtttgt gtgttcaaaa       720
aaaaaaaaaa aaaagcggcc ctattccaaa cctatagaga gctaatggct aattaaagtg       780
taagcggccg ttgagaaagt atattaaata attagctagc ctaaaaaaaa aaaaaaaagc       840
gggc                                                                    844

<210> SEQ ID NO 49
<211> LENGTH: 950
<212> TYPE: DNA
<213> ORGANISM: Zea mays
<220> FEATURE:
<221> NAME/KEY: misc_feature
```

```
<222> LOCATION: (650)..(650)
<223> OTHER INFORMATION: n is a, c, g, or t

<400> SEQUENCE: 49
cgtcactccc tcccccagac gcgtctgggg atagcaactc ccatgactac aatgggatta      60
actcctctgc tccctgtttg tttccggatg gttccaatgg cgaggatatg ttttaccttg     120
agcaagaacc tgggcacctg ggcgaccatg aaggtgctgc tccggtagca gatagcagat     180
tcggtgttat tgtgcaggag cagggtgtta ttgtgcatga gcagggtgag gccgtgggta     240
ctctcccaaa tgggaacaat ggaattggca atgagatgaa tgtggagtgt aaaatggtgg     300
tgccgtgcag caacgagcat cgaatggcga atgctgtcct agatgtgttt gaggaatgcc     360
tgagggaggc aaagagtaat ggggttatca atggtggcaa tgtggacggg agtggtgagg     420
aaagcgagct ctccaagcgg tggagagcgc agaggatgga tgagcttgat gtcttaagcc     480
ggaggctgag gttgctggtt gagtatgctg cggcggctgg gcagtgaagc agagattttg     540
gtggttttgg tgatgttcct gccacccttt tccccttttg tatagaagct aggttcctgt     600
gctatgcttt ggaatgtatt cctcagctgg acccttgcct ttagaaagcn tactatattt     660
aactatgtac ccttgagttt aataactcga gcagcataat aatctataat tttaacgctg     720
ttatttgcat gggttcctgc tgtttgatat agatgatagc cttgttaatg tagcttcagg     780
ctttcaaatt tcctctttt caattagaag ctgttgtact tgtaacttgt aagctgtgag     840
agagtaatat tatgtttcct tgttaaccgc ttgtaatgct tctcttatag cttcactaca     900
acgtctacat tcagcctgca atacccatga tttatttgca agcgcttcct               950

<210> SEQ ID NO 50
<211> LENGTH: 499
<212> TYPE: DNA
<213> ORGANISM: Zea mays
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t

<400> SEQUENCE: 50
caaaagatga ggggagtttt agaacataat agcacacaaa atggcacnac cntggtatga      60
tagtattaag aaaaagtgta gaatgatcat acaaagaagt atcataaana ttggttttga     120
ggatactgtc atcatctaca atgaggattt acacatcaag atatcgccca tggattttaa     180
```

| | |
|---|---|
| gttgacttga aacagttttg gttatgtact tcaccatcta agattttgc atcatctatg | 240 |
| gacattaggt cgaaaattct ctaaatacta gacacggttg tacacatact tccaacacng | 300 |
| atgaaacttg gttcaaacct ataaacatat actgtaacct tacaagaaaa tataattgag | 360 |
| tnaaagtgtg aagttcagta taanacctaa caatgctatg caagaatgct tcagtattga | 420 |
| aattatataa gatgacatgg aaacagcttg tgttgttgat gaaaagttcc aatgngtcaa | 480 |
| tttgttaggg tgcatttca | 499 |

<210> SEQ ID NO 51
<211> LENGTH: 917
<212> TYPE: DNA
<213> ORGANISM: Zea mays
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t

<400> SEQUENCE: 51

| | |
|---|---|
| cggaaatgac gagctattgc taacgaggat ttcttcgttg ccatgcgtac aaagaaccct | 60 |
| taaaccctaa tcctcccccg ctacacgttc gcttgatctt tacggccgcc gctactcgtt | 120 |
| cgccatggct gcctgctcct ccaggctcct anacctcact ctgagctcct ctttcctccg | 180 |
| ctcctgccgc ctcgcgtcca gctccctact tcccaccgcc tcccgctgcc acccggggtc | 240 |
| gctccactcc ctccgcttct gctctgctgt ccccgagttt gtcgatgtcg ccgccgaccc | 300 |
| tgccgaggcg gctgtatcct ccggacaccc gtggccggag tggggcaact tccttgataa | 360 |
| gctgcgggcc aagggtact tcgagcaagg tttgccctcc agcgtgagtt ctggcgaggg | 420 |
| agccgccgga gatggggatc cagcaactgc atctgagaac gcagcaacgg ctgcttccgg | 480 |
| taatacggtg gtggatgcgg aggatagcgc ggtgacctcg gaagatatct atcattttct | 540 |
| caaggacgag aacagggtga agaatgcgtg cctcaaattt gggcgagacc gcttcgatct | 600 |
| cctcagcttg cttcccaagc aggatattca agctattgtt atgtctggct gtcctaataa | 660 |
| caatcggaag cccgtctatt ctgcaaaaag gttgagagag tacgtgcagg tcaaagaaga | 720 |
| agatgcatgc agcatttgca aatttaaggc atcttgtgat agagcttatg tcactccaaa | 780 |
| gggtgaggtt gaagttagga ctgttgatgt tgttcgtata ctgttaagtt atgcaatgga | 840 |
| taaaaaccat tcangagata actctgttat cgaagaagtg tgcaagaatc tgcaaaaagc | 900 |
| ttctctcaaa gcttact | 917 |

<210> SEQ ID NO 52
<211> LENGTH: 201
<212> TYPE: DNA
<213> ORGANISM: Zea mays
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 52

```
ccttncctga gccatggcgg cgctctagca gtgaggctat agctaaactc tagnagtgag      60
ctgtagagcg caccaagaac cgctttttat aggcgaaccc nagtacccct gcacacgacg     120
ataaccaaac tctcgtttct agcgtatata gtggccatgg cacggtcaaa tggcccaggg     180
acaagcaagc gcttacgccg t                                               201
```

<210> SEQ ID NO 53
<211> LENGTH: 201
<212> TYPE: DNA
<213> ORGANISM: Zea mays
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t

<400> SEQUENCE: 53

```
ancatttttt tttgcacagc acaacaactc agcangatga aatcattctg gatgctggta      60
atcagaggct aacgcacatg ctttaggcca agttccatat nacagtagaa aaagaggctc     120
tctgggtttt gatctataga atctttgnac aggatcgttg ctgagattgc tattganttg     180
tttgctttgt acccttaagc g                                               201
```

<210> SEQ ID NO 54
<211> LENGTH: 201
<212> TYPE: DNA
<213> ORGANISM: Zea mays
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t

<400> SEQUENCE: 54

```
ataagaancc ttaatcttgg agacagnaac ttactggaac aacatgacaa gttccaagtt      60
```

```
cacatgaaac aacgtctccg ttacagtttc caagtttctg nttgtacttg taagtaaaca    120
tataaaacca ntattatgtn gcactgcaga caccatgaaa tngttatatt acagttaata    180
tcttgcacga caaacaccat t                                              201

<210> SEQ ID NO 55
<211> LENGTH: 201
<212> TYPE: DNA
<213> ORGANISM: Zea mays
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (173)..(174)
<223> OTHER INFORMATION: n is a, c, g, or t

<400> SEQUENCE: 55
caacaagtaa aatgaaccat ttttcttagt agagaanaat cattctgtca ccatccatgt    60 cgaaanaaa attaaaaaaa aaacccagca aaatatcaat nctagttgta gcaccttacc     120
ttcagtccgt gtaaagatgt aggtaatgag gcgaaagctc cccagagttc ctnncgcgct   180
gctcgatcct tcttaggtcc c                                              201

<210> SEQ ID NO 56
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 56
tggaaggggg gatactctga taaccatatt tagaaaagtt gcccgttttt ttcttccttg    60
gccacacaga agaatactgt gttattacag taagaagaga ntttgttaca actagttatt   120
ctttatatta tattcacgcc ttttacacat taaacaccac cacagcctat catcgagatg   180
ctaatagatc tagcaacatt t                                              201

<210> SEQ ID NO 57
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 57
gctattttct tttgcttcca tcactcttca ctggacattc ttcatttacc tcatgtttta    60
tgggtgattt ggataaacat gagtatatcc ttcaggtttg natcttgtct tagaaacaag   120
gacagagtca tcctagtgag gtaaaacatg atgcatattt attgcttcta ttagtatttt   180
taaatatgtg aactgggttg t                                              201
```

```
<210> SEQ ID NO 58
<211> LENGTH: 201
<212> TYPE: DNA
<213> ORGANISM: Zea mays
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (55)..(57)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 58
ctagaggatt tacaggaaaa gaatttagga gnnaaaaaag aaatatanaa aaaannnagt      60
gaagcccact ctatccgtat ccggcagcaa agctggcatc ngcatgtttt caggataaat     120
gaattctttt aaaagcttgc acagggccat gattgccgcc acaacccaca agcacacccc     180
catggacccg ggcagctcac n                                               201

<210> SEQ ID NO 59
<211> LENGTH: 201
<212> TYPE: DNA
<213> ORGANISM: Zea mays
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t

<400> SEQUENCE: 59
aatatggcgc catgttatcc aggcatcant cgttggattt cacctcgcca gccgtgtaaa      60
atcttggatt cctgacacng agagatcgca acaacggtac naactacaaa gcgaagcaaa     120
cgatcccggc aggggcgaga gagagagaaa aaaaanagag gagagatcgc gcagaacttt     180
cggatcgatc aggcgctcac c                                               201

<210> SEQ ID NO 60
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 60
```

```
tcgcactcaa tcaggtctct ttccaaccag tgtgatcatg atcatctttg tgacttatat      60
tttaaaggtt atagtgaatt gaagcatttc attttttcc ncagaggagg atcgagctgc     120
aaaggaggtt gaagtcagcc ttctgatgga tgaagttgaa agggctcaag cacgattagt    180
cagtcttgag agggaaaagg t                                              201
```

<210> SEQ ID NO 61  
<211> LENGTH: 201  
<212> TYPE: DNA  
<213> ORGANISM: Zea mays  
<220> FEATURE:  
<221> NAME/KEY: misc_feature  
<222> LOCATION: (101)..(101)  
<223> OTHER INFORMATION: n is a, c, g, or t  
<220> FEATURE:  
<221> NAME/KEY: misc_feature  
<222> LOCATION: (156)..(156)  
<223> OTHER INFORMATION: n is a, c, g, or t

<400> SEQUENCE: 61

```
agcatagtct cgaaaatagg tttgtttctt ttagaaggaa atggaacaa aatgatagta      60 ccattccttt ggcactgcat tgatttaatt tatttgtggt ntatactttt ataggatgaa   120
atgaagatta ttttaaaata cgtgcattta taaagntcaa tctctatttc agattgtgct   180
gacagtgctt gtcaccattt g                                              201
```

<210> SEQ ID NO 62  
<211> LENGTH: 201  
<212> TYPE: DNA  
<213> ORGANISM: Zea mays  
<220> FEATURE:  
<221> NAME/KEY: misc_feature  
<222> LOCATION: (101)..(101)  
<223> OTHER INFORMATION: n is a, c, g, or t

<400> SEQUENCE: 62

```
caactggaac agcaggtctt ttctgtactt ctgtcaccat ttagttatat gctctactat     60
taatttatcg tacatgtctt tgttttttt acttttatat nacattggtg ttacaaataa    120
gagtttcttc ttgtcctatt tctttgtcaa tcataagagt tgacattatc catataataa   180
ttccaattaa aatactagat c                                              201
```

<210> SEQ ID NO 63  
<211> LENGTH: 201  
<212> TYPE: DNA  
<213> ORGANISM: Zea mays  
<220> FEATURE:  
<221> NAME/KEY: misc_feature  
<222> LOCATION: (18)..(18)  
<223> OTHER INFORMATION: n is a, c, g, or t  
<220> FEATURE:  
<221> NAME/KEY: misc_feature  
<222> LOCATION: (46)..(46)  
<223> OTHER INFORMATION: n is a, c, g, or t  
<220> FEATURE:  
<221> NAME/KEY: misc_feature  
<222> LOCATION: (101)..(101)  
<223> OTHER INFORMATION: n is a, c, g, or t  
<220> FEATURE:  
<221> NAME/KEY: misc_feature  
<222> LOCATION: (187)..(187)  
<223> OTHER INFORMATION: n is a, c, g, or t

<400> SEQUENCE: 63

```
ctaggcatcg tctaggcntc caggcggtgc tccaacgcct tggacngcct taccgcttta     60
aaaaccatgc atgctagtga aatatttggt aatatatgca natatctgtg tccagaattc   120
```

```
accattctag acattaattt atgcaaatat gctaatttgc caagaatttt gcttatattg      180
tgcttgntgt acatgtactt t                                               201

<210> SEQ ID NO 64
<211> LENGTH: 394
<212> TYPE: DNA
<213> ORGANISM: Zea mays
<220> FEATURE:
<221> NAME/KEY: misc_feature
<222> LOCATION: (295)..(295)
<223> OTHER INFORMATION: n is a, c, g, or t

<400> SEQUENCE: 64
cctcccaact gtggtcaact cgccggagat accggtattt ccgctgatgg agcagacgcc      60
ggcgccgacg ccagctacag gcagggcgc tggcgcctgt ggtgcacaag gcgttggagt      120
cagcgtcgac agggcggagg ccgcgccgag gaaagactgg cacagcaaga tatgcaccgc    180
cggcgggatg agggaccgcc ggatgcggct ctcccttgac gtcgcccgca agttcttcga    240
gctgcaggac atgcttggat tcgacaaggc cagcaagacg gtacaatggc tcatnaacac    300
gtccaaggcc gccatccagg agatcatggc cgacgacgcg tcgtcggagt gcgtggaaga    360
cggctccagc agcctctctg tcgacggtaa gtac                                394

<210> SEQ ID NO 65
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 65
gttaaaaaaa acttaagtaa gccaggtgtg ttgctgctgc tcgcgatatg caaaggtcgt     60
tcgactgttt tttaaaaaaa aaacatgcca actcgcttct nttccattcg tgtgctatct    120
tgattgagcg tagtttgtat cagtgttctc agtgtgcggg cccgggaaga gaagcgcggg    180
aagtagatag aatcgacgcg g                                              201

<210> SEQ ID NO 66
<211> LENGTH: 645
<212> TYPE: DNA
<213> ORGANISM: Zea mays
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t
<220> FEATURE:
<221> NAME/KEY: misc_feature
<222> LOCATION: (483)..(483)
```

```
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (559)..(561)
<223> OTHER INFORMATION: n is a, c, g, or t
<220> FEATURE:
<221> NAME/KEY: misc_feature
<222> LOCATION: (564)..(568)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t
<220> FEATURE:
<221> NAME/KEY: misc_feature
<222> LOCATION: (584)..(591)
<223> OTHER INFORMATION: n is a, c, g, or t
<220> FEATURE:
<221> NAME/KEY: misc_feature
<222> LOCATION: (595)..(596)
<223> OTHER INFORMATION: n is a, c, g, or t
<220> FEATURE:
<221> NAME/KEY: misc_feature
<222> LOCATION: (605)..(609)
<223> OTHER INFORMATION: n is a, c, g, or t
<220> FEATURE:
<221> NAME/KEY: misc_feature
<222> LOCATION: (614)..(623)
<223> OTHER INFORMATION: n is a, c, g, or t
<220> FEATURE:
<221> NAME/KEY: misc_feature
<222> LOCATION: (625)..(644)
<223> OTHER INFORMATION: n is a, c, g, or t

<400> SEQUENCE: 66
cagctcctca acgccgattt cggcggccgc aagatcatcc gccgcgccga aatcgaggca      60
cgcgagctcc agcgcatccg cgaggtcgag cgccagctcc tcctccaaaa gcagcacagg     120
cattcccgcc cgctgtcctc cccctccagt tcctcctcaa gctcctcgcc cacctccgca     180
gccgctgacg ccgacgccga cgcgtcgcgg gcagagagcg gctccaagga gtcgctcccg     240
agggaggagg tcatccggcg cctgcgcgtg ctgcggcagc cggccacgct cttcggcgag     300
gangacatcg cgcgcctccg ccgcctccag gtcctgatcg aggacnccgg cgcgctcgcc     360
gacatcgacg cggcggagat cggggagggc cagaccaacg acttcctccg cganatccag     420
gcgatgcgtg ctaangctgc gactgtcacg aagcccaagg cggccggcgc ggagnccgag     480
cgnggggagg gcgacagcgt atcgatagat gtgccgttcg aggagctctg ngacgaggac     540
aagatcacng cgttcttcnn nagnnnnntg nacgagtgga cccnnnnnnn ngacnntatg     600
cctgnnnnng aacnnnnnnn nnnannnnnn nnnnnnnnnn nnnnc                    645

<210> SEQ ID NO 67
<211> LENGTH: 352
<212> TYPE: DNA
<213> ORGANISM: Zea mays
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
```

```
<220> FEATURE:
<221> NAME/KEY: misc_feature
<222> LOCATION: (265)..(265)
<223> OTHER INFORMATION: n is a, c, g, or t

<400> SEQUENCE: 67
gagacctaat gtggttactc tgatttgtgt catcaaggcc tgtgttggtg ctggtgaatt      60
tgatcttgcc atgggtgttg tgggattggc agtcaaatgc aacttgtttg aaaagagtat     120
cgaggtacac aattctttga tcactctgta tctaagaatg ggagatgcag ctgcggcacn     180
cagggtgttt gatgacatgg aggtgagaga tgttgtttca tggactgcat tacttgatgt     240
gtatgctgan ttgggtgacc ttganggagc acgacgggtt cttgatgcaa tgcctgcgag     300
gaacgaggtc tcctggggta cattgattgc aaggcatgag cagaaaggtg at            352

<210> SEQ ID NO 68
<211> LENGTH: 736
<212> TYPE: DNA
<213> ORGANISM: Zea mays
<220> FEATURE:
<221> NAME/KEY: misc_feature
<222> LOCATION: (325)..(325)
<223> OTHER INFORMATION: n is a, c, g, or t
<220> FEATURE:
<221> NAME/KEY: misc_feature
<222> LOCATION: (378)..(384)
<223> OTHER INFORMATION: n is a, c, g, or t
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (669)..(673)
<223> OTHER INFORMATION: n is a, c, g, or t
<220> FEATURE:
<221> NAME/KEY: misc_feature
<222> LOCATION: (727)..(730)
<223> OTHER INFORMATION: n is a, c, g, or t

<400> SEQUENCE: 68
atcagccact ggtataataa atgtttctgg tgcctttttt tcttttaatt aatgtacata      60
gtagataact gaagcactaa tcttaattgt gtggcttgca ttgcaggctg aacacgcacg     120
cggtgatcga gccgttcgta atcgcgacaa accggcagct cagcgtggtg catcccgtgc     180
acaagctgct gagcccgcac taccgtgaca cgctgaacat caacgccctg gcacgccaga     240
cactcatcaa cgccggcggc gtcttcgagc gcaccgtgtt ccctgcaaag tacgcgctgg     300
ggatgtcggc agacgtgtac aaganctgga atttcaacga gcaggctctc ccagcagatc     360
tcgtcaagag gtacgtannn nnnncataca tagatcgact acacgtactg aggtgcctat     420
agaaaactgt tcggttcttg acgtggttnn gtngtntgcg tgcgttcaga ggtgtggctg     480
tgccggacca gtcaagccca tatggtgtcc gactgctgat caaagactac ccctatgccg     540
ttgacgggct cgtcatctgg tgggcgatcg ancggtgggt caaggagtac ctggacatct     600
```

| | |
|---|---|
| actaccctaa cgacggcgag ctccagcgtg acgtggagct gcaggcgtgg tggaaggagg | 660 |
| tgcgtgagnn nnngcacggc gacctcaagg accgagactg gtggcccagg atggacaccg | 720 |
| tccagcnnnn gtaccg | 736 |

```
<210> SEQ ID NO 69
<211> LENGTH: 201
<212> TYPE: DNA
<213> ORGANISM: Zea mays
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t

<400> SEQUENCE: 69
```

| | |
|---|---|
| tgcatngtta gtggtgangt aatttcagag aacttctttg gtgttaaact gccgctttcg | 60 |
| gcacatcatc tgctacctaa gggtctggcc atggttctta ntatctattt tgcgaaggtt | 120 |
| gctggtcctg aagggatata tcagttactt attatgtgcc cagttatcca ggctatgctt | 180 |
| cttccttcnt cgattatacc c | 201 |

```
<210> SEQ ID NO 70
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t

<400> SEQUENCE: 70
```

| | |
|---|---|
| ttctttgtta aggtcagtgg gtggtcatct gggtttctga cttcttttaa atgtacaaat | 60 |
| tacaaaatag ctgctcatgt ttagttcgat cattgtatgt nctgtaatac ctaaatttta | 120 |
| taccatgcag tctgctatca gtcctgatgg aactcacatc cttggtggat caagtgangg | 180 |
| aagtgtatac ttgtggcagg t | 201 |

```
<210> SEQ ID NO 71
<211> LENGTH: 201
<212> TYPE: DNA
<213> ORGANISM: Zea mays
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
```

<220> FEATURE:
<221> NAME/KEY: misc_feature
<222> LOCATION: (195)..(195)
<223> OTHER INFORMATION: n is a, c, g, or t

<400> SEQUENCE: 71
actgagtagc atcagtgttn agcagagaca aatcattccc tcttcttctc tggtttctgg   60
accttgacat aaggcaaaaa tccaagaagg taggtgattc ncgcctccca cccgcgctgc  120
tgagcccgac agaacatnag gaatgtgttt gcatagtatg agttgaggcc cataagcaca  180
tgccaccatg cgtgnccctg c                                            201

<210> SEQ ID NO 72
<211> LENGTH: 201
<212> TYPE: DNA
<213> ORGANISM: Zea mays
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 72 atacccctttt ggttgagatt ccagattntt ggcaacaaat ctggtttaga aagctgaacc   60
aaacacaccc ttaagctgcc agttgatcca tcataagaga naactacatt accttagttt  120
tttttccatg cacctggtga tgaagattgg gtaaaaacat aaaatagaac aaaacggatc  180
tctcaacaaa tgtgctaatc a                                            201

<210> SEQ ID NO 73
<211> LENGTH: 201
<212> TYPE: DNA
<213> ORGANISM: Zea mays
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t

<400> SEQUENCE: 73
gatttttttg gaagttgtta cntcttttgc acaaaaaaaa agatcaatgc aaacattaca   60
tggtgagccc actgtgcagc gcaaaatgca cgtgaatatc ntgcaatgcg cagaacaaaa  120
aggtaaanat tgcacaaaaa gagtccaaca atacnatgtt ccatgtcacc caatggccnt  180
cagctcaaca aatcaaattg t                                            201

<210> SEQ ID NO 74
<211> LENGTH: 201
<212> TYPE: DNA

```
<213> ORGANISM: Zea mays
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t

<400> SEQUENCE: 74
tattttctta agtatattcc tatttcattt gatttcaggg agattaaggt ccatcgaagg      60
aagnttaaaa aggctgttgc taagaaaaca gggatctcgc naacagactc ttgaatcgta     120
caccaactta caagcttgat aggcttgtcc ttgaaagata tcagatgaac taaacatgat    180
tattcatgag ttcatngagt a                                               201

<210> SEQ ID NO 75
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 75
gctttggtgc cagagtattt ggcaccatac tcgcagctgg aagtgaacca atcaattgtg      60
tgcacccttt ttttttccat ggactctgtt tcttgtctgt ntatgcttcc attttctgag    120
aacttgtaag gcaacgtgtc tcttgtctaa tgttttatat ctttcctcgt gtaggcttct    180
gcagcatatc aatatcatgc a                                               201

<210> SEQ ID NO 76
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t

<400> SEQUENCE: 76
tgaatacgaa ttggaaccgg gcaaagaaat gaactacagc aaaggcagca ccatatagga      60
aaaggaaggt tggcattgtg ctcctgtaat gccagtccgg ngaataaagg acatacatat    120
aaagaaggat ctcccagacc attgngtct cgtcactctg ttgtaggctg gaaaacagaa    180
catcaacaaa ggaacatgtt a                                               201

<210> SEQ ID NO 77
<211> LENGTH: 201
<212> TYPE: DNA
<213> ORGANISM: Zea mays
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
```

<222> LOCATION: (57)..(57)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 77
tagggaacga aggaaatatg agtgnaagac gggcgaccgg cactcccagg aactccngca    60
tgctggctcc accnagntag aagtggaaga gaacagagta nggtacgggt acggcacaaa   120
gtgcagggac aactactcta ttaccctgct tagttctcca ccaattcact cattaaccta   180
tattacaatc caggagttac a                                              201

<210> SEQ ID NO 78
<211> LENGTH: 201
<212> TYPE: DNA
<213> ORGANISM: Zea mays
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 78
ganctgctgc nagcagacgg ttgtgagaaa gctaaaatat atttggttga accactgtca    60
actgtagatt ctgtaagngc atgataactt ggtaacatgg ntggcaggaa tctagaaaat   120
ctaggatatg aggtgattct aaattgaact atataaatct acagattttc agaaatatat   180
tctgctatta taccccttg g                                              201

<210> SEQ ID NO 79
<211> LENGTH: 201
<212> TYPE: DNA
<213> ORGANISM: Zea mays
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 79
atataaagaa ggatctccca gaccattggn gtctcgtcac tctgttgtag gctggaaaac    60
agaacatcaa caaggaaca tgttaccaaa aaagaatat natgcacaaa atagagtaaa    120
cgttatgaac aaaatagagt aaacgttatg aaaattaagt acaagatgac taaacaggtc   180
acagagatag gaagtttatg a                                                    201

<210> SEQ ID NO 80
<211> LENGTH: 201
<212> TYPE: DNA
<213> ORGANISM: Zea mays
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 80
tgcaaatttt gatcgtactg gcgcatcttt gaccagtntt ttgcgaacgt gttttcagga     60
ccttgtaccg aacggaacga aacccgcggt accactacag nagtgggcct acctgccagt    120
gagccatcgc ncgcgaaaat ccagcagcga aagaaccagn caaccagcgc cgccgcagct    180
tccgcggctt atttttnttt t                                              201

<210> SEQ ID NO 81
<211> LENGTH: 201
<212> TYPE: DNA
<213> ORGANISM: Zea mays
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t

<400> SEQUENCE: 81
actcagaccc ttactacgca ggcgttgttg cnccctatgg aagtcaanat gtggtactat     60
tctatgtcga tttattaagn attattaatc atggggcctc nttcatgcaa attttaatag    120
ccttacctgg gctaactcaa tctcgaatgc cattacctct tgaagtgtcc gaggagcctg    180
tctatgtgaa ngccaagcag t                                              201

<210> SEQ ID NO 82
<211> LENGTH: 738
<212> TYPE: DNA
<213> ORGANISM: Zea mays

```
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (523)..(646)
<223> OTHER INFORMATION: n is a, c, g, or t
<220> FEATURE:
<221> NAME/KEY: misc_feature
<222> LOCATION: (653)..(655)
<223> OTHER INFORMATION: n is a, c, g, or t
<220> FEATURE:
<221> NAME/KEY: misc_feature
<222> LOCATION: (659)..(660)
<223> OTHER INFORMATION: n is a, c, g, or t
<220> FEATURE:
<221> NAME/KEY: misc_feature
<222> LOCATION: (665)..(669)
<223> OTHER INFORMATION: n is a, c, g, or t
<220> FEATURE:
<221> NAME/KEY: misc_feature
<222> LOCATION: (687)..(691)
<223> OTHER INFORMATION: n is a, c, g, or t
<220> FEATURE:
<221> NAME/KEY: misc_feature
<222> LOCATION: (693)..(701)
<223> OTHER INFORMATION: n is a, c, g, or t
<220> FEATURE:
<221> NAME/KEY: misc_feature
<222> LOCATION: (703)..(709)
<223> OTHER INFORMATION: n is a, c, g, or t
<220> FEATURE:
<221> NAME/KEY: misc_feature
<222> LOCATION: (712)..(721)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (727)..(729)
<223> OTHER INFORMATION: n is a, c, g, or t

<400> SEQUENCE: 82
catgcctgca gtgaactcaa acatcaccgt acgtaacacc aatgcgaaat atcaattttc      60
tcattgtagg gaaactgatt gatattaaca tgacgtgtta acggctttac aataggcaca     120
ttatccagta gagtttagtt gtttcttact tttacaacgg ctccaagcga agcttagaaa     180
cgaaccaaac gattcattcg cgaggcaaga tagcacacat ncttccacgc cgtaagcatt     240
tcactggtac aggacacgag gagagaaaag gtcagtctct tgagaagttc agccaacttt     300
ctgagcgtaa ataagtttgc agttgctaac ctcggggtag cagtcctgat gtactatagt     360
ttggttgtgt ggattaacat gaaccacgca agatattctc ccctgcaaga agccaagaac     420
aatcattaaa tccttgttcg attattccta tcccatgtgg attggatgag attagaaaaa     480 atataaaga ttttgatttg tttgggattt aaacccaccg ttnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnatct tannnaatnn     660 acctnnnnng agagcaaaac gaacatnnnn ngnnnnnnnn ntnnnnnnna cnnnnnnnnn     720
ntcanannna gtatacag                                                  738

<210> SEQ ID NO 83
<211> LENGTH: 201
<212> TYPE: DNA
<213> ORGANISM: Zea mays
<220> FEATURE:
```

<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t

<400> SEQUENCE: 83
tcccgcctcc cagtacagaa acttagtctn aacttcttgt ggtcgttgga attgatgggt    60
cgcgatggga gcatacgaca atttctaccg catagaccac nctaccctac ttttatgcat   120
ccgcgtctgg ttgctgttgg atacatgtac aatgccacnt catcatgtaa atcccacgcn   180
cgcatcctct tcgggtacct g                                             201

<210> SEQ ID NO 84
<211> LENGTH: 201
<212> TYPE: DNA
<213> ORGANISM: Zea mays
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t

<400> SEQUENCE: 84
gtcgcgatgg gagcatacga caatttctac cgcatagacc acnctaccct acttttatgc    60
atccgcgtct ggttgctgtt ggatacatgt acaatgccac ntcatcatgt aaatcccacg   120
cncgcatcct cttcgggtac ctgccngaca aagctttaca tacgnttgcc acggtaatgg   180
cgcaaagtat gatgacgccg g                                             201

<210> SEQ ID NO 85
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t

<400> SEQUENCE: 85

```
aggtgccatt aaaagcaaca gaaaatgaag ggaaatagtg aattgttatg caaacacagc      60
aagatggggg tcatgttata gtactatgtt atgctcatat ntagccgtgt aatcccattt     120
ggaacatgga agtctaaagg gaagactggg cttnatgaaa aatggtggtn gtggaattca    180
taaggatgaa gaacagtaat a                                              201
```

<210> SEQ ID NO 86
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t

<400> SEQUENCE: 86

```
gtttgactta aaagcaaaat ttgaatgtca ctgcttgcaa aatcatttca aactgcaggt     60
ttatagctgt gtttaggtct agtttagaaa ctctattttt nggagagatt tatattttta   120
taaagaaaaa ataaattatt ttttttaaga aaataaaaat ancttattaa aaatatggtt   180
ttctaaacta gccttaaata t                                              201
```

<210> SEQ ID NO 87
<211> LENGTH: 201
<212> TYPE: DNA
<213> ORGANISM: Zea mays
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 87

```
tcgtgggatn attataaaaa agacgcaatt gtaagaaagt aatcgaaaga agcttgggat     60
gattgatcaa caatttaat gacgtgtttt ccaaatacga naaacaacca atcgctccaa    120
ttccccaacc aaattttgga cgaagaaata gaggtgttac taacatcaca gagattgaag   180
agttttacag attatacatg t                                              201
```

<210> SEQ ID NO 88
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 88

```
acaaccaatc gctccaattc cccaaccaaa ttttggacga agaaatagag gtgttactaa     60
catcacagag attgaagagt tttacagatt atacatgtag ncaatggtga taaaaactca   120
acgagatcac caagatctaa gccctgatct tgtcacgtct cactccaact cccacatcac   180
gctcttctgc tctccacgac c                                              201
```

<210> SEQ ID NO 89
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 89
aagaagctgc ttctggcgcc atgggggatc aagttggaac ggatagagtg gtgccctggt    60
gtgggatcgg aggggtcgat gatcagatat tggtttggca naaataaagc tatggcggtt   120
ggcgaggaga gtttggttcg tggctatata tgncanactt tgcctaaggt tantcgttcg   180
aactaacctt agagccnttt g                                             201

<210> SEQ ID NO 90
<211> LENGTH: 201
<212> TYPE: DNA
<213> ORGANISM: Zea mays
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t

<400> SEQUENCE: 90
ctggtgaagc tagaatcctc gtgagaagnt ggactgacga cggtgggtgt ncagaatggt    60
natcgaccat aatataaacg gaggcgataa ttggacggaa nagagatagg aaacacgttc   120
gattatcaga dacgttcggc cagctagcga aaggnggagg aggcgatagc tagacaagag   180
tagaagaggt gacttcttcc t                                             201

<210> SEQ ID NO 91
<211> LENGTH: 442
<212> TYPE: DNA
<213> ORGANISM: Zea mays
<220> FEATURE:
<221> NAME/KEY: misc_feature

```
<222> LOCATION: (168)..(168)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (430)..(438)
<223> OTHER INFORMATION: n is a, c, g, or t

<400> SEQUENCE: 91
tgctcacttg ggcggaagcg acgccgatga catataaaac acgatccaac aagctcaagc      60
ctgtcgttga tccctgtaa ataacctggg tggcgttgct ctttaggcag ccgacagccg     120
gggattgctc cattgaaata attcgccggc gtaaattgtt gctgttcnag gtgacatgat    180
cgtatccctc cctccctccc gttgtccctg gaagtcatta gatgttaccg ctgtatatgt    240
gcgtaacctg tgttgcttat aagtccatct gagttgtatg ccaagcacta gtgaccaaat    300
aagtaaagta aatttctcaa gtgtctggtc gacctgggtg tcaagcgagg gcagtatgta    360
caaatcanat ggacttataa gcaacacagg ttacgcacat atacagcggt aacatctaat    420
gactttcagn nnnnnnnnga gg                                             442

<210> SEQ ID NO 92
<211> LENGTH: 1226
<212> TYPE: DNA
<213> ORGANISM: Zea mays
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (845)..(860)
<223> OTHER INFORMATION: n is a, c, g, or t

<400> SEQUENCE: 92
cgaggattcg gccgggnggc tcccccaagc cgagcccccc acaccggaca gaaaagcgcc      60
actaaaaccc tagccatccg ccatgtccac ctccccagcc gcctcatcct ccgctccgac    120
cgccttcgcc gcctctgcgg ttacgatggc tgccgaggcc gccgacgggc cggtactcag    180
cgtagtatcg aagcgtctcc gcgcgctgcg gaagaagtac aatcgnatca cgcagatgga    240
ggagtcgctc gccgccggca agtcgctcaa ccgagagcag gaggaggttc tccgctccaa    300
gcccgtcgtc gctgctctga tcgacgagct cgagcgcctc cgcccccgc tcgcatcagc    360 tctcgcggag gagctctcct cccgctctgc ccccgcccct gctccgcggt tgcctcctcc    420
caactaagtt caagcttcag attcgtcagt ccaggacctc ctcgcgctcg tctactttgg    480
ctccctcttc gatgtcaagc aacaaagcga cttcgtctct ttggtataca cgcgcgagct    540
cgagcggagc agctgcctca cttatgacta cgtcgggat gatccggaag acagtctcgt    600
ggagaccgat ctgaacgccg tttctgccct tgccaccctc gcggcgtcgc gcctcctgc    660 tgcagctgga gtctctcacc gtgatgccct ccaggcttgt gcccatcacg cccgcctctg    720
gctcaaccgt gcggatgaac ccatccaccc tgactccacc atcacatatg ctggggtgag    780
ggcaaagctg gatagaatca tggcatcggg ctactacaca gctcagctag aaatgaggac    840
accannnnnn nnnnnnnnnn cagtggcaaa ctttggagcc ggaggtgtgc aggtgcaaga    900
```

| | |
|---|---|
| gagcatggtt gtgtcgcctc aggcactgga agcagtcgag gggagccagg atgttgaaga | 960 |
| acacaaggac gagaaggaag attctcaggc tacagaaatc tacagtgacc atcaggctcc | 1020 |
| tgttgttgac gctgaacatg tggatgatga aggcctggtg aacccagctc atgaagttcc | 1080 |
| ttcagctgag gcagagcagg agacatttga cgattatgtg gacgatcagg aacaaaaaga | 1140 |
| ccaacaattc acccagcggc gctcttacca gaaccagcgt agtggcggcg tcgtggtgg | 1200 |
| cggcaggagg ggctatccta atggtc | 1226 |

<210> SEQ ID NO 93
<211> LENGTH: 3056
<212> TYPE: DNA
<213> ORGANISM: Zea mays
<220> FEATURE:
<221> NAME/KEY: misc_feature
<222> LOCATION: (953)..(953)
<223> OTHER INFORMATION: n is a, c, g, or t
<220> FEATURE:
<221> NAME/KEY: misc_feature
<222> LOCATION: (1535)..(1535)
<223> OTHER INFORMATION: n is a, c, g, or t

<400> SEQUENCE: 93

| | |
|---|---|
| gttccctcc cattcttctc gtacgcgatc gattgcgagt tgcgcccctc gccctcgccc | 60 |
| ggtcgccccc cccagtcccc gaaactgctc cgcctccacg cccgcgcccg ctcgccctga | 120 |
| ccacggcgat ggccgccgcc gccctccgct cctccgcacg ccggctcctg cgcctcgccc | 180 |
| cggcagcctc gtcggctctg tccgctggtt cccggcccac agccggggct gcgccgctca | 240 |
| cgcgccccat cgccgcgctc tcaggtggca acaatcctat ctcatggaaa ctgagacggt | 300 |
| tctacagttc aaatgaaaaa cacttgcctg caatatctga tccagaaata gaatctgcat | 360 |
| ttaaggattt gttggctgct agttggaatg aacttccaga ttctcttgta gcggaagcaa | 420 |
| agaaagcagc atctaaagcc accgatgata gtgctggtca agaggctttg aaaaatgtat | 480 |
| ttcgtgcagc tgaggcatgt gaagaattta gtggaacttt ggttacccta agaatggctc | 540 |
| ttgatgatct ttgtggcctg actggcgaaa atgtgggtcc cttacctggt tatattgaag | 600 |
| atgctgttaa agctgcatat aatcgctaca tgacatatct ggagtccttt ggtcctgagg | 660 |
| aaaactatct aagaaagaag gtggagactg agttggggac aaaaatgata caccctcaaaa | 720 |
| tgcgatgcag tggcataggt tctgagtggg gaaagatctc cctgattggc acctcaggga | 780 |
| tctcaggttc ctatgttgag ctaagggcat gatgggacgt ctgcaggtaa ccatggaaat | 840 |
| catcgatgag ctgaggaagt ctgtagatca gaatatgcca gtactgcatt tcctttccc | 900 |
| cttcctagct agcatggcaa taacaatgag atcatcaaac agcggcgcgg ttnaaggaac | 960 |
| ttcagatact cccggccctt gtgtctgtgt ctttgtctgt aataagaacg tgtatatgcg | 1020 |
| tgaaacctat cagttctgtt attttttggc atgcgcctga cttcttgttc aactggtgtg | 1080 |
| agttgtatgc tttgttcatg aagcactgat caatgatcat atgccttcgc ccgcaacaga | 1140 |
| acttccttca gcactgcaaa aatacagtga cctgccattt ttttatgaaa gggtttaaca | 1200 |
| atcactatgt gattagtgtt cactaactag tggattgtag catgttaaat catcaattaa | 1260 |
| aaatgtgtca tgtacttaag atgatgtgaa catgagattt aatgtgtagt tattgcaaga | 1320 |
| ataatatgag tttacttgcc cccgtttaaa tcctaagatc cacaataaat tttagacata | 1380 |
| ataagtgatt aattctgaat acaaaattaa ctaaatattg attcagctaa aatagatata | 1440 |
| ctacttgtta tgaggtcgaa aaaggtggaa aaacgagtca tacgagttgc aacgaatatg | 1500 |
| ggctaatcgg atcagagtca gaccacaaca tgcgnggtgc atacaagaca gctaggctag | 1560 |

```
atataggttg tacttgtatg ccataagcaa aaaaatgctc atttcaatac tatacaaatt    1620
gaaggtgtta tttggaagcc ttaaccacta ggctagagat catttcgata gaataggtga    1680
taggatgggt taactgatgg agacaactta agtggcctgg aattatttga tacggtttat    1740
gaaacctatc tctattttac atagtaatgt atcactagta caaattcttt ctatatataa    1800
tgtatcgaga gcataactga actgcataac tgaactgtac ttgcatccga cttttccgc     1860 ttgattggtt acccgcatca tcttgttctg actgcgtgcg ttgactttat acgagtatat    1920
atttgattac atgtatgtgg aagacccgaa ctatatgagt ggatacaaaa taatttattt    1980
taagatcatt tgactgtctc catccatacg gtagaaacga gggtattggc ccagttaggc    2040
tcacgcccac ctggcttcgc acacccagcc atccaatcat gtatttagat tcttagccac    2100
tcgatcatat ttaacggaca caattcctcg acgtattgtt agacatagat gcagatacgg    2160
ttcccttgta gcttctgtaa caaacgtgag agttctaaaa gacaatctaa tgaccgatgg    2220
ggaaaagggg aaaaagaaaa gttgtattcg attgcaatga caggacaatt tagataaggt    2280
tttttgttta gagtaagggg ttagggcatg atcatcctat tgttgtctct agctatctat    2340
tagaattgga ctcatgaaag gggacttccc tgactatcat gcaaccaaac atacataaag    2400
agtgcaaagc gtgtcctaat atactatatg tatatcattg attcatcgag cagagagcat    2460
tggctcattg tggtgtaatt caacaagcaa acacaaaaaa ataaaacata ttgttgtgtg    2520
ccaccaacca actccaagca tattaaaaaa aatcattgct tactgctgca ctaaggccat    2580
tctaaataga tagttccatc acactgtttt caagactgcc atgtaaatat ctgtttagga    2640
aatagtgcat ccaaagtttt gtccccataa aactttctta tctttataa aactcgttca     2700 tatatctctt cattaaatta tatgacatgt catcttattt acttatgtaa catgtcattt    2760
aaagaatgaa actccttta aaaatgacct aattagagtg aaggtgtttt gtcctttagc     2820
caaggtccat ggaaggctgt cactaatcct gactatgcaa taaccgtcat caaatgagca    2880
cgagcttccc ttggaaattc taaactttta ataaatccac caagctcgac aagaagccag    2940
aattgctaaa atcatctgtt tgtagcttcc atcacaccat catttcctca tcacaataaa    3000
gcagtaaggc caaaataact ctcgatggtt ctatagtttt cagagcatga acatat        3056
```

<210> SEQ ID NO 94
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 94

```
agtaacatgg tagtgcagtt cacgaagaaa gcgtggaaaa tgagaggatt ttggctctca     60
tgccaattcc aacgaaacag ccgatttcag ccatgagtat ncggttttgt tttcattcat    120
atggggctcg ccttgccgtg aagctggcac cactgtttgt agatggagaa gtaatctctc    180
atgatgtgta atcatttaga t                                              201
```

<210> SEQ ID NO 95
<211> LENGTH: 201
<212> TYPE: DNA
<213> ORGANISM: Zea mays
<220> FEATURE:
<221> NAME/KEY: misc_feature
<222> LOCATION: (60)..(60)

```
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 95
tgagcttgat aatgcaagct tttgttttga cagatgcctt gcttcacaat ttttggttcn      60
caagggaggt gtagngnatg tatatgttca gctaatattg ntccggtcag tgagtgcatt     120
aaatttccgc aattcatggc gggcttggtc tgttttatgt ttgttaaaac ctgggctgga    180
agaatagaaa tctgtaaaca t                                              201

<210> SEQ ID NO 96
<211> LENGTH: 201
<212> TYPE: DNA
<213> ORGANISM: Zea mays
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 96
acgggaggtg tagagnaggg agtgcaggtg acggagaagc aaaattggtt gctttgcgaa      60
caacacacnt accggtacga caccgacatt ccgacaataa ngtgtggatt gaccttgtca     120
gtcacagaag ggcggagcag tgccagtgta ctggccgcca ccactcgcca ctcgtccccc    180 tcccccccgaa agccggcacg a                                             201

<210> SEQ ID NO 97
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 97
cataatgaag agattacact tccagtttca agatggggat tacactaacc ttcgcattca      60
tgatggttga gttgaccaca actgatgctg ccaaaacatt ntctgagaaa agagcataat     120
ggtaaagatc aggatttttcc aagttctcgc tattggggaa cttttctttttc tctggagaga  180 gaaggtaata atcaattgtt a                                              201

<210> SEQ ID NO 98
<211> LENGTH: 201
<212> TYPE: DNA
<213> ORGANISM: Zea mays
<220> FEATURE:
<221> NAME/KEY: misc_feature
```

```
<222> LOCATION: (101)..(101)
<223> OTHER INFORMATION: n is a, c, g, or t

<400> SEQUENCE: 98
ctgtctccag tagtataaac tcgtgttctg ctattggcag ttaagcagca ttacgctgct      60
gctagaagct aattattaca ccacttgctt gaccattata nacagtcgct ccctccatat     120
cttcttcata cagaaaccac ccaaatgatg tggcacagga agaatgcag atgatgagcg      180 gagaccaaag agctgagcct g                                                201

<210> SEQ ID NO 99
<211> LENGTH: 201
<212> TYPE: DNA
<213> ORGANISM: Zea mays
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t

<400> SEQUENCE: 99
acgtacaata catatatgat gctactctat ntagtgtggc atacacgacc gtccgttcga      60
gtcgcgntac tcgtggaatc aacgtttgct gtctgcgagg ncctcaaact tcgacttgat    120
gttacatcac cttgtctctt tgatctcgta ttctcattct tccttcttca tgtataatgt    180
gncgcgttct tgaagaccca a                                                201

<210> SEQ ID NO 100
<211> LENGTH: 201
<212> TYPE: DNA
<213> ORGANISM: Zea mays
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 100
tgatgcntat tgttgttgaa agggttgcaa ccttaactac agcactaacc gccttatcca      60
aggatcaaac acaaaaggcc aaacctgtga agatttactg ntgtattaca taattacaag   120
attaccctgg aatgtttcgc ntgtctgtaa accgaagaaa aatagttggt tccaaacatc    180
```
ccagntacta gcctgtntgc a                                                        201

<210> SEQ ID NO 101
<211> LENGTH: 201
<212> TYPE: DNA
<213> ORGANISM: Zea mays
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t

<400> SEQUENCE: 101
gaagaaaaat agttggttcc aaacatccca gntactagcc tgtntgcacc ttggcgcgca            60
gaggctggag ttgatttttc ctttatcgaa aaggaaatat ntctaagcct ctaaccattt          120
ttgcattcta tgcagtgtca cctcatcaga gagttaatag ttaatcaagc ctcccaaaac          180
ctncatttat taatgagcca g                                                    201

<210> SEQ ID NO 102
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 102
ggctaattct tttgccttat taaatcacac ataccacact atctattctc ctagacattt            60
acttggcatg cagtagcatc tatatgtact atctgtatgt ncaccaaatt aaagagtaac          120
aagctcaatt taaagcttct gccgtgggca tgatgtatat tacacattcg tggtgccctt          180
tgttactctt gtcatcaatg a                                                    201

<210> SEQ ID NO 103
<211> LENGTH: 201
<212> TYPE: DNA
<213> ORGANISM: Zea mays
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 103
tttctttggt agaattggat gaacaacacc tgtcatgcct ccttagtttc tgatctgtgg            60
gnattctgct cngccagcac aagagttgtg tgcacctgta nagaacaaca acagggacaa          120
tgctcatgac acagattgat agatgaagtt ggaggtcatt gccagatctg catatgttac          180

```
tgctgtagtg ggttgaactg a                                              201
```

<210> SEQ ID NO 104
<211> LENGTH: 201
<212> TYPE: DNA
<213> ORGANISM: Zea mays
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t

<400> SEQUENCE: 104

```
aactgtgttt ggcctcatga gctggggcaa gccaaaatac ggtgggaatc caaacaacat     60
cagttttctt ggtcaacnga cagattttgg cttggcagtc ntggacgttc atccaaaccc   120
acccttaaac tcttatacaa ggcagtgtta attaatagga aaaaacnaaa cgggatgcat   180
tgctttgtnc atttttttnta a                                            201
```

<210> SEQ ID NO 105
<211> LENGTH: 201
<212> TYPE: DNA
<213> ORGANISM: Zea mays
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t

<400> SEQUENCE: 105

```
taattagtac tnacaaagta acacttgttt gtgactgtac aaacttatag caagttagca     60
actctaatgg tgaatcaaaa gttctcgtgc ttcatctatg ntaatcagta ctaacacggc   120
tgataaaaac ttgcagaaat ataatatgtt cgtcgcccag atcggttgtg cggctttggg   180
cgtattagcc ctntcgttgt t                                             201
```

<210> SEQ ID NO 106
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (123)..(123)

```
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t

<400> SEQUENCE: 106
tgcctgattt gagcactttg tctgtgaaat tggattaaat aaatggagaa cagccattgg      60
ttctactgtt tctggtgttc tgctatttct tagttcaatt ntgtggtctg atgaaagaga     120
ggngatgtta ctaatgattt ctttggtaga attggatgaa caacacctgt catgcctcct     180
tagtttctga tctgtgggna t                                               201

<210> SEQ ID NO 107
<211> LENGTH: 201
<212> TYPE: DNA
<213> ORGANISM: Zea mays
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 107 aagtttata ntgtncgctg ctttacgcaa tttctgtagt tacatggctc ctgttcattc      60
ccagttccag aactgatata atcaatttac cgtaaacatt natatctgtc tcctttcaag    120
tacaatttct atccttctta acttgtgcag gtcgtgatta gtccagaatc gcagtcaagg    180
aaaagaaatc gttggattct t                                              201

<210> SEQ ID NO 108
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t

<400> SEQUENCE: 108
attttagctt aagtaccatg actctggacg agaaaaggtg tgtagtcctt ccgttggtca      60
gtggaacatg aacaacaagg tattacatgt tattttcttt ntgagctcca ctttacttt     120 atccaatcac accaaaatta tatttttttg ataaggattc tagtttcatg tgtacctgta    180
atgttgttgg cgtgncactt t                                              201

<210> SEQ ID NO 109
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 109
```

```
ctttggcttc attatcgaaa ttataatgat gaaacggtgc ttcttgtcat gatggactaa      60
aagaacatac tatcctgtat gtatcctagc ttctcaaaga ntaaagaact aagtctagtg     120
tcatttgtct agtatgattc atagttattt tcctatgttg atagcttgct ctctgaaatt     180
catgaatact cactgctctt g                                               201

<210> SEQ ID NO 110
<211> LENGTH: 201
<212> TYPE: DNA
<213> ORGANISM: Zea mays
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t

<400> SEQUENCE: 110
atatctcatg tttgacttct tttagtncat tataaatnca taaaactaaa gattcatgtt      60
ggacttgttt taattcgttt ttcataaatc ccaggaagct nctctatcat taaccagttt     120
attttagttt ttaggattgt cacactgcat ttaaatcnca tattcggtac tggtagtatg     180
ttaattaatc ttggcttgaa t                                               201

<210> SEQ ID NO 111
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t

<400> SEQUENCE: 111
gatacactca cgaccttac gcatcccacc acacagacac cctctcccac aaaaatgggt       60
ggcacatata taatagtgca caaccagtgt aacatataaa naagtgcaaa aatccacttt     120
tntanctgtg tcttatggca ttttgagcaa cagaaattta gttggtactg tttccaattg     180
ctgtccatgt gctgctgctg t                                               201

<210> SEQ ID NO 112
<211> LENGTH: 201
<212> TYPE: DNA
<213> ORGANISM: Zea mays
<220> FEATURE:
<221> NAME/KEY: misc_feature
<222> LOCATION: (9)..(9)
<223> OTHER INFORMATION: n is a, c, g, or t
<220> FEATURE:
```

```
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 112
catctatgnt aatcagtact aacacggctg ataaaaactt gcagaaatat aatatgttcg      60
tcgcccagat cggttgtgcg gctttgggcg tattagccct ntcgttgttt gggcctggct     120
ggttagcaag aggtgcagcc ctttcagcct gtatagcatt catgancatc acgggtgcct     180
cacatcctcc aggtaaatct n                                               201

<210> SEQ ID NO 113
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 113
tattgtatat gatccttctg cggttccatc agttctgact ttttttcttt tcaaactgtg      60
acaggtatgt atccatctca aggtcatttt tctctcagtc ntttggacat ggtggtgata    120
ttggcagtgg tgtggaatgc tggagggggt actaccaaag tctacgtgct acacaaatgg    180
gattgtcttt aaatattggt a                                              201

<210> SEQ ID NO 114
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t

<400> SEQUENCE: 114
tgtgatattg ctttcagccc cctccatgct ttgcattgca attttgggaa gacaaactgg      60
tttgacctag gagatcagct aaccagcagc tcagacttaa ntgttgttac cattgaaaag    120
ctagttgttt gcctttaaat ttgtgcattg gcttagatgg tctggtatgc aagaatatgn    180
cagtgggcat atctgctaca t                                              201

<210> SEQ ID NO 115
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 115
tattcctggt tcgtgtcttc aattgaagcg aaaccttcct tgagcataca caaccatcca      60
```

```
ggtacccact catggatgag tgggtaatat gacctattcc ntctgttgct taacttttct    120
tatctagtgc tgcatttgtc aataacctgc tttaggattg gagtcagctt gtacaaatat    180
atgatacact cacgacccett a                                              201
```

<210> SEQ ID NO 116
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 116

```
tgtgtcttat ggcatttga gcaacagaaa tttagttggt actgtttcca attgctgtcc      60
atgtgctgct gctgtgcaaa ttacatgaca cttggcagtg ncatggtag agcctaggga     120 tcttagggcg cgatcatgtg tgatggtggg tcggcgcttc cacgagtgac gtcgggcagg    180
tgccgtcgga acgggaaaga g                                              201
```

<210> SEQ ID NO 117
<211> LENGTH: 201
<212> TYPE: DNA
<213> ORGANISM: Zea mays
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t

<400> SEQUENCE: 117

```
cgtgtgccag cttggaagag ggctaccttc ctccnattac attcattgtg gtgcaaaagc     60
gccatcacac acggcttttc cctgaagatc atcatgcaca nggacagatg gatcgaagtg    120
gaaacatttt gccaggtaaa ataaatttgc tatcgtttca gtcctctgca ttnttgttt     180 ctggctacta attttntnt g                                               201
```

<210> SEQ ID NO 118
<211> LENGTH: 201
<212> TYPE: DNA
<213> ORGANISM: Zea mays
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (40)..(40)

<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t

<400> SEQUENCE: 118
cgggatgcat tgctttgtnc attttttnta acctagcatn aaaagttcca ttaagtgtac    60
ccaaatgagt tttgaatcag taggacacct ttgacaatta ncattttgca ctagtacttc   120
tngtactatc tttattggtc cttgtccgcg gggtaaggta gcccccaggt gttttgctaa   180
gaagaagacc tcatacaggt c                                             201

<210> SEQ ID NO 119
<211> LENGTH: 201
<212> TYPE: DNA
<213> ORGANISM: Zea mays
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t

<400> SEQUENCE: 119
tgtgaaattg gattaaataa atggagaaca gccattggtt ctactgtttc tggtgttctg    60
ctatttctta gttcaattnt gtggtctgat gaaagagagg ngatgttact aatgatttct   120
ttggtagaat tggatgaaca acacctgtca tgcctcctta gtttctgatc tgtgggnatt   180
ctgctcngcc agcacaagag t                                             201

<210> SEQ ID NO 120
<211> LENGTH: 201
<212> TYPE: DNA
<213> ORGANISM: Zea mays
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 120
gttggacttg tttttaattcg tttttcataa atcccaggaa gctnctctat cattaaccag    60 tttatttttag tttttaggat tgtcacactg catttaaatc ncatattcgg tactggtagt   120
atgttaatta atcttggctt gaatctcttg acagttatat aatatattcc tggttcgtgt   180
cttcaattga agcgaaacct t                                             201

<210> SEQ ID NO 121
<211> LENGTH: 1140

```
<212> TYPE: DNA
<213> ORGANISM: Zea mays
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (163)..(164)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (466)..(467)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (793)..(793)
<223> OTHER INFORMATION: n is a, c, g, or t
<220> FEATURE:
<221> NAME/KEY: misc_feature
<222> LOCATION: (880)..(880)
<223> OTHER INFORMATION: n is a, c, g, or t
<220> FEATURE:
```

<221> NAME/KEY: misc_feature
<222> LOCATION: (937)..(937)
<223> OTHER INFORMATION: n is a, c, g, or t
<220> FEATURE:
<221> NAME/KEY: misc_feature
<222> LOCATION: (1040)..(1041)
<223> OTHER INFORMATION: n is a, c, g, or t
<220> FEATURE:
<221> NAME/KEY: misc_feature
<222> LOCATION: (1137)..(1138)
<223> OTHER INFORMATION: n is a, c, g, or t

<400> SEQUENCE: 121

```
tatacaaaat atatacttgc cctacaaata taacctcaag aggccagtga tagataccaa      60
tggtcatggn atcatggttg gtactcatat tgttaggaat ttcntggcat agccagtgga     120
ccaagctgga aaagaagact tatgctgttc atgatgaaaa nannagatag tatattattg     180
ggctttaata gaatcgtttt gtacttgaaa gttctaatcg anatttttaa agntgttgnt     240
tgcattgaaa cctccantga tgttggcata tcttgtcttg actaagcgtc attttagcac     300
acaattattg ntgttaatcg attagacatg acagcttaca tagaagaaaa caagggctg      360
aattgcaaan ataacctata actctagctt aatcatattc cttaactaac aggtnagata     420
caactccaga gatgacgggc cattccaaac taggaaaaac agtngnnaca tcacaaaatg     480
atccangtga ttagcaaggg ggcaaaatca atgggtgcag gataatgcat agcaaccact     540
ggtactgatc atggcatcat gcaaagtgca ttttacttta gcatgccgca tatgtcgtat     600
gtgagaacac tgtcaaggtg ttctactaag tactaacatc acaaaacaga cagcttgagg     660
tgtggccaga gaaaatgcgg agatgctgac ttggagcgaa aagagaggcc ncttagttgc     720
atggataggn tcatattttc ctctaagtga accaaatttt acaaatggta natatgcaag     780
ggctggtttt aangtcagtc atgaccaagt tcactagaga tcaggaaga catccatgat      840
gacaagacca tgtcatagaa actgcatcct agtgctggtn aacttaaaat acaagaattg     900
gtccaaaaaa tgtcaacagg ggaatagaaa ttaacgncta tacctaaaca gatgtgtcca     960
ttactgtaaa tgtgtggatg catcggtgct ggatgcagaa atataacctg caacaaagga    1020
agacaacatt acaaaaaaan nggcactaaa acccgaagca cacgcaaacg caataatcaa    1080
tcgggggaga agatattgac ctgaggtgcc tccatgggat aatgctcgga gaaatcnncc    1140
```

<210> SEQ ID NO 122
<211> LENGTH: 201
<212> TYPE: DNA
<213> ORGANISM: Zea mays
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 122

```
tacagtcgaa ngggatgtt tgttttgcat atgaagagga ttgcgatttc tgttcacctt       60
tattccttcc gttgttcaga aagaggcgta acttggtgag ngaaaaatac ttttcttctt    120
taggttctgt ttggttacag tccctgtatt tgtctctaga ttgccgtggg atctcccgtg    180
ggactgaagg aaggactaaa c                                              201
```

<210> SEQ ID NO 123
<211> LENGTH: 201

<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 123

```
ggtcggcggt gaaatagcgg agtactcgtt agacatcatg ctcacgtgca tggcagtgtg    60
tccctgccaa aaagaatgg cggagcatcc tgcttttcta ngaaacactc ggtaaaattt    120
catactggga tgcagatgga ccacgcgtta tcgtcttata agtgcctgct aaaaaaatgt   180
tgaagataag tatggtgtca c                                              201
```

<210> SEQ ID NO 124
<211> LENGTH: 201
<212> TYPE: DNA
<213> ORGANISM: Zea mays
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t

<400> SEQUENCE: 124

```
gctgcattag tttnttcacg gtttaaatgt tctgattctg ctcttaatca gatgatgcca    60
tcttggccgg cttttttttt ggcagttggc acgacagttt ncaatctgag acttggcact  120
cgtgagtcgt gagagaaaca agtcgatgtc tagncactca cgtgaaagct ttccggtcgg  180
cggtgaaata gcggagtact c                                              201
```

<210> SEQ ID NO 125
<211> LENGTH: 201
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:

-continued

<221> NAME/KEY: misc_feature
<222> LOCATION: (101)..(101)
<223> OTHER INFORMATION: n is a, c, g, or t

<400> SEQUENCE: 125

```
ggantantttt ttanncnctc cnttttattt nattttagt ccctaaatta ntaaatacgg      60
aaactaaaac agagttttag aaatccccct tgattcccca nttagttctg aataaaaacg     120
acaactccag caaaaccatt ttatctgcag aaacaagccc tggaaagtaa tttcctagaa     180
aagagttcga tagctcaatc a                                               201
```

<210> SEQ ID NO 126
<211> LENGTH: 22
<212> TYPE: DNA
<213> ORGANISM: Zea mays

<400> SEQUENCE: 126

```
ctggagctgc agacaagtaa gt                                               22
```

<210> SEQ ID NO 127
<211> LENGTH: 28
<212> TYPE: DNA
<213> ORGANISM: Zea mays

<400> SEQUENCE: 127

```
agatatgttt gtcattaggt ctgcacat                                         28
```

<210> SEQ ID NO 128
<211> LENGTH: 19
<212> TYPE: DNA
<213> ORGANISM: Zea mays

<400> SEQUENCE: 128

```
gcccggtaca accgatcag                                                   19
```

<210> SEQ ID NO 129
<211> LENGTH: 21
<212> TYPE: DNA
<213> ORGANISM: Zea mays

<400> SEQUENCE: 129

```
gcaaagtgtg gccatgtgat c                                                21
```

<210> SEQ ID NO 130
<211> LENGTH: 18
<212> TYPE: DNA
<213> ORGANISM: Zea mays

<400> SEQUENCE: 130

```
tgtaggcagc ggcatctc                                                    18
```

<210> SEQ ID NO 131
<211> LENGTH: 20
<212> TYPE: DNA
<213> ORGANISM: Zea mays

<400> SEQUENCE: 131

```
agctcccgtc cactcaaatg                                                  20
```

<210> SEQ ID NO 132
<211> LENGTH: 25
<212> TYPE: DNA
<213> ORGANISM: Zea mays

<400> SEQUENCE: 132
caacctcaca tgtaaccaga gatgt                                          25

<210> SEQ ID NO 133
<211> LENGTH: 22
<212> TYPE: DNA
<213> ORGANISM: Zea mays

<400> SEQUENCE: 133
caacctaaaa cacggccaga gt                                             22

<210> SEQ ID NO 134
<211> LENGTH: 24
<212> TYPE: DNA
<213> ORGANISM: Zea mays

<400> SEQUENCE: 134
gtctttcttg cctacttggt ttgg                                           24

<210> SEQ ID NO 135
<211> LENGTH: 18
<212> TYPE: DNA
<213> ORGANISM: Zea mays

<400> SEQUENCE: 135
gttgcccgtg tgcgtgta                                                  18

<210> SEQ ID NO 136
<211> LENGTH: 25
<212> TYPE: DNA
<213> ORGANISM: Zea mays

<400> SEQUENCE: 136
agctgccatc aaaatacaat ctcat                                          25

<210> SEQ ID NO 137
<211> LENGTH: 24
<212> TYPE: DNA
<213> ORGANISM: Zea mays

<400> SEQUENCE: 137
agccattttg cggatctatc agtt                                           24

<210> SEQ ID NO 138
<211> LENGTH: 28
<212> TYPE: DNA
<213> ORGANISM: Zea mays

<400> SEQUENCE: 138
ctgtagtgaa gtttgaacat caatttca                                       28

<210> SEQ ID NO 139
<211> LENGTH: 25
<212> TYPE: DNA
<213> ORGANISM: Zea mays

<400> SEQUENCE: 139
ggtgcttctc attgttatcc cactt                                          25

<210> SEQ ID NO 140
<211> LENGTH: 24
<212> TYPE: DNA

<213> ORGANISM: Zea mays

<400> SEQUENCE: 140
ccattttctg acttacaccg aaca                                    24

<210> SEQ ID NO 141
<211> LENGTH: 20
<212> TYPE: DNA
<213> ORGANISM: Zea mays

<400> SEQUENCE: 141
tcgacttgcg actccatgaa                                         20

<210> SEQ ID NO 142
<211> LENGTH: 28
<212> TYPE: DNA
<213> ORGANISM: Zea mays

<400> SEQUENCE: 142
gttccaagaa aaattcaaat taacatga                                28

<210> SEQ ID NO 143
<211> LENGTH: 21
<212> TYPE: DNA
<213> ORGANISM: Zea mays

<400> SEQUENCE: 143
catggagtgc tgaagctcca g                                       21

<210> SEQ ID NO 144
<211> LENGTH: 19
<212> TYPE: DNA
<213> ORGANISM: Zea mays

<400> SEQUENCE: 144
aaccgcggag cttcagaat                                          19

<210> SEQ ID NO 145
<211> LENGTH: 28
<212> TYPE: DNA
<213> ORGANISM: Zea mays

<400> SEQUENCE: 145
aagctaggat tgatattgtt gacatcgt                                28

<210> SEQ ID NO 146
<211> LENGTH: 26
<212> TYPE: DNA
<213> ORGANISM: Zea mays

<400> SEQUENCE: 146
gaacaagcat gcatatatca ctcgta                                  26

<210> SEQ ID NO 147
<211> LENGTH: 19
<212> TYPE: DNA
<213> ORGANISM: Zea mays

<400> SEQUENCE: 147
cccaaagcgg aacgtgatg                                          19

<210> SEQ ID NO 148
<211> LENGTH: 25

```
<212> TYPE: DNA
<213> ORGANISM: Zea mays

<400> SEQUENCE: 148
atcaagtgct ggaggtattc attt                                           25

<210> SEQ ID NO 149
<211> LENGTH: 27
<212> TYPE: DNA
<213> ORGANISM: Zea mays

<400> SEQUENCE: 149
tgctcatgtt atagggtgga tttactg                                        27

<210> SEQ ID NO 150
<211> LENGTH: 24
<212> TYPE: DNA
<213> ORGANISM: Zea mays

<400> SEQUENCE: 150
tgtagcaaag ggtctgacaa actt                                           24

<210> SEQ ID NO 151
<211> LENGTH: 25
<212> TYPE: DNA
<213> ORGANISM: Zea mays

<400> SEQUENCE: 151
gtggtaacag cctagcatca ttgta                                          25

<210> SEQ ID NO 152
<211> LENGTH: 17
<212> TYPE: DNA
<213> ORGANISM: Zea mays

<400> SEQUENCE: 152
catgcgctcc ccatcgt                                                   17

<210> SEQ ID NO 153
<211> LENGTH: 18
<212> TYPE: DNA
<213> ORGANISM: Zea mays

<400> SEQUENCE: 153
gcggtcctgt tggatgct                                                  18

<210> SEQ ID NO 154
<211> LENGTH: 23
<212> TYPE: DNA
<213> ORGANISM: Zea mays

<400> SEQUENCE: 154
aatgtattcc tcagctggac cct                                            23

<210> SEQ ID NO 155
<211> LENGTH: 32
<212> TYPE: DNA
<213> ORGANISM: Zea mays

<400> SEQUENCE: 155
ctaaatacta gacacggttg tacacatact tc                                  32

<210> SEQ ID NO 156
```

<211> LENGTH: 17
<212> TYPE: DNA
<213> ORGANISM: Zea mays

<400> SEQUENCE: 156
gttcgccatg gctgcct                                                  17

<210> SEQ ID NO 157
<211> LENGTH: 25
<212> TYPE: DNA
<213> ORGANISM: Zea mays

<400> SEQUENCE: 157
cattcctttg gcactgcatt gattt                                         25

<210> SEQ ID NO 158
<211> LENGTH: 22
<212> TYPE: DNA
<213> ORGANISM: Zea mays

<400> SEQUENCE: 158
gcaaaggtcg ttcgactgtt tt                                            22

<210> SEQ ID NO 159
<211> LENGTH: 19
<212> TYPE: DNA
<213> ORGANISM: Zea mays

<400> SEQUENCE: 159
gggccagacc aacgacttc                                                19

<210> SEQ ID NO 160
<211> LENGTH: 26
<212> TYPE: DNA
<213> ORGANISM: Zea mays

<400> SEQUENCE: 160
ctctgtatct aagaatggga gatgca                                        26

<210> SEQ ID NO 161
<211> LENGTH: 20
<212> TYPE: DNA
<213> ORGANISM: Zea mays

<400> SEQUENCE: 161
gggatgtcgg cagacgtgta                                               20

<210> SEQ ID NO 162
<211> LENGTH: 22
<212> TYPE: DNA
<213> ORGANISM: Zea mays

<400> SEQUENCE: 162
gttggcattg tgctcctgta at                                            22

<210> SEQ ID NO 163
<211> LENGTH: 20
<212> TYPE: DNA
<213> ORGANISM: Zea mays

<400> SEQUENCE: 163
cattcgcgag gcaagatagc                                               20

```
<210> SEQ ID NO 164
<211> LENGTH: 25
<212> TYPE: DNA
<213> ORGANISM: Zea mays

<400> SEQUENCE: 164
attgaaataa ttcgccggcg taaat                                              25

<210> SEQ ID NO 165
<211> LENGTH: 17
<212> TYPE: DNA
<213> ORGANISM: Zea mays

<400> SEQUENCE: 165
cgcgctgcgg aagaagt                                                       17

<210> SEQ ID NO 166
<211> LENGTH: 25
<212> TYPE: DNA
<213> ORGANISM: Zea mays

<400> SEQUENCE: 166
gacagatgcc ttgcttcaca atttt                                              25

<210> SEQ ID NO 167
<211> LENGTH: 23
<212> TYPE: DNA
<213> ORGANISM: Zea mays

<400> SEQUENCE: 167
cggcttttcc ctgaagatca tca                                                23

<210> SEQ ID NO 168
<211> LENGTH: 25
<212> TYPE: DNA
<213> ORGANISM: Zea mays

<400> SEQUENCE: 168
aagaggccag tgatagatac caatg                                              25

<210> SEQ ID NO 169
<211> LENGTH: 23
<212> TYPE: DNA
<213> ORGANISM: Zea mays

<400> SEQUENCE: 169
gcactttcag gtttcgtgta tcc                                                23

<210> SEQ ID NO 170
<211> LENGTH: 20
<212> TYPE: DNA
<213> ORGANISM: Zea mays

<400> SEQUENCE: 170
ccgccgtctc tttcatctca                                                    20

<210> SEQ ID NO 171
<211> LENGTH: 21
<212> TYPE: DNA
<213> ORGANISM: Zea mays

<400> SEQUENCE: 171
ggagtaggag accccgatga c                                                  21
```

```
<210> SEQ ID NO 172
<211> LENGTH: 19
<212> TYPE: DNA
<213> ORGANISM: Zea mays

<400> SEQUENCE: 172
cgccgcaggt tatgatcct                                              19

<210> SEQ ID NO 173
<211> LENGTH: 24
<212> TYPE: DNA
<213> ORGANISM: Zea mays

<400> SEQUENCE: 173
tcgttatgcc cttctctctt agct                                        24

<210> SEQ ID NO 174
<211> LENGTH: 25
<212> TYPE: DNA
<213> ORGANISM: Zea mays

<400> SEQUENCE: 174
gacacaaacc acagattaga tgcaa                                       25

<210> SEQ ID NO 175
<211> LENGTH: 26
<212> TYPE: DNA
<213> ORGANISM: Zea mays

<400> SEQUENCE: 175
cagtccatct tgagaatggt ctatgc                                      26

<210> SEQ ID NO 176
<211> LENGTH: 23
<212> TYPE: DNA
<213> ORGANISM: Zea mays

<400> SEQUENCE: 176
tttgcttctc tgaaacacca tca                                         23

<210> SEQ ID NO 177
<211> LENGTH: 22
<212> TYPE: DNA
<213> ORGANISM: Zea mays

<400> SEQUENCE: 177
gcaaggtagg gattcacact ga                                          22

<210> SEQ ID NO 178
<211> LENGTH: 24
<212> TYPE: DNA
<213> ORGANISM: Zea mays

<400> SEQUENCE: 178
tttcatgcag aaacaaacat ggat                                        24

<210> SEQ ID NO 179
<211> LENGTH: 30
<212> TYPE: DNA
<213> ORGANISM: Zea mays

<400> SEQUENCE: 179
tgcttctgaa ttactggcta tatgtacttt                                  30
```

```
<210> SEQ ID NO 180
<211> LENGTH: 28
<212> TYPE: DNA
<213> ORGANISM: Zea mays

<400> SEQUENCE: 180
tgaaatttgg taaaagaac agggcaat                                              28

<210> SEQ ID NO 181
<211> LENGTH: 25
<212> TYPE: DNA
<213> ORGANISM: Zea mays

<400> SEQUENCE: 181
gccacagaga tattaagcca caaaa                                                25

<210> SEQ ID NO 182
<211> LENGTH: 25
<212> TYPE: DNA
<213> ORGANISM: Zea mays

<400> SEQUENCE: 182
cgcctgcact atgagtactt agatg                                                25

<210> SEQ ID NO 183
<211> LENGTH: 23
<212> TYPE: DNA
<213> ORGANISM: Zea mays

<400> SEQUENCE: 183
ggattgatgg aaagagtgca aca                                                  23

<210> SEQ ID NO 184
<211> LENGTH: 17
<212> TYPE: DNA
<213> ORGANISM: Zea mays

<400> SEQUENCE: 184
tccgtcgctg caacgaa                                                         17

<210> SEQ ID NO 185
<211> LENGTH: 28
<212> TYPE: DNA
<213> ORGANISM: Zea mays

<400> SEQUENCE: 185
gtttgtctat tgaggatatc aggagtgt                                             28

<210> SEQ ID NO 186
<211> LENGTH: 21
<212> TYPE: DNA
<213> ORGANISM: Zea mays

<400> SEQUENCE: 186
cttgtgtgtt cgatgctgca a                                                    21

<210> SEQ ID NO 187
<211> LENGTH: 25
<212> TYPE: DNA
<213> ORGANISM: Zea mays

<400> SEQUENCE: 187
```

-continued caccacttct tgttctccat tgttt    25

<210> SEQ ID NO 188
<211> LENGTH: 17
<212> TYPE: DNA
<213> ORGANISM: Zea mays

<400> SEQUENCE: 188
gcggatcagc cgaaagc    17

<210> SEQ ID NO 189
<211> LENGTH: 26
<212> TYPE: DNA
<213> ORGANISM: Zea mays

<400> SEQUENCE: 189
ccacctgaag taaagagggc tataga    26

<210> SEQ ID NO 190
<211> LENGTH: 19
<212> TYPE: DNA
<213> ORGANISM: Zea mays

<400> SEQUENCE: 190
ctgccacagc cggaatttg    19

<210> SEQ ID NO 191
<211> LENGTH: 24
<212> TYPE: DNA
<213> ORGANISM: Zea mays

<400> SEQUENCE: 191
ccaggaaatc cttcgttgat actg    24

<210> SEQ ID NO 192
<211> LENGTH: 31
<212> TYPE: DNA
<213> ORGANISM: Zea mays

<400> SEQUENCE: 192
ccacatgtta tatgaaagaa atcaggtttg t    31

<210> SEQ ID NO 193
<211> LENGTH: 18
<212> TYPE: DNA
<213> ORGANISM: Zea mays

<400> SEQUENCE: 193
gctcgcgagt cggaatga    18

<210> SEQ ID NO 194
<211> LENGTH: 27
<212> TYPE: DNA
<213> ORGANISM: Zea mays

<400> SEQUENCE: 194
tgtcatccta agtaaagaaa ggttcgt    27

<210> SEQ ID NO 195
<211> LENGTH: 18
<212> TYPE: DNA
<213> ORGANISM: Zea mays

<400> SEQUENCE: 195
gccagggagg tgcagatg                                                       18

<210> SEQ ID NO 196
<211> LENGTH: 28
<212> TYPE: DNA
<213> ORGANISM: Zea mays

<400> SEQUENCE: 196
tgattcattc tggacaatag tgtgacaa                                            28

<210> SEQ ID NO 197
<211> LENGTH: 25
<212> TYPE: DNA
<213> ORGANISM: Zea mays

<400> SEQUENCE: 197
gctgctcgag ttattaaact caagg                                               25

<210> SEQ ID NO 198
<211> LENGTH: 25
<212> TYPE: DNA
<213> ORGANISM: Zea mays

<400> SEQUENCE: 198
gcattcttgc atagcattgt taggt                                               25

<210> SEQ ID NO 199
<211> LENGTH: 21
<212> TYPE: DNA
<213> ORGANISM: Zea mays

<400> SEQUENCE: 199
cggaggaaag aggagctcag a                                                   21

<210> SEQ ID NO 200
<211> LENGTH: 26
<212> TYPE: DNA
<213> ORGANISM: Zea mays

<400> SEQUENCE: 200
cactgtcagc acaatctgaa atagag                                              26

<210> SEQ ID NO 201
<211> LENGTH: 26
<212> TYPE: DNA
<213> ORGANISM: Zea mays

<400> SEQUENCE: 201
acaaactacg ctcaatcaag atagca                                              26

<210> SEQ ID NO 202
<211> LENGTH: 18
<212> TYPE: DNA
<213> ORGANISM: Zea mays

<400> SEQUENCE: 202
gccttgggct tcgtgaca                                                       18

<210> SEQ ID NO 203
<211> LENGTH: 23
<212> TYPE: DNA
<213> ORGANISM: Zea mays

```
<400> SEQUENCE: 203
catctctcac ctccatgtca tca                                              23

<210> SEQ ID NO 204
<211> LENGTH: 19
<212> TYPE: DNA
<213> ORGANISM: Zea mays

<400> SEQUENCE: 204
ctgggagagc ctgctcgtt                                                   19

<210> SEQ ID NO 205
<211> LENGTH: 27
<212> TYPE: DNA
<213> ORGANISM: Zea mays

<400> SEQUENCE: 205
tggtctggga gatccttctt tatatgt                                          27

<210> SEQ ID NO 206
<211> LENGTH: 24
<212> TYPE: DNA
<213> ORGANISM: Zea mays

<400> SEQUENCE: 206
tcctgtacca gtgaaatgct tacg                                             24

<210> SEQ ID NO 207
<211> LENGTH: 25
<212> TYPE: DNA
<213> ORGANISM: Zea mays

<400> SEQUENCE: 207
caacacaggt tacgcacata tacag                                            25

<210> SEQ ID NO 208
<211> LENGTH: 18
<212> TYPE: DNA
<213> ORGANISM: Zea mays

<400> SEQUENCE: 208
ggcgagcgac tcctccat                                                    18

<210> SEQ ID NO 209
<211> LENGTH: 18
<212> TYPE: DNA
<213> ORGANISM: Zea mays

<400> SEQUENCE: 209
aagcccgcca tgaattgc                                                    18

<210> SEQ ID NO 210
<211> LENGTH: 23
<212> TYPE: DNA
<213> ORGANISM: Zea mays

<400> SEQUENCE: 210
ctggcaaaat gtttccactt cga                                              23

<210> SEQ ID NO 211
<211> LENGTH: 25
<212> TYPE: DNA
<213> ORGANISM: Zea mays
```

<400> SEQUENCE: 211
cataagtctt cttttccagc ttggt                                               25

<210> SEQ ID NO 212
<211> LENGTH: 16
<212> TYPE: DNA
<213> ORGANISM: Zea mays

<400> SEQUENCE: 212
tcatcgtcag gcaagt                                                         16

<210> SEQ ID NO 213
<211> LENGTH: 16
<212> TYPE: DNA
<213> ORGANISM: Zea mays

<400> SEQUENCE: 213
tggtagggat gatgac                                                         16

<210> SEQ ID NO 214
<211> LENGTH: 13
<212> TYPE: DNA
<213> ORGANISM: Zea mays

<400> SEQUENCE: 214
tttcgacaac ccc                                                            13

<210> SEQ ID NO 215
<211> LENGTH: 19
<212> TYPE: DNA
<213> ORGANISM: Zea mays

<400> SEQUENCE: 215
tccaacagat ctatgccac                                                      19

<210> SEQ ID NO 216
<211> LENGTH: 15
<212> TYPE: DNA
<213> ORGANISM: Zea mays

<400> SEQUENCE: 216
cttcttgaat cttcg                                                          15

<210> SEQ ID NO 217
<211> LENGTH: 14
<212> TYPE: DNA
<213> ORGANISM: Zea mays

<400> SEQUENCE: 217
ttgtgcccta gcgc                                                           14

<210> SEQ ID NO 218
<211> LENGTH: 18
<212> TYPE: DNA
<213> ORGANISM: Zea mays

<400> SEQUENCE: 218
ttgctagcct aaaccata                                                       18

<210> SEQ ID NO 219
<211> LENGTH: 15
<212> TYPE: DNA

```
<213> ORGANISM: Zea mays

<400> SEQUENCE: 219
agcacagagt ccagg                                                    15

<210> SEQ ID NO 220
<211> LENGTH: 17
<212> TYPE: DNA
<213> ORGANISM: Zea mays

<400> SEQUENCE: 220
ccagtgttgg tacaata                                                  17

<210> SEQ ID NO 221
<211> LENGTH: 15
<212> TYPE: DNA
<213> ORGANISM: Zea mays

<400> SEQUENCE: 221
caccactgta tccat                                                    15

<210> SEQ ID NO 222
<211> LENGTH: 14
<212> TYPE: DNA
<213> ORGANISM: Zea mays

<400> SEQUENCE: 222
agggagtcat ttgc                                                     14

<210> SEQ ID NO 223
<211> LENGTH: 18
<212> TYPE: DNA
<213> ORGANISM: Zea mays

<400> SEQUENCE: 223
attttcatgc aattactc                                                 18

<210> SEQ ID NO 224
<211> LENGTH: 15
<212> TYPE: DNA
<213> ORGANISM: Zea mays

<400> SEQUENCE: 224
tggtatgctg gaaaa                                                    15

<210> SEQ ID NO 225
<211> LENGTH: 17
<212> TYPE: DNA
<213> ORGANISM: Zea mays

<400> SEQUENCE: 225
ctacaaccac ggaacat                                                  17

<210> SEQ ID NO 226
<211> LENGTH: 16
<212> TYPE: DNA
<213> ORGANISM: Zea mays

<400> SEQUENCE: 226
aacatctgag aacatc                                                   16

<210> SEQ ID NO 227
<211> LENGTH: 13
```

```
<212> TYPE: DNA
<213> ORGANISM: Zea mays

<400> SEQUENCE: 227
aagcccagac ttt                                                    13

<210> SEQ ID NO 228
<211> LENGTH: 17
<212> TYPE: DNA
<213> ORGANISM: Zea mays

<400> SEQUENCE: 228
agagtggaaa catagca                                                17

<210> SEQ ID NO 229
<211> LENGTH: 16
<212> TYPE: DNA
<213> ORGANISM: Zea mays

<400> SEQUENCE: 229
cgtgtatcca tgctat                                                 16

<210> SEQ ID NO 230
<211> LENGTH: 18
<212> TYPE: DNA
<213> ORGANISM: Zea mays

<400> SEQUENCE: 230
agcaaagttc tccgctcc                                               18

<210> SEQ ID NO 231
<211> LENGTH: 18
<212> TYPE: DNA
<213> ORGANISM: Zea mays

<400> SEQUENCE: 231
acttggcatt ctccctac                                               18

<210> SEQ ID NO 232
<211> LENGTH: 13
<212> TYPE: DNA
<213> ORGANISM: Zea mays

<400> SEQUENCE: 232
tccccatgct ttc                                                    13

<210> SEQ ID NO 233
<211> LENGTH: 20
<212> TYPE: DNA
<213> ORGANISM: Zea mays

<400> SEQUENCE: 233
ctgtagttcc attcgttgta                                             20

<210> SEQ ID NO 234
<211> LENGTH: 15
<212> TYPE: DNA
<213> ORGANISM: Zea mays

<400> SEQUENCE: 234
accaacgtgt ttgac                                                  15

<210> SEQ ID NO 235
```

```
<211> LENGTH: 18
<212> TYPE: DNA
<213> ORGANISM: Zea mays

<400> SEQUENCE: 235
aatgatgccc ctctgaag                                                 18

<210> SEQ ID NO 236
<211> LENGTH: 19
<212> TYPE: DNA
<213> ORGANISM: Zea mays

<400> SEQUENCE: 236
atgtagtgag ctgagccga                                                19

<210> SEQ ID NO 237
<211> LENGTH: 15
<212> TYPE: DNA
<213> ORGANISM: Zea mays

<400> SEQUENCE: 237
accagacacg taaac                                                    15

<210> SEQ ID NO 238
<211> LENGTH: 16
<212> TYPE: DNA
<213> ORGANISM: Zea mays

<400> SEQUENCE: 238
accacaaaca cactgc                                                   16

<210> SEQ ID NO 239
<211> LENGTH: 16
<212> TYPE: DNA
<213> ORGANISM: Zea mays

<400> SEQUENCE: 239
cccataactg ggctgc                                                   16

<210> SEQ ID NO 240
<211> LENGTH: 19
<212> TYPE: DNA
<213> ORGANISM: Zea mays

<400> SEQUENCE: 240
agaaagccta ctatattta                                                19

<210> SEQ ID NO 241
<211> LENGTH: 16
<212> TYPE: DNA
<213> ORGANISM: Zea mays

<400> SEQUENCE: 241
caacacagat gaaact                                                   16

<210> SEQ ID NO 242
<211> LENGTH: 14
<212> TYPE: DNA
<213> ORGANISM: Zea mays

<400> SEQUENCE: 242
aggctcctaa acct                                                     14
```

```
<210> SEQ ID NO 243
<211> LENGTH: 21
<212> TYPE: DNA
<213> ORGANISM: Zea mays

<400> SEQUENCE: 243
tttatttgtg gtgtatactt t                                      21

<210> SEQ ID NO 244
<211> LENGTH: 19
<212> TYPE: DNA
<213> ORGANISM: Zea mays

<400> SEQUENCE: 244
caactcgctt ctcttccat                                         19

<210> SEQ ID NO 245
<211> LENGTH: 13
<212> TYPE: DNA
<213> ORGANISM: Zea mays

<400> SEQUENCE: 245
cgtgctaaag ctg                                               13

<210> SEQ ID NO 246
<211> LENGTH: 14
<212> TYPE: DNA
<213> ORGANISM: Zea mays

<400> SEQUENCE: 246
ccctgtgtgc cgca                                              14

<210> SEQ ID NO 247
<211> LENGTH: 15
<212> TYPE: DNA
<213> ORGANISM: Zea mays

<400> SEQUENCE: 247
caagacctgg aattt                                             15

<210> SEQ ID NO 248
<211> LENGTH: 15
<212> TYPE: DNA
<213> ORGANISM: Zea mays

<400> SEQUENCE: 248
cagtccggcg aataa                                             15

<210> SEQ ID NO 249
<211> LENGTH: 15
<212> TYPE: DNA
<213> ORGANISM: Zea mays

<400> SEQUENCE: 249
cgtggaagga tgtgt                                             15

<210> SEQ ID NO 250
<211> LENGTH: 17
<212> TYPE: DNA
<213> ORGANISM: Zea mays

<400> SEQUENCE: 250
catgtcacct ggaacag                                           17
```

```
<210> SEQ ID NO 251
<211> LENGTH: 14
<212> TYPE: DNA
<213> ORGANISM: Zea mays

<400> SEQUENCE: 251
cgtgatgcga ttgt                                                        14

<210> SEQ ID NO 252
<211> LENGTH: 16
<212> TYPE: DNA
<213> ORGANISM: Zea mays

<400> SEQUENCE: 252
ctgaccggag caatat                                                      16

<210> SEQ ID NO 253
<211> LENGTH: 18
<212> TYPE: DNA
<213> ORGANISM: Zea mays

<400> SEQUENCE: 253
tccatctgtc cgtgtgca                                                    18

<210> SEQ ID NO 254
<211> LENGTH: 15
<212> TYPE: DNA
<213> ORGANISM: Zea mays

<400> SEQUENCE: 254
ctatgccatg aaatt                                                       15

<210> SEQ ID NO 255
<211> LENGTH: 17
<212> TYPE: DNA
<213> ORGANISM: Zea mays

<400> SEQUENCE: 255
ctcatcgtca agcaagt                                                     17

<210> SEQ ID NO 256
<211> LENGTH: 16
<212> TYPE: DNA
<213> ORGANISM: Zea mays

<400> SEQUENCE: 256
ctggtaggga cgatga                                                      16

<210> SEQ ID NO 257
<211> LENGTH: 18
<212> TYPE: DNA
<213> ORGANISM: Zea mays

<400> SEQUENCE: 257
tttcgataac ccctggtt                                                    18

<210> SEQ ID NO 258
<211> LENGTH: 18
<212> TYPE: DNA
<213> ORGANISM: Zea mays

<400> SEQUENCE: 258
ccaacagatc tgtgccac                                                    18
```

<210> SEQ ID NO 259
<211> LENGTH: 15
<212> TYPE: DNA
<213> ORGANISM: Zea mays

<400> SEQUENCE: 259
cttcttgaac cttcg                                                    15

<210> SEQ ID NO 260
<211> LENGTH: 15
<212> TYPE: DNA
<213> ORGANISM: Zea mays

<400> SEQUENCE: 260
tgtgctctag cgcct                                                    15

<210> SEQ ID NO 261
<211> LENGTH: 18
<212> TYPE: DNA
<213> ORGANISM: Zea mays

<400> SEQUENCE: 261
ttgctagcct acaccata                                                 18

<210> SEQ ID NO 262
<211> LENGTH: 14
<212> TYPE: DNA
<213> ORGANISM: Zea mays

<400> SEQUENCE: 262
agcacggagt ccag                                                     14

<210> SEQ ID NO 263
<211> LENGTH: 17
<212> TYPE: DNA
<213> ORGANISM: Zea mays

<400> SEQUENCE: 263
ccagtgttgc tacaata                                                  17

<210> SEQ ID NO 264
<211> LENGTH: 17
<212> TYPE: DNA
<213> ORGANISM: Zea mays

<400> SEQUENCE: 264
tcaccattgt atccatc                                                  17

<210> SEQ ID NO 265
<211> LENGTH: 14
<212> TYPE: DNA
<213> ORGANISM: Zea mays

<400> SEQUENCE: 265
agggagtgat ttgc                                                     14

<210> SEQ ID NO 266
<211> LENGTH: 17
<212> TYPE: DNA
<213> ORGANISM: Zea mays

<400> SEQUENCE: 266 tttcatgca gttactc 17

<210> SEQ ID NO 267
<211> LENGTH: 13
<212> TYPE: DNA
<213> ORGANISM: Zea mays

<400> SEQUENCE: 267
tgctgaaaaa tct 13

<210> SEQ ID NO 268
<211> LENGTH: 16
<212> TYPE: DNA
<213> ORGANISM: Zea mays

<400> SEQUENCE: 268
tacaaccaca gaacat 16

<210> SEQ ID NO 269
<211> LENGTH: 15
<212> TYPE: DNA
<213> ORGANISM: Zea mays

<400> SEQUENCE: 269
aacatccgag aacat 15

<210> SEQ ID NO 270
<211> LENGTH: 13
<212> TYPE: DNA
<213> ORGANISM: Zea mays

<400> SEQUENCE: 270
aagcccggac ttt 13

<210> SEQ ID NO 271
<211> LENGTH: 15
<212> TYPE: DNA
<213> ORGANISM: Zea mays

<400> SEQUENCE: 271
agagtggaaa cttag 15

<210> SEQ ID NO 272
<211> LENGTH: 16
<212> TYPE: DNA
<213> ORGANISM: Zea mays

<400> SEQUENCE: 272
tcgtgtatcc aggcta 16

<210> SEQ ID NO 273
<211> LENGTH: 19
<212> TYPE: DNA
<213> ORGANISM: Zea mays

<400> SEQUENCE: 273
aagcaaaatt ctccgctcc 19

<210> SEQ ID NO 274
<211> LENGTH: 16
<212> TYPE: DNA
<213> ORGANISM: Zea mays

<400> SEQUENCE: 274
ttggcattgt ccctac 16

<210> SEQ ID NO 275
<211> LENGTH: 13
<212> TYPE: DNA
<213> ORGANISM: Zea mays

<400> SEQUENCE: 275
catccccaag ctt 13

<210> SEQ ID NO 276
<211> LENGTH: 20
<212> TYPE: DNA
<213> ORGANISM: Zea mays

<400> SEQUENCE: 276
ctgtagttcc attcattgta 20

<210> SEQ ID NO 277
<211> LENGTH: 16
<212> TYPE: DNA
<213> ORGANISM: Zea mays

<400> SEQUENCE: 277
agcaaaacca aagtgt 16

<210> SEQ ID NO 278
<211> LENGTH: 16
<212> TYPE: DNA
<213> ORGANISM: Zea mays

<400> SEQUENCE: 278
tgatgcccat ctgaag 16

<210> SEQ ID NO 279
<211> LENGTH: 15
<212> TYPE: DNA
<213> ORGANISM: Zea mays

<400> SEQUENCE: 279
agtgagccga gccga 15

<210> SEQ ID NO 280
<211> LENGTH: 15
<212> TYPE: DNA
<213> ORGANISM: Zea mays

<400> SEQUENCE: 280
ccagagacgt aaacc 15

<210> SEQ ID NO 281
<211> LENGTH: 15
<212> TYPE: DNA
<213> ORGANISM: Zea mays

<400> SEQUENCE: 281
ccacaaacgc actgc 15

<210> SEQ ID NO 282
<211> LENGTH: 16
<212> TYPE: DNA
<213> ORGANISM: Zea mays

<400> SEQUENCE: 282
cccataactc ggctgc                                                    16

<210> SEQ ID NO 283
<211> LENGTH: 21
<212> TYPE: DNA
<213> ORGANISM: Zea mays

<400> SEQUENCE: 283
cctttagaaa gcttactata t                                              21

<210> SEQ ID NO 284
<211> LENGTH: 15
<212> TYPE: DNA
<213> ORGANISM: Zea mays

<400> SEQUENCE: 284
aacacggatg aaact                                                     15

<210> SEQ ID NO 285
<211> LENGTH: 15
<212> TYPE: DNA
<213> ORGANISM: Zea mays

<400> SEQUENCE: 285
aggctcctat acctc                                                     15

<210> SEQ ID NO 286
<211> LENGTH: 22
<212> TYPE: DNA
<213> ORGANISM: Zea mays

<400> SEQUENCE: 286
atttatttgt ggtatatact tt                                             22

<210> SEQ ID NO 287
<211> LENGTH: 18
<212> TYPE: DNA
<213> ORGANISM: Zea mays

<400> SEQUENCE: 287
aactcgcttc tattccat                                                  18

<210> SEQ ID NO 288
<211> LENGTH: 15
<212> TYPE: DNA
<213> ORGANISM: Zea mays

<400> SEQUENCE: 288
tgctaaggct gcgac                                                     15

<210> SEQ ID NO 289
<211> LENGTH: 13
<212> TYPE: DNA
<213> ORGANISM: Zea mays

<400> SEQUENCE: 289
caccctgcgt gcc                                                       13

<210> SEQ ID NO 290
<211> LENGTH: 15
<212> TYPE: DNA
<213> ORGANISM: Zea mays

-continued

```
<400> SEQUENCE: 290
caagagctgg aattt                                                    15

<210> SEQ ID NO 291
<211> LENGTH: 15
<212> TYPE: DNA
<213> ORGANISM: Zea mays

<400> SEQUENCE: 291
cagtccggtg aataa                                                    15

<210> SEQ ID NO 292
<211> LENGTH: 14
<212> TYPE: DNA
<213> ORGANISM: Zea mays

<400> SEQUENCE: 292
cgtggaagaa tgtg                                                     14

<210> SEQ ID NO 293
<211> LENGTH: 17
<212> TYPE: DNA
<213> ORGANISM: Zea mays

<400> SEQUENCE: 293
catgtcacct agaacag                                                  17

<210> SEQ ID NO 294
<211> LENGTH: 16
<212> TYPE: DNA
<213> ORGANISM: Zea mays

<400> SEQUENCE: 294
tgcgtgatac gattgt                                                   16

<210> SEQ ID NO 295
<211> LENGTH: 15
<212> TYPE: DNA
<213> ORGANISM: Zea mays

<400> SEQUENCE: 295
tgaccggaac aatat                                                    15

<210> SEQ ID NO 296
<211> LENGTH: 17
<212> TYPE: DNA
<213> ORGANISM: Zea mays

<400> SEQUENCE: 296
ccatctgtcc atgtgca                                                  17

<210> SEQ ID NO 297
<211> LENGTH: 13
<212> TYPE: DNA
<213> ORGANISM: Zea mays

<400> SEQUENCE: 297
atgccacgaa att                                                      13
```

STABILIZATION OF POLLEN PRODUCTION IN MAIZE

REFERENCE TO RELATED APPLICATIONS

This application claims the benefit of U.S. Provisional Application No. 62/039,316, filed Aug. 19, 2014, and U.S. Provisional Application No. 62/101,298, filed Jan. 8, 2015, each of which is herein incorporated by reference in its entirety.

INCORPORATION OF SEQUENCE LISTING

A sequence listing contained in the file named "MONS366US-sequence_listing.txt" which is 151,729 bytes (measured in MS-Windows®) and created on Jun. 12, 2015, and comprises 297 nucleotide sequences, is filed electronically herewith and incorporated by reference in its entirety.

FIELD OF THE INVENTION

The present invention relates to the field of agricultural biotechnology. More specifically, the invention relates to methods for producing corn plants with improved yield.

BACKGROUND OF THE INVENTION

Advances in molecular genetics have made it possible to select plants based on genetic markers linked to traits of interest, a process called marker-assisted selection (MAS). While breeding efforts to date have provided a number of useful corn lines and varieties with beneficial traits, there remains a need in the art for selection of varieties with further improved traits and methods for their production. In many cases, such efforts have been hampered by difficulties in identifying and using alleles conferring beneficial traits. These efforts can be confounded by the lack of definitive phenotypic assays, as well as other issues such as epistasis and polygenic or quantitative inheritance. In the absence of molecular tools such as MAS, it may not be practical to attempt to produce certain new genotypes of crop plants due to such challenges.

SUMMARY OF THE INVENTION

In one aspect, the present invention provides methods of obtaining corn plants with reduced tassel skeletonization severity comprising: a) providing a population of corn plants; b) detecting in said population a plant comprising a reduced tassel skeletonization allele at a polymorphic locus in, or within 0.5 cM of, a chromosomal segment flanked by loci SEQ ID NO: 30 and SEQ ID NO: 125 on chromosome 5 or at a polymorphic locus in, or within 0.5 cM of, a chromosomal segment flanked by loci SEQ ID NO: 21 and SEQ ID NO: 19 on chromosome 3; and c) selecting said plant from said population based on the presence of said allele. In some embodiments, said segment is flanked by marker loci SEQ ID NO:75 and SEQ ID NO:98. In other embodiments, said segment is flanked by marker loci SEQ ID NO: 3 and SEQ ID NO: 27. In further embodiments, said allele comprises a polynucleotide comprising a sequence selected from the group consisting of: SEQ ID NOs: 1, 3, 19, 21, 27, and 30-125. In some embodiments, step (b) of detecting comprises detecting in said population a plant comprising a first reduced tassel skeletonization allele at a polymorphic locus in, or within 0.5 cM of, a chromosomal segment flanked by loci SEQ ID NO: 30 and SEQ ID NO: 125 on chromosome 5 and a second reduced tassel skeletonization allele at a polymorphic locus in, or within 0.5 cM of, a chromosomal segment flanked by loci SEQ ID NO: 21 and SEQ ID NO: 19 on chromosome 3. In other embodiments, step (a) of providing comprises crossing a first corn plant comprising a reduced tassel skeletonization allele with a second corn plant to produce a population of corn plants. In further embodiments, producing the population of corn plants comprises backcrossing. In yet further embodiments, step (b) of detecting comprises the use of an oligonucleotide probe.

In another aspect, the present invention provides methods of producing corn plants with reduced tassel skeletonization severity comprising: a) crossing a first corn plant comprising a reduced tassel skeletonization allele with a second corn plant of a different genotype to produce one or more progeny plants; and b) selecting a progeny plant based on the presence of said allele at a polymorphic locus in, or within 0.5 cM of, a chromosomal segment flanked by loci SEQ ID NO: 30 and SEQ ID NO: 125 on chromosome 5 or at a polymorphic locus in, or within 0.5 cM of, a chromosomal segment flanked by loci SEQ ID NO: 21 and SEQ ID NO: 19 on chromosome 3; wherein said allele confers reduced tassel skeletonization severity compared to a plant lacking said allele. In some embodiments, said segment is flanked by loci SEQ ID NO: 75 and SEQ ID NO: 98. In further embodiments, said segment is flanked by marker loci SEQ ID NO: 3 and SEQ ID NO: 27. In other embodiments, said polymorphic locus comprises a sequence selected from the group consisting of: SEQ ID NOs: 1, 3, 19, 21, 27, and 30-125. In some embodiments, step (b) of selecting comprises selecting a progeny plant based on the presence of a first reduced tassel skeletonization allele at a polymorphic locus in, or within 0.5 cM of, a chromosomal segment flanked by loci SEQ ID NO: 30 and SEQ ID NO: 125 on chromosome 5 and a second reduced tassel skeletonization allele at a polymorphic locus in, or within 0.5 cM of, a chromosomal segment flanked by loci SEQ ID NO: 21 and SEQ ID NO: 19 on chromosome 3. In further embodiments, said methods further comprising a step of: c) crossing said progeny plant with itself or a second plant to produce one or more further progeny plants; and d) selecting a further progeny plant comprising said allele. In yet further embodiments, step (d) of selecting comprises marker-assisted selection. In some embodiments, said marker-assisted selection comprises selecting a progeny plant based on the presence of said allele in at least one polymorphic sequence selected from the group consisting of: SEQ ID NOs: 1, 3, 19, 21, 27, and 30-125. In further embodiments, said further progeny plant is an F2-F7 progeny plant. In yet further embodiments, producing the progeny plant comprises backcrossing. In some embodiments, backcrossing comprises from 2-7 generations of backcrosses. In further embodiments, backcrossing comprises marker-assisted selection. In yet further embodiments, backcrossing comprises marker-assisted selection in at least two generations or in all generations. In some embodiments, marker-assisted selection comprises selecting a progeny plant based on the presence of said allele in at least one polymorphic locus selected from the group consisting of: SEQ ID NOs: 1, 3, 19, 21, 27, and 30-125. In some embodiments, said first corn plant is an inbred or a hybrid. In some embodiments, said second corn plant is an agronomically elite corn plant. In certain embodiments, said agronomically elite corn plant is an inbred or a hybrid. In further embodiments, the invention provides a corn plant produced by the methods provided herein, or a plant part or seed thereof.

In some aspects, corn plants or methods disclosed herein are used in combination with one or more pesticides including, but not limited to, herbicides, fungicides, insecticides, microbiocides, nematicides, insect repellents, bactericides, and other substances used to control pests. In other aspects, the corn plants or methods disclosed herein are used in combination with one or more triazoles, strobilurins, acylamino acids, pyrimidines, pyridines, aryl phenyl ketones, amides, benzanilides, imidazoles, dinitrophenols, morpholines, phenylsulfamides and organophosphorus cpds, derivatives thereof and combinations thereof which may be applied as seed, foliar, drench or drip treatments.

DETAILED DESCRIPTION OF THE INVENTION

Inflorescence architecture in corn plants is related to the production of seed and to yield performance. In particular, tassel skeletonization is a quantitative trait which significantly impacts yield. Efforts to identify or produce plant lines exhibiting reduced tassel skeletonization severity (TSS) have been hindered by a limited understanding of the genetic loci controlling inflorescence architecture and a lack of available markers for detecting and tracking favorable alleles relating to tassel skeletonization in breeding populations. In particular, previously identified markers thought to be associated with inflorescence architecture loci in corn have not reliably correlated with plant phenotype for either inflorescence architecture or for TSS specifically. The selection and breeding of corn plants having favorable inflorescence architecture therefore remains a significant challenge.

The present invention identifies previously-unknown genetic loci which confer reduced TSS and thus increased yield, and provides novel molecular markers linked to reduced TSS in corn plants. The invention further provides methods for introgression of genetic loci conferring reduced TSS into plant varieties previously lacking such loci, thereby providing plants with new or improved inflorescence architecture traits. The genetic loci, markers, and methods provided by the invention therefore represent a significant advance in the art, enabling production of new varieties with favorable inflorescence architecture.

In some embodiments, the invention therefore provides quantitative trait loci (QTL) that demonstrate significant co-segregation with reduced TSS or with favorable inflorescence architecture. The QTL of the invention can be tracked during plant breeding or introgressed into a desired genetic background in order to provide novel plants exhibiting reduced TSS and one or more other beneficial traits. In particular embodiments, the invention identifies for the first time a QTL on chromosome 5 of the corn genome, designated TSS-5.01, and a QTL on chromosome 3 of the corn genome, designated TSS-3.01, which are associated with reduced TSS.

In other embodiments, the invention provides molecular markers linked to the QTL of the invention and methods of using the markers for detection of and selection for reduced TSS. Embodiments of the invention therefore include specific markers, chromosome intervals comprising the markers, and methods of detecting markers genetically linked to TSS-5.01 to identify plant lines with favorable inflorescence architecture. For example, one embodiment of the invention provides a chromosome interval associated with reduced TSS which is flanked by the markers SEQ ID NO: 30 and SEQ ID NO: 125, or any chromosome interval identified listed in Table 5, or any of the markers listed in Table 1, 2, 3, or 4, and may comprise any other markers genetically linked thereto. In certain embodiments, the invention further provides markers closely genetically linked to, or within approximately 0.5 cM of, SEQ ID NO: 30 or SEQ ID NO: 125, and chromosome intervals whose borders fall between or include such markers. Also provided herein are markers that are useful for detecting the presence or absence of reduced TSS alleles within the QTL of the invention that can be used in marker assisted selection (MAS) breeding programs to produce plants with a desired inflorescence architecture.

Other embodiments of the invention include specific markers, chromosome intervals comprising the markers, and methods of detecting markers genetically linked to TSS-3.01 to identify plant lines with favorable inflorescence architecture. For example, one embodiment of the invention provides a chromosome interval associated with reduced TSS which is flanked by the markers SEQ ID NO: 21 and SEQ ID NO: 19, or any chromosome interval identified listed in Table 5, or any of the markers listed in Table 1, 2, 3, or 4, and may comprise any other markers genetically linked thereto. In certain embodiments, the invention further provides markers closely genetically linked to, or within approximately 0.5 cM of, SEQ ID NO: 3 or SEQ ID NO: 27, and chromosome intervals whose borders fall between or include such markers. Also provided herein are markers that are useful for detecting the presence or absence of reduced TSS alleles within the QTL of the invention that can be used in marker assisted selection (MAS) breeding programs to produce plants with a desired inflorescence architecture.

The invention further provides methods of using the markers identified herein to introgress loci associated with reduced TSS into plants. Thus, one skilled in the art can use the invention to create novel maize plants with reduced TSS by crossing a donor line comprising a QTL associated with reduced TSS into any desired recipient line, with or without MAS. Resulting progeny can be selected to be genetically similar to the recipient line except for the reduced TSS QTL.

Quantitative Trait Loci

The term "chromosome interval" designates a contiguous linear span of genomic DNA that resides on a single chromosome. A chromosome interval may comprise a QTL linked with a genetic trait and the QTL may comprise a single gene or multiple genes associated with the genetic trait. The boundaries of a chromosome interval comprising a QTL are drawn such that a marker that lies within the chromosome interval can be used as a marker for the genetic trait, as well as markers genetically linked thereto. Each interval comprising a QTL comprises at least one gene conferring a given trait, however knowledge of how many genes are in a particular interval is not necessary to make or practice the invention, as such an interval will segregate at meiosis as a linkage block. In accordance with the invention, a chromosomal interval comprising a QTL may therefore be readily introgressed and tracked in a given genetic background using the methods and compositions provided herein.

Identification of chromosomal intervals and QTL is therefore beneficial for detecting and tracking a genetic trait, such as reduced TSS, in plant populations. In some embodiments, this is accomplished by identification of markers linked to a particular QTL. The principles of QTL analysis and statistical methods for calculating linkage between markers and useful QTL include penalized regression analysis, ridge regression, single point marker analysis, complex pedigree analysis, Bayesian MCMC, identity-by-descent analysis, interval mapping, composite interval mapping (CIM), and Haseman-Elston regression. QTL analyses may be performed with the help of a computer and specialized software available from a variety of public and commercial sources known to those of skill in the art.

In some embodiments, the invention provides a chromosomal interval comprising a QTL associated with reduced TSS. The invention also provides multiple markers associated with reduced TSS, for example the markers having the sequence of SEQ ID NOs: 1, 3, 19, 21, 27, and 30-125. The invention therefore provides plants comprising a nucleic acid molecule selected from the group consisting of SEQ ID NOs: 1, 3, 19, 21, 27, and 30-125, fragments thereof, or complements thereof. The present invention further provides a plant comprising alleles of the chromosome interval linked to reduced TSS or fragments and complements thereof as well as any plant comprising any combination of one or more inflorescence architecture loci selected from the group consisting of SEQ ID NOs: 1, 3, 19, 21, 27, and 30-125. Plants provided by the invention may be homozygous or heterozygous for such alleles.

In one embodiment, the chromosome interval associated with reduced TSS contains SEQ ID NOs: 1 and 30-125, and is flanked by the markers SEQ ID NO: 30 and SEQ ID NO: 125. This chromosome interval encompasses markers that co-segregate with reduced TSS in a given population at a p-value ≤0.05. An example of a subinterval associated with reduced TSS includes the interval flanked by SEQ ID NO: 75 and SEQ ID NO: 98, which define a chromosome interval encompassing markers that co-segregate with reduced TSS in populations studied at a p-level <0.05.

In another embodiment, the chromosome interval associated with reduced TSS contains SEQ ID NOs: 3, 19, 21, and 27, and is flanked by the markers SEQ ID NO: 21 and SEQ ID NO: 19. This chromosome interval encompasses markers that co-segregate with reduced TSS in a given population at a p-value <0.05. An example of a subinterval associated with reduced TSS includes the interval flanked by SEQ ID NO: 3 and SEQ ID NO: 27, which define a chromosome interval encompassing markers that co-segregate with reduced TSS in populations studied at a p-level <0.05.

Thus, one skilled in the art can use the invention to create novel maize plants with reduced TSS or desirable inflorescence architecture by associating inflorescence architecture phenotypes with genotypes at previously unknown inflorescence architecture loci in the maize genome. Disclosed herein are chromosome intervals that comprise alleles responsible for phenotypic differences between corn lines with favorable or unfavorable inflorescence architecture traits. The chromosome intervals of the invention are characterized in specific embodiments by genomic regions including and flanked by the markers SEQ ID NO: 30 and SEQ ID NO: 125, which comprise markers within or closely linked to (within 20 cM of) TSS-5.01. The invention also comprises other intervals whose borders fall between or include SEQ ID NO: 30 and SEQ ID NO: 125, or any interval closely linked to those intervals. In certain embodiments, the invention further provides markers closely genetically linked to, or within approximately 0.5 cM of, SEQ ID NO: 30 or SEQ ID NO: 125, and other intervals whose borders fall between or include such markers. In other embodiments, chromosome intervals of the invention are characterized by genomic regions including and flanked by the markers SEQ ID NO: 21 and SEQ ID NO: 19, which comprise markers within or closely linked to (within 20 cM of) TSS-3.01. The invention also comprises other intervals whose borders fall between or include SEQ ID NO: 3 and SEQ ID NO: 27, or any interval closely linked to those intervals. In certain embodiments, the invention further provides markers closely genetically linked to, or within approximately 0.5 cM of, SEQ ID NO: 3 or SEQ ID NO: 27, and other intervals whose borders fall between or include such markers.

Examples of markers useful for this purpose comprise the SNP markers listed in Tables 1, 2, 3, or 4, or any marker linked thereto, including a marker that maps within or is genetically linked to the chromosome intervals described herein, including the termini of the intervals. Such markers can be assayed simultaneously or sequentially in a single sample or population of samples.

Accordingly, the compositions and methods of the present invention can be utilized to guide MAS or breeding maize varieties with a desired complement (set) of allelic forms of chromosome intervals associated with superior agronomic performance (inflorescence architecture, along with any other available markers for yield, disease tolerance, etc.). Any of the disclosed marker alleles can be introduced into a corn line via introgression, by traditional breeding (or introduced via transformation, or both) to yield a corn plant with superior agronomic performance. The number of alleles associated with reduced TSS that can be introduced or be present in a corn plant of the present invention ranges from 1 to the number of alleles disclosed herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein can thus find use within the scope of this invention.

Similarly, by identifying plants lacking a desired marker locus, plants having unfavorable inflorescence architecture can be identified and eliminated from subsequent crosses. These marker loci can be introgressed into any desired genomic background, germplasm, plant, line, variety, etc., as part of an overall MAS breeding program designed to enhance inflorescence. The invention also provides chromosome QTL intervals that can be used in MAS to select plants that demonstrate improved inflorescence architecture traits. The QTL intervals can also be used to counter-select plants that are have increased TSS or unfavorable inflorescence architecture traits.

The present invention also extends to a method of making a progeny corn plant and the resulting progeny corn plants. The method comprises, in an embodiment, crossing a first parent corn plant with a second corn plant and growing the female corn plant parent under plant growth conditions to yield corn plant progeny. Methods of crossing and growing corn plants are well within the ability of those of ordinary skill in the art. Such corn plant progeny can be assayed for alleles associated with reduced TSS as disclosed herein and, thereby, the desired progeny selected. Such progeny plants or seed thereof can be sold commercially for corn production, used for food, processed to obtain a desired constituent of the corn, or further utilized in subsequent rounds of breeding. At least one of the first or second corn plants may be a corn plant of the present invention in that it comprises at least one of the allelic forms of the markers of the present invention, such that the progeny are capable of inheriting the allele.

Often, a method of the present invention may be applied to at least one related corn plant such as from a progenitor or descendant line in the subject corn plants' pedigree such that inheritance of the desired allele can be traced. The number of generations separating the corn plants being subjected to the methods of the present invention may be, in specific embodiments, from 1 to 20 or more, commonly 1 to 10, and including 1, 2, 3, 4, 5, 6, 7, 8, 9, 10 or more generations of separation, and often a direct descendant or parent of the corn plant will be subject to the method (i.e., one generation of separation).

Thus, the invention permits one skilled in the art to detect the presence or absence of inflorescence architecture genotypes in the genomes of corn plants as part of a MAS program. In one embodiment, a breeder ascertains the genotype at one or more markers for a parent having favorable inflorescence architecture, which contains a favorable inflorescence architecture allele, and the genotype at one or more markers for a parent with unfavorable inflorescence architecture, which lacks the favorable inflorescence architecture allele. For example, the markers of the present invention can be used in MAS in crosses involving elite and exotic corn lines by subjecting the segregating progeny to MAS to maintain inflorescence architecture alleles, or alleles associated with yield. A breeder can then reliably track the inheritance of the inflorescence architecture alleles through subsequent populations derived from crosses between the two parents by genotyping offspring with the markers used on the parents and comparing the genotypes at those markers with those of the parents. Depending on how tightly linked the marker alleles are with the trait, progeny that share genotypes with the parent having favorable inflorescence architecture alleles can be reliably predicted to express the desirable phenotype and progeny that share genotypes with the parent having unfavorable inflorescence architecture alleles can be reliably predicted to express the undesirable phenotype. Thus, the laborious, inefficient, and potentially inaccurate process of manually phenotyping the progeny for inflorescence architecture traits is avoided.

By providing the positions in the maize genome of inflorescence architecture chromosome intervals and the associated markers within those intervals, the invention also allows one skilled in the art to identify and use other markers within the intervals disclosed herein or linked to the intervals disclosed herein. Having identified such regions, these markers can be readily identified from public linkage maps.

Closely linked markers flanking the locus of interest that have alleles in linkage disequilibrium with an inflorescence architecture allele at that locus may be effectively used to select for progeny plants with desirable inflorescence architecture traits. Thus, the markers described herein, such as those listed in Tables 1, 2, 3, or 4, as well as other markers genetically linked to the same chromosome interval, may be used to select for maize plants with reduced TSS or improved inflorescence architecture traits. Often, a set of these markers will be used, (e.g., 2 or more, 3 or more, 4 or more, 5 or more) in the flanking regions of the locus. Optionally, as described above, a marker flanking or within the actual locus may also be used. The parents and their progeny may be screened for these sets of markers, and the markers that are polymorphic between the two parents used for selection. In an introgression program, this allows for selection of the gene or locus genotype at the more proximal polymorphic markers and selection for the recurrent parent genotype at the more distal polymorphic markers.

The choice of markers actually used to practice the invention is not limited and can be any marker that is genetically linked to the intervals as described herein, which includes markers mapping within the intervals. In certain embodiments, the invention further provides markers closely genetically linked to, or within approximately 0.5 cM of, the markers provided herein and chromosome intervals whose borders fall between or include such markers, and including markers within approximately 0.4 cM, 0.3 cM, 0.2 cM, and about 0.1 cM of the markers provided herein. Examples include any marker selected from SEQ ID NOs: 1, 30-125, or the markers listed in Tables 1, 2, 3 or 4. Furthermore, since there are many different types of marker detection assays known in the art, it is not intended that the type of marker detection assay used to practice this invention be limited in any way.

Molecular Markers

"Marker," "genetic marker," "molecular marker," "marker nucleic acid," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus.

"Marker" also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A favorable allele of a marker is the allele of the marker that co-segregates with a desired phenotype (e.g., reduced TSS or improved inflorescence architecture). As used herein, a QTL marker has a minimum of one favorable allele, although it is possible that the marker might have two or more favorable alleles found in the population. Any favorable allele of that marker can be used advantageously for the identification and construction of plant lines having the desired phenotype. Optionally, one, two, three or more favorable allele(s) of different markers are identified in, or introgressed into a plant, and can be selected for or against during MAS. Desirably, plants or germplasm are identified that have at least one such favorable allele that positively correlates with reduced TSS or improved inflorescence architecture. Alternatively, a marker allele that co-segregates with inflorescence architecture traits also finds use with the invention, since that allele can be used to identify and counter select these traits in plants. Such an allele can be used for exclusionary purposes during breeding to identify alleles that negatively correlate with desired inflorescence architecture traits, to eliminate plants or germplasm having undesirable phenotypes from subsequent rounds of breeding.

The more tightly linked a marker is with a DNA locus influencing a phenotype, the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype.

Genetic markers are distinguishable from each other (as well as from the plurality of alleles of any one particular marker) on the basis of polynucleotide length and/or sequence. A large number of corn molecular markers are known in the art, and are published or available from various sources, such as the MaizeGDB internet resource. In general, any differentially inherited polymorphic trait (including a nucleic acid polymorphism) that segregates among progeny is a potential genetic marker.

In some embodiments of the invention, one or more marker alleles are selected for in a single plant or a population of plants. In these methods, plants are selected that contain favorable alleles from more than one marker, or alternatively, favorable alleles from more than one marker are introgressed into a desired germplasm. One of skill recognizes that the identification of favorable marker alleles is germplasm-specific. The determination of which marker alleles correlate with improved inflorescence architecture traits is determined for the particular germplasm under study. One of skill recognizes that methods for identifying the favorable alleles are routine and well known in the art, and furthermore, that the identification and use of such favorable alleles is well within the scope of this invention. Identification of favorable marker alleles in plant populations other than the populations used or described herein is well within the scope of this invention.

Marker Detection

In some aspects, methods of the invention utilize an amplification step to detect/genotype a marker locus, but amplification is not always a requirement for marker detection (e.g. Southern blotting and RFLP detection). Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

"Amplifying," in the context of nucleic acid amplification, is any process whereby additional copies of a selected nucleic acid (or a transcribed form thereof) are produced. In some embodiments, an amplification-based marker technology is used wherein a primer or amplification primer pair is admixed with genomic nucleic acid isolated from the first plant or germplasm, and wherein the primer or primer pair is complementary or partially complementary to at least a portion of the marker locus, and is capable of initiating DNA polymerization by a DNA polymerase using the plant genomic nucleic acid as a template. The primer or primer pair is extended in a DNA polymerization reaction having a DNA polymerase and a template genomic nucleic acid to generate at least one amplicon. In other embodiments, plant RNA is the template for the amplification reaction. In some embodiments, the QTL marker is a SNP type marker, and the detected allele is a SNP allele, and the method of detection is allele specific hybridization (ASH).

In general, the majority of genetic markers rely on one or more properties of nucleic acids for their detection. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like). A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST. Details regarding the use of these and other amplification methods can be found in any of a variety of standard texts. Many available biology texts also have extended discussions regarding PCR and related amplification methods and one of skill will appreciate that essentially any RNA can be converted into a double stranded DNA suitable for restriction digestion, PCR expansion and sequencing using reverse transcriptase and a polymerase.

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. TaqMan™ probes are oligonucleotides that have a label and a quencher, where the label is released during amplification by the exonuclease action of the polymerase used in amplification, providing a real time measure of amplification during synthesis. A variety of TaqMan™ reagents are commercially available, e.g., from Applied Biosystems as well as from a variety of specialty vendors such as Biosearch Technologies.

In one embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

While the exemplary markers provided in the figures and tables herein are either SNP markers, any of the aforementioned marker types can be employed in the context of the invention to identify chromosome intervals encompassing genetic element that contribute to superior agronomic performance (e.g., reduced TSS or improved inflorescence architecture).

Probes and Primers

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described. Oligonucleotides, including modified oligonucleotides, can also be ordered from a variety of commercial sources.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radio labels, enzymes, and colorimetric labels. Other labels include ligands which bind to antibodies labeled with fluorophores, chemiluminescent agents, and enzymes. A probe can also constitute radio labeled PCR primers that are used to generate a radio labeled amplicon. It is not intended that the nucleic acid probes of the invention be limited to any particular size.

In some embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers." It will be appreciated that, although many specific examples of primers are provided herein, suitable primers to be used with the invention can be designed using any suitable method. It is not intended that the invention be limited to any particular primer or primer pair. In some embodiments, the primers of the invention are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons. It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length that is longer or shorter than those disclosed herein. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Marker alleles in addition to those recited herein also find use with the present invention.

Linkage Analysis

"Linkage", or "genetic linkage," is used to describe the degree with which one marker locus is associated with another marker locus or some other locus (for example, a TSS or inflorescence architecture locus). A marker locus may be located within a locus to which it is genetically linked. For example, if locus A has genes "A" or "a" and locus B has genes "B" or "b" and a cross between parent 1 with AABB and parent 2 with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ is attributed to linkage. As used herein, linkage can be between two markers, or alternatively between a marker and a phenotype. A marker locus may be genetically linked to a trait, and in some cases a marker locus genetically linked to a trait is located within the allele conferring the trait. A marker may also be causative for a trait or phenotype, for example a causative polymorphism. In a further example, a marker locus can be associated with reduced TSS or improved inflorescence architecture when the marker locus is in linkage disequilibrium with an inflorescence architecture trait. The degree of linkage of a molecular marker to a phenotypic trait (e.g., a QTL) is measured, e.g., as a statistical probability of co-segregation of that molecular marker with the phenotype.

As used herein, "closely linked" means that the marker or locus is within about 20 cM, for instance within about 10 cM, about 5 cM, about 1 cM, about 0.5 cM, or less than 0.5 cM of the identified locus associated with reduced TSS or improved inflorescence architecture.

As used herein, the linkage relationship between a molecular marker and a phenotype is given is the statistical likelihood that the particular combination of a phenotype and the presence or absence of a particular marker allele is random. Thus, the lower the probability score, the greater the likelihood that a phenotype and a particular marker will cosegregate. In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p<0.5). For example, a significant probability can be less than 0.25, less than 0.20, less than 0.15, or less than 0.1. The phrase "closely linked," in the present application, means that recombination between two linked loci occurs with a frequency of equal to or less than about 10% (i.e., are separated on a genetic map by not more than 10 cM). In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked." The frequency with which the traits are inherited together is the primary measure of how tightly the traits are linked, i.e., traits which are inherited together with a higher frequency are more closely linked than traits which are inherited together with lower (but still above random) frequency. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in the marker and the DNA sequence responsible for the trait the marker is designed to track segregating separately into progeny. A common measure of linkage is the frequency with which traits cosegregate.

Linkage analysis is used to determine which polymorphic marker allele demonstrates a statistical likelihood of co-segregation with a desired inflorescence architecture phenotype (an "inflorescence architecture marker allele"). Following identification of a marker allele for co-segregation with the inflorescence architecture phenotype, it is possible to use this marker for rapid, accurate screening of plant lines for reduced TSS or improved inflorescence architecture alleles without the need to grow the plants through their life cycle and await phenotypic evaluations, and furthermore, permits genetic selection for the particular allele even when the molecular identity of the actual inflorescence architecture QTL is unknown. Tissue samples can be taken, for example, from the endosperm, embryo, or mature/developing plant and screened with the appropriate molecular marker to rapidly determine determined which progeny contain the desired genetics. Linked markers also remove the impact of environmental factors that can often influence phenotypic expression.

Because chromosomal distance is approximately proportional to the frequency of crossing over events between traits, there is an approximate physical distance that correlates with recombination frequency. Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation.

When referring to the relationship between two genetic elements, such as a genetic element contributing to inflorescence architecture and a proximal marker, "coupling" phase linkage indicates the state where the "favorable" allele at the inflorescence architecture locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for inflorescence architecture) is physically linked with an "unfavorable" allele at the proximal marker locus, and the two "favorable" alleles are not inherited together (i.e., the two loci are "out of phase" with each other).

Genetic Mapping

A "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a physical map of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map. A "genetic recombination frequency" is the frequency of a crossing over event (recombination) between two genetic loci. Recombination frequency can be observed by following the segregation of markers and/or traits following meiosis. In some cases, two different markers can have the same genetic map coordinates. In that case, the two markers are in such close proximity to each other that recombination occurs between them with such low frequency that it is undetected.

Genetic maps are graphical representations of genomes (or a portion of a genome such as a single chromosome) where the distances between markers are measured by the recombination frequencies between them. Plant breeders use genetic maps of molecular markers to increase breeding efficiency through MAS, a process where selection for a trait of interest is not based on the trait itself but rather on the genotype of a marker linked to the trait. A molecular marker that demonstrates reliable linkage with a phenotypic trait provides a useful tool for indirectly selecting the trait in a plant population, especially when accurate phenotyping is difficult, slow, or expensive.

In general, the closer two markers or genomic loci are on the genetic map, the closer they lie to one another on the physical map. A lack of precise proportionality between cM distances and physical distances can exist due to the fact that the likelihood of genetic recombination is not uniform throughout the genome; some chromosome regions are cross-over "hot spots," while other regions demonstrate only rare recombination events, if any.

Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in guiding MAS.

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that the invention be limited to any particular mapping populations, use of any particular software, or any particular set of software parameters to determine linkage of a particular marker or chromosome interval with a desired phenotype. It is well within the ability of one of ordinary skill in the art to extrapolate the novel features described herein to any gene pool or population of interest, and using any particular software and software parameters. Indeed, observations regarding genetic markers and chromosome intervals in populations in addition to those described herein are readily made using the teaching of the present disclosure.

Association Mapping

Association or LD mapping techniques aim to identify genotype-phenotype associations that are significant. It is effective for fine mapping in outcrossing species where frequent recombination among heterozygotes can result in rapid LD decay. LD is non-random association of alleles in a collection of individuals, reflecting the recombinational history of that region. Thus, LD decay averages can help determine the number of markers necessary for a genome-wide association study to generate a genetic map with a desired level of resolution.

Large populations are better for detecting recombination, while older populations are generally associated with higher levels of polymorphism, both of which contribute to accelerated LD decay. However, smaller effective population sizes tend to show slower LD decay, which can result in more extensive haplotype conservation. Understanding of the relationships between polymorphism and recombination is useful in developing strategies for efficiently extracting information from these resources. Association analyses compare the plants' phenotypic score with the genotypes at the various loci. Subsequently, any suitable maize genetic map (for example, a composite map) can be used to help observe distribution of the identified QTL markers and/or QTL marker clustering using previously determined map locations of the markers.

Marker Assisted Selection

"Introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A primary motivation for development of molecular markers in crop species is the potential for increased efficiency in plant breeding through MAS. Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present invention provides the means to identify plants that exhibit reduced TSS or improved inflorescence architecture by identifying plants having a specified allele that is linked to TSS-5.01.

In general, MAS uses polymorphic markers that have been identified as having a significant likelihood of co-segregation with a desired trait. Such markers are presumed to map near a gene or genes that give the plant its desired phenotype, and are considered indicators for the desired trait, and are termed QTL markers. Plants are tested for the presence or absence of a desired allele in the QTL marker.

Identification of plants or germplasm that include a marker locus or marker loci linked to a desired trait or traits provides a basis for performing MAS. Plants that comprise favorable markers or favorable alleles are selected for, while plants that comprise markers or alleles that are negatively correlated with the desired trait can be selected against. Desired markers and/or alleles can be introgressed into plants having a desired (e.g., elite or exotic) genetic background to produce an introgressed plant or germplasm having the desired trait. In some aspects, it is contemplated that a plurality of markers for desired traits are sequentially or simultaneous selected and/or introgressed. The combinations of markers that are selected for in a single plant is not limited, and can include any combination of markers disclosed herein or any marker linked to the markers disclosed herein, or any markers located within the QTL intervals defined herein.

In some embodiments, a first corn plant or germplasm exhibiting a desired trait (the donor) can be crossed with a second corn plant or germplasm (the recipient, e.g., an elite or exotic corn, depending on characteristics that are desired in the progeny) to create an introgressed corn plant or germplasm as part of a breeding program. In some aspects, the recipient plant can also contain one or more loci associated with one or more desired traits, which can be qualitative or quantitative trait loci. In another aspect, the recipient plant can contain a transgene.

In some embodiments, the recipient corn plant or germplasm will typically display less desirable inflorescence architecture characteristics as compared to the first corn plant or germplasm, while the introgressed corn plant or germplasm will display improved inflorescence architecture traits as compared to the second plant or germplasm. An introgressed corn plant or germplasm produced by these methods are also a feature of this invention.

MAS is a powerful shortcut to selecting for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

When a population is segregating for multiple loci affecting one of multiple traits, e.g., multiple loci involved in inflorescence architecture, or multiple loci each involved in different inflorescence architecture traits, the efficiency of MAS compared to phenotypic screening becomes even greater, because all of the loci can be evaluated in the lab together from a single sample of DNA.

Introgression of Inflorescence Architecture Loci Using MAS

The introgression of one or more desired loci from a donor line into another is achieved via repeated backcrossing to a recurrent parent accompanied by selection to retain one or more d loci from the donor parent. Markers associated with reduced TSS or improved inflorescence architecture are assayed in progeny and those progeny with one or more desired markers are selected for advancement. In another aspect, one or more markers can be assayed in the progeny to select for plants with the genotype of the agronomically elite parent. This invention anticipates that trait introgression activities will require more than one generation, wherein progeny are crossed to the recurrent (agronomically elite) parent or selfed. Selections are made based on the presence of one or more reduced TSS or improved inflorescence architecture markers and can also be made based on the recurrent parent genotype, wherein screening is performed on a genetic marker and/or phenotype basis. In another embodiment, markers of this invention can be used in conjunction with other markers, ideally at least one on each chromosome of the corn genome, to track the introgression of reduced TSS or improved inflorescence architecture loci into elite germplasm. In another embodiment, QTLs associated with reduced TSS or improved inflorescence architecture will be useful in conjunction with SNP molecular markers of the present invention to combine quantitative and qualitative reduced TSS or improved inflorescence architecture in the same plant. It is within the scope of this invention to utilize the methods and compositions for trait integration of reduced TSS or improved inflorescence architecture. It is contemplated by the inventors that the present invention will be useful for developing commercial varieties with reduced TSS or improved inflorescence architecture and an agronomically elite phenotype.

In one aspect, this invention could be used on any plant. In another aspect, the plant is selected from the genus *Zea*. In another aspect, the plant is selected from the species *Zea mays*. In a further aspect, the plant is selected from the subspecies *Zea mays* L. ssp. *mays*. In an additional aspect, the plant is selected from the group *Zea mays* L. subsp. *mays* Indentata, otherwise known as dent corn. In another aspect, the plant is selected from the group *Zea mays* L. subsp. *mays* Indurata, otherwise known as flint corn. In an aspect, the plant is selected from the group *Zea mays* L. subsp. *mays* Saccharata, otherwise known as sweet corn. In another aspect, the plant is selected from the group *Zea mays* L. subsp. *mays* Amylacea, otherwise known as flour corn. In a further aspect, the plant is selected from the group *Zea mays* L. subsp. *mays* Everta, otherwise known as pop corn. *Zea* plants include hybrids, inbreds, partial inbreds, or members of defined or undefined populations.

In another aspect, a corn plant of the invention can show a comparative reduction in TSS or improved inflorescence architecture traits compared to a control corn plant. In this aspect, a control corn plant will preferably be genetically similar except for the TSS or inflorescence architecture allele or alleles in question.

Transgenic Plants

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the present disclosure, this could be used to introduce genes corresponding to, e.g., an entire biosynthetic pathway, into a plant.

Particularly useful for transformation are expression cassettes which have been isolated from such vectors. DNA segments used for transforming plant cells will generally comprise the cDNA, gene, or genes which one desires to introduce into and have expressed in the host cells. These DNA segments can further include structures such as promoters, enhancers, polylinkers, or regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant.

Regulatory elements such as promoters, leaders, enhancers, introns, and transcription termination regions (or 3' UTRs) can play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, and introns that function in plants are therefore useful for modifying plant phenotypes through genetic engineering.

As used herein, the term "intron" refers to a DNA molecule that may be isolated or identified from the genomic copy of a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron. In plants, the inclusion of some introns in constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from *petunia* (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, that splicing per se is not required, as IME in dicotyledonous plants has been shown by point mutations within the splice sites of the pat1 gene from *A. thaliana*. Multiple uses of the same intron in one plant have been shown to exhibit disadvantages. In those cases, it is necessary to have a collection of basic control elements for the construction of appropriate recombinant DNA elements.

As used herein, the term "enhancer" or "enhancer element" refers to a cis-acting regulatory element, a.k.a. cis-element, which confers an aspect of the overall expression pattern, but is usually insufficient alone to drive transcription, of an operably linked DNA sequence. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Regulatory elements may be characterized by their gene expression pattern, e.g., positive and/or negative effects, such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may originate from the 5' untranslated region (5' UTR) of a gene. Alternately, promoters may be synthetically produced or manipulated DNA molecules. Promoters may also be chimeric. As used herein, the term "chimeric" refers to a single DNA molecule produced by fusing a first DNA molecule to a second DNA molecule, where neither the first nor the second DNA molecule would normally be contained in that configuration, i.e., fused to the other. The chimeric DNA molecule is thus a new DNA molecule not otherwise normally contained in nature. As used herein, the term "chimeric promoter" refers to a promoter produced through such manipulation of DNA molecules. A chimeric promoter may combine two or more DNA fragments, for example, the fusion of a promoter to an enhancer element. Thus, the design, construction, and use of chimeric promoters according to the methods disclosed herein for modulating the expression of operably linked transcribable DNA molecules are encompassed by the disclosure.

In specific embodiments, chimeric DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

Exemplary promoters for expression of a nucleic acid sequence include plant promoters such as the CaMV 35S promoter, or others such as CaMV 19S, nos, Adh, sucrose synthase, α-tubulin, actin, cab, PEPCase or those promoters associated with the R gene complex. Tissue-specific promoters such as leaf specific promoters, or tissue selective promoters (e.g., promoters that direct greater expression in leaf primordia than in other tissues), and tissue-specific enhancers are also contemplated to be useful, as are inducible promoters such as ABA- and turgor-inducible promoters. Any suitable promoters known in the art may be used to express defensin or defensin-like coding sequences in a plant. In an embodiment, the CaMV35S promoter may be used to express defensin or defensin-like coding sequences in a plant. In yet another embodiment, a disease or pathogen inducible promoter can be used to express defensin or defensin like proteins. Examples of disease or pathogen inducible promoters can be found in Kooshki et al. *Plant Science* 165 (2003) 213-219, Koschmann et al. *Plant Physiology* 160 (2012) 178-191, Rushton et al. *The Plant Cell,* 14 (2002) 749-762, and Kirsch et al. *The Plant Journal* (2001) 26 217-227.

The DNA sequence between the transcription initiation site and the start of the coding sequence, i.e., the untranslated leader sequence, can also influence gene expression. As used herein, the term "leader" refers to a DNA molecule from the untranslated 5' region (5' UTR) of a gene and defined generally as a DNA segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. One may thus wish to employ a particular leader sequence with a transformation construct of the present disclosure. In an embodiment, leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure. In some embodiments, sequences that are derived from genes that are highly expressed in plants may be used for expression of defensin or defensin-like coding sequences.

It is envisioned that defensin or defensin-like coding sequences may be introduced under the control of novel promoters, enhancers, etc., or homologous or tissue-specific or tissue-selective, or pathogen or disease promoters or control elements. Vectors for use in tissue-specific targeting of genes in transgenic plants will typically include tissue-specific or tissue-selective promoters and may also include other tissue-specific or tissue-selective control elements such as enhancer sequences. Promoters which direct specific or enhanced expression in certain plant tissues will be known to those of skill in the art in light of the present disclosure.

Transformation constructs prepared in accordance with the present disclosure may further include a 3' end DNA sequence that acts as a signal to terminate transcription and allow for the polyadenylation of the mRNA produced by coding sequences operably linked to a promoter. As used herein, the term "3' transcription termination molecule," "3' untranslated region" or "3' UTR" herein refers to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR. 3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR. In one embodiment, the native terminator of a defensin or defensin-like coding sequence may be used. Alternatively, a heterologous 3' end may enhance the expression of sense or antisense defensin or defensin-like coding sequences.

Sequences that are joined to the coding sequence of an expressed gene, which are removed post-translationally from the initial translation product and which facilitate the transport of the protein into or through intracellular or extracellular membranes, are termed transit or targeting peptide (usually into vacuoles, vesicles, plastids and other intracellular organelles) and signal peptide or sequences (usually to the endoplasmic reticulum, Golgi apparatus, and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein.

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the present disclosure.

Selectable marker transgenes may also be used with the present disclosure. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the present disclosure are known in the art and include, but are not limited to, transcribable DNA molecules encoding β-glucuronidase (GUS), green fluorescent protein (GFP), proteins that confer antibiotic resistance, and proteins that confer herbicide tolerance Plant Cell Transformation Methods Numerous methods for transforming chromosomes in a plant cell with recombinant DNA are known in the art and are used in methods of producing a transgenic plant cell and plant. Two effective methods for such transformation are Agrobacterium-mediated transformation and microprojectile bombardment-mediated transformation. Microprojectile bombardment methods are illustrated, for example, in U.S. Pat. Nos. 5,550,318; 5,538,880; 6,160,208; and 6,399,861. Agrobacterium-mediated transformation methods are described, for example in U.S. Pat. No. 5,591,616, which is incorporated herein by reference in its entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores and pollen. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having another recombinant DNA that confers another trait, for example herbicide resistance or pest resistance or enhanced water use efficiency, to produce progeny plants having recombinant DNA that confers both traits. Typically, in such breeding for combining traits the transgenic plant donating the additional trait is the male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant DNA, by application using a selective agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

In transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Transgenic Plants and Seeds

Transgenic plants derived from transgenic plant cells having a transgenic nucleus of this disclosure are grown to generate transgenic plants having an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits, such as reduced TSS or improved inflorescence architecture.

Definitions

The definitions and methods provided define the present invention and guide those of ordinary skill in the art in the practice of the present invention. Unless otherwise noted, terms are to be understood according to conventional usage by those of ordinary skill in the relevant art. Examples of resources describing many of the terms related to molecular biology used herein can be found in in Alberts et al., Molecular Biology of The Cell, $5^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes Icorn, Oxford University Press: New York, 2007. The nomenclature for DNA bases as set forth at 37 CFR § 1.822 is used.

"Adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

"Allele" refers to an alternative nucleic acid sequence at a particular locus; the length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. A favorable allele is the allele at a particular locus that confers, or contributes to, an agronomically desirable phenotype, or alternatively, is an allele that allows the identification of plants that can be removed from a breeding program or planting. A favorable allele of a marker is a marker allele that segregates with the favorable phenotype, or alternatively, segregates with an unfavorable plant phenotype, therefore providing the benefit of identifying plants having the unfavorable phenotype. A favorable allelic form of a chromosome interval is a chromosome interval that includes a nucleotide sequence that contributes to superior agronomic performance at one or more genetic loci physically located on the chromosome interval. "Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele. An allele positively correlates with a trait when it is linked to it and when presence of the allele is an indictor that the desired trait or trait form will occur in a plant comprising the allele. An allele negatively correlates with a trait when it is linked to it and when presence of the allele is an indicator that a desired trait or trait form will not occur in a plant comprising the allele.

"Crossed" or "cross" means to produce progeny via fertilization (e.g. cells, seeds or plants) and includes crosses between plants (sexual) and self fertilization (selfing).

"Elite line" means any line that has resulted from breeding and selection for superior agronomic performance. Numerous elite lines are available and known to those of skill in the art of corn breeding. An "elite population" is an assortment of elite individuals or lines that can be used to represent the state of the art in terms of agronomically superior genotypes of a given crop species, such as corn. Similarly, an "elite germplasm" or elite strain of germplasm is an agronomically superior germplasm.

"Exogenous nucleic acid" is a nucleic acid that is not native to a specified system (e.g., a germplasm, plant, variety, etc.), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts. In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

"Genetic element" or "gene" refers to a heritable sequence of DNA, i.e., a genomic sequence, with functional significance. The term "gene" can also be used to refer to, e.g., a cDNA and/or an mRNA encoded by a genomic sequence, as well as to that genomic sequence.

"Genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome interval. The terms "phenotype," or "phenotypic trait" or "trait" refers to one or more trait of an organism. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, i.e., a "single gene trait." In other cases, a phenotype is the result of several genes.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells that can be cultured into a whole plant.

"Linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. The tern "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci cosegregate at least about 90% of the time, e.g., 91%, 92%, 93%, 94%, 95%, 96%, 97%, 98%, 99%, 99.5%, 99.75%, or more of the time.

"Locus" a chromosome region where a polymorphic nucleic acid, trait determinant, gene or marker is located. The loci of this invention comprise one or more polymorphisms in a population; i.e., alternative alleles are present in some individuals. A "gene locus" is a specific chromosome location in the genome of a species where a specific gene can be found.

"Marker Assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc. "Marker Assisted Selection" (MAS) is a process by which phenotypes are selected based on marker genotypes.

"Molecular phenotype" is a phenotype detectable at the level of a population of one or more molecules. Such molecules can be nucleic acids, proteins, or metabolites. A molecular phenotype could be an expression profile for one or more gene products, e.g., at a specific stage of plant development, in response to an environmental condition or stress, etc.

"Operably linked" refers to the association of two or more nucleic acid elements in a recombinant DNA construct, e.g. as when a promoter is operably linked with DNA that is transcribed to RNA whether for expressing or suppressing a protein. Recombinant DNA constructs can be designed to express a protein which can be an endogenous protein, an exogenous homologue of an endogenous protein or an exogenous protein with no native homologue. Alternatively, recombinant DNA constructs can be designed to suppress the level of an endogenous protein, e.g. by suppression of the native gene. Such gene suppression can be effectively employed through a native RNA interference (RNAi) mechanism in which recombinant DNA comprises both sense and anti-sense oriented DNA matched to the gene targeted for suppression where the recombinant DNA is transcribed into RNA that can form a double-strand to initiate an RNAi mechanism. Gene suppression can also be effected by recombinant DNA that comprises anti-sense oriented DNA matched to the gene targeted for suppression. Gene suppression can also be effected by recombinant DNA that comprises DNA that is transcribed to a microRNA matched to the gene targeted for suppression.

"Percent identity" or "% identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence.

"Phenotype" means the detectable characteristics of a cell or organism which can be influenced by genotype.

"Plant" refers to a whole plant any part thereof, or a cell or tissue culture derived from a plant, comprising any of: whole plants, plant components or organs (e.g., leaves, stems, roots, etc.), plant tissues, seeds, plant cells, and/or progeny of the same. A plant cell is a biological cell of a plant, taken from a plant or derived through culture from a cell taken from a plant.

"Polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

A "population of plants" or "plant population" means a set comprising any number, including one, of individuals, objects, or data from which samples are taken for evaluation, e.g. estimating QTL effects. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

"Recombinant" in reference to a nucleic acid or polypeptide indicates that the material (e.g., a recombinant nucleic acid, gene, polynucleotide, polypeptide, etc.) has been altered by human intervention. The term recombinant can also refer to an organism that harbors recombinant material, e.g., a plant that comprises a recombinant nucleic acid is considered a recombinant plant.

"Tassel skeletonization" or "male barren inflorescence" or "male floret abortion" refers to the proportion of tassels which are skeletonized in a maize plant or a population of maize plants and therefore affects the production of pollen.

"Tassel skeletonization severity" or "TSS" refers to a score calculated from skeletonization intensity and skeletonization frequency in a maize plant or a population of maize plants.

"TSS allele" refers to the nucleic acid sequence associated with reduced or increased TSS in maize plants at a particular locus.

"TSS locus" refers to a locus associated with reduced or increased TSS in maize plants.

"Inflorescence architecture" refers to the morphological characteristics of male or female inflorescence in a maize plant.

"Male inflorescence traits" or "tassel traits" includes a number of traits including, but not limited to, tassel skeletonization, total tassel length, central tassel length, number of tassel branches, length of central spike, branching characteristics, spikelet characteristics, tassel branch number and internode distance, total tassel length, and tassel weight.

"Inflorescence architecture allele" refers to the nucleic acid sequence associated with inflorescence architecture traits in maize plants at a particular locus.

"Inflorescence architecture locus" refers to a locus associated with inflorescence architecture traits in maize plants.

"Transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extrachromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Vector" is a polynucleotide or other molecule that transfers nucleic acids between cells. Vectors are often derived from plasmids, bacteriophages, or viruses and optionally comprise parts which mediate vector maintenance and enable its intended use. A "cloning vector" or "shuttle vector" or "subcloning vector" contains operably linked parts that facilitate subcloning steps (e.g., a multiple cloning site containing multiple restriction endonuclease sites). The term "expression vector" as used herein refers to a vector comprising operably linked polynucleotide sequences that facilitate expression of a coding sequence in a particular host organism (e.g., a bacterial expression vector or a plant expression vector).

"Yield" is the culmination of all agronomic traits as determined by the productivity per unit area of a particular plant product of commercial value. "Agronomic traits," include the underlying genetic elements of a given plant variety that contribute to yield over the course of growing season.

tion trait on a scale of 0-1, which represents 0%-100% of tassels that were skeletonized on a whole plot basis. For example, a score of 0.45 indicates that 45% of tassels were skeletonized. Plants were genotyped with 2053 SNP markers across the maize genome. A genome-wide association study was conducted on mapping population A using step-wise regression and least absolute shrinkage and selection operator (LASSO) (Li, 2012) models. Table 1 lists the top 10 SNP markers associated with the tassel skeletonization trait identified by step-wise regression model. Each row provides the SEQ ID NO of the marker, chromosome location, genetic map positions of the marker, adjusted phenotypic variance ($R^2$) of the marker, regression step, F-statistic, p-value corresponding to the F-statistic, favorable allele, and unfavorable allele. Genetic map loci are represented in cM, with position zero being the first (most distal) marker known at the beginning of the chromosome on both Monsanto's internal consensus genetic map and the Neighbors 2008 maize genomic map, which is freely available to the public from the MaizeGDB website and commonly used by those skilled in the art. As shown in Table 1, 16% phenotypic variance was explained by SEQ ID NO: 1, and 4% (0.2-0.16=0.04) phenotypic variance was explained by SEQ ID NO: 2. SEQ ID NO: 1 was the marker accountable for the largest proportion of phenotypic variance (Table 1).

TABLE 1

Top SNP markers associated with tassel skeletonization trait by step-wise regression model from mapping population A

| SEQ ID NO. | Chr | MON Map cM | IBM2008 Map IcM | Adjusted $R^2$ | Step | F stat | p-value | Favorable allele | Unfavorable allele |
|---|---|---|---|---|---|---|---|---|---|
| 1 | 5 | 48.2 | 181.6 | 0.16 | 1 | 59.69 | 0 | T | C |
| 2 | 5 | 126.7 | 438.9 | 0.2 | 2 | 16.1 | 0 | A | G |
| 3 | 3 | 83.9 | 246.4 | 0.23 | 3 | 12.84 | 0 | A | C |
| 4 | 2 | 114.5 | 375.6 | 0.25 | 4 | 10.26 | 0 | A | G |
| 5 | 5 | 66.7 | 227.7 | 0.26 | 5 | 5.79 | 0.02 | T | C |
| 6 | 3 | 54.4 | 134.2 | 0.27 | 6 | 6.21 | 0.01 | A | G |
| 7 | 5 | 184.3 | 629.6 | 0.28 | 7 | 5.42 | 0.02 | G | A |
| 8 | 3 | 80.2 | 208.6 | 0.3 | 8 | 6.47 | 0.01 | A | G |
| 9 | 7 | 103.3 | 381.2 | 0.31 | 9 | 4.92 | 0.03 | C | T |
| 10 | 10 | 52.8 | 253.5 | 0.32 | 10 | 5.65 | 0.02 | C | A |

EXAMPLES

Example 1

Genome-Wide Association Study (GWAS) of Mapping Population A

Three hundred and twelve male inbred lines from mapping population A were measured for the tassel skeletoniza- Table 2 lists the top 20 SNP markers (SEQ ID NOs) associated with tassel skeletonization trait identified by LASSO model. Each row provides the SEQ ID NO of the marker, chromosome location, genetic map positions of the marker on Monsanto's internal consensus map and the Neighbors 2008 maize genomic map (publicly available at Maize GDB website), logarithm of the odds (LOD) score, estimated marker effect on tassel skeletonization trait, favorable allele, and unfavorable allele. SEQ ID NO: 1 at 48.2 cM on chromosome 5 was among the top 20 SNP markers identified, with a LOD score of 1.94 and marker effect of 0.005 (Table 2).

TABLE 2

Top SNP markers with largest LOD scores by LASSO model from mapping population A

| SEQ ID NO. | Chr | MON Map cM | IBM2008 Map IcM | LOD | Marker Effect | Favorable allele | Unfavorable allele |
|---|---|---|---|---|---|---|---|
| 11 | 5 | 33.7 | 132.2 | 9.8 | −0.012 | A | G |
| 12 | 5 | 117.4 | 401 | 6.63 | 0.01 | G | C |
| 13 | 2 | 81.1 | 248.2 | 4.76 | −0.008 | C | T |
| 14 | 9 | 0.5 | −17.5 | 3.61 | 0.007 | G | C |
| 15 | 2 | 85.2 | 267.4 | 2.54 | −0.006 | A | G |
| 16 | 8 | 28.6 | 71.1 | 2.53 | −0.006 | C | T |
| 17 | 2 | 81 | 247.9 | 2.28 | −0.005 | A | G |
| 18 | 7 | 102.5 | 372.9 | 2.09 | 0.005 | G | A |
| 19 | 3 | 116.8 | 404 | 1.99 | −0.005 | A | C |
| 20 | 3 | 42.6 | 102.9 | 1.98 | −0.005 | C | G |
| 21 | 3 | 82.2 | 216.8 | 1.97 | 0.005 | G | A |
| 1 | 5 | 48.2 | 181.6 | 1.94 | 0.005 | T | C |
| 22 | 8 | 75.9 | 245.4 | 1.92 | −0.005 | A | T |
| 23 | 4 | 77.5 | 217.4 | 1.83 | 0.004 | C | A |
| 24 | 7 | 185.1 | 612.3 | 1.77 | 0.004 | T | C |
| 25 | 5 | 190 | 638.8 | 1.74 | −0.004 | C | G |
| 26 | 8 | 71.7 | 216.2 | 1.54 | −0.004 | A | T |
| 27 | 3 | 115.9 | 401.2 | 1.52 | −0.004 | C | T |
| 28 | 5 | 5.2 | 46.6 | 1.47 | 0.004 | G | A |
| 29 | 1 | 218.7 | 862.2 | 1.41 | −0.004 | T | G |

One QTL associated with the tassel skeletonization trait was mapped to 40-49.7 cM on chromosome 5 of a Monsanto internal consensus map and was designated as TSS-5.01. Table 3 lists Monsanto internal SNP markers within the TSS-5.01 region.

TABLE 3

SNP markers associated with TSS-5.01

| SEQ ID NO. | Chr | MON Map cM | IBM2008 Map IcM |
|---|---|---|---|
| 30 | 5 | 40 | 156.9 |
| 31 | 5 | 40 | 156.9 |
| 32 | 5 | 40 | 156.9 |
| 33 | 5 | 40.6 | 160.1 |
| 34 | 5 | 40.6 | 160.1 |
| 35 | 5 | 40.6 | 160.1 |
| 36 | 5 | 40.9 | 161.7 |
| 37 | 5 | 40.9 | 161.7 |
| 38 | 5 | 41.2 | 163.4 |
| 39 | 5 | 41.2 | 163.4 |
| 40 | 5 | 41.2 | 163.4 |
| 41 | 5 | 41.5 | 165 |
| 42 | 5 | 41.5 | 165 |
| 43 | 5 | 41.6 | 165.5 |
| 44 | 5 | 41.6 | 165.5 |
| 45 | 5 | 41.6 | 165.5 |
| 46 | 5 | 41.8 | 162.6 |
| 47 | 5 | 42 | 159.7 |
| 48 | 5 | 42.1 | 160.1 |
| 49 | 5 | 42.2 | 160.4 |
| 50 | 5 | 42.2 | 160.4 |
| 51 | 5 | 42.2 | 160.4 |
| 52 | 5 | 42.2 | 160.4 |
| 53 | 5 | 42.2 | 160.4 |
| 54 | 5 | 42.2 | 160.4 |
| 55 | 5 | 42.2 | 160.4 |
| 56 | 5 | 42.2 | 160.4 |
| 57 | 5 | 42.2 | 160.4 |
| 58 | 5 | 42.2 | 160.4 |
| 59 | 5 | 42.2 | 160.4 |
| 60 | 5 | 42.2 | 160.4 |
| 61 | 5 | 42.2 | 160.4 |
| 62 | 5 | 42.2 | 160.4 |
| 63 | 5 | 42.2 | 160.4 |
| 64 | 5 | 42.5 | 161.5 |
| 65 | 5 | 43.2 | 164.1 |
| 66 | 5 | 47.3 | 179.2 |
| 67 | 5 | 47.3 | 179.2 |
| 68 | 5 | 47.3 | 179.2 |
| 69 | 5 | 47.3 | 179.2 |
| 70 | 5 | 47.4 | 179.6 |
| 71 | 5 | 47.8 | 180.4 |
| 72 | 5 | 47.8 | 180.4 |
| 73 | 5 | 47.8 | 180.4 |
| 74 | 5 | 47.8 | 180.4 |
| 75 | 5 | 47.8 | 180.4 |
| 76 | 5 | 47.8 | 180.4 |
| 77 | 5 | 47.8 | 180.4 |
| 78 | 5 | 47.8 | 180.4 |
| 79 | 5 | 47.8 | 180.4 |
| 80 | 5 | 47.8 | 180.4 |
| 1 | 5 | 48.2 | 181.2 |
| 81 | 5 | 48.2 | 181.2 |
| 82 | 5 | 48.3 | 181.5 |
| 83 | 5 | 48.3 | 181.5 |
| 84 | 5 | 48.3 | 181.5 |
| 85 | 5 | 48.3 | 181.5 |
| 86 | 5 | 48.3 | 181.5 |
| 87 | 5 | 48.4 | 181.7 |
| 88 | 5 | 48.4 | 181.7 |
| 89 | 5 | 48.4 | 181.7 |
| 90 | 5 | 48.4 | 181.7 |
| 91 | 5 | 48.5 | 182 |
| 92 | 5 | 48.9 | 183 |
| 93 | 5 | 48.9 | 183 |
| 94 | 5 | 48.9 | 183 |
| 95 | 5 | 48.9 | 183 |
| 96 | 5 | 48.9 | 183 |
| 97 | 5 | 49 | 183.3 |
| 98 | 5 | 49.1 | 183.5 |
| 99 | 5 | 49.1 | 183.5 |
| 100 | 5 | 49.5 | 184.6 |
| 101 | 5 | 49.5 | 184.6 |
| 102 | 5 | 49.5 | 184.6 |
| 103 | 5 | 49.5 | 184.6 |
| 104 | 5 | 49.5 | 184.6 |
| 105 | 5 | 49.5 | 184.6 |
| 106 | 5 | 49.5 | 184.6 |
| 107 | 5 | 49.5 | 184.6 |
| 108 | 5 | 49.5 | 184.6 |
| 109 | 5 | 49.5 | 184.6 |

TABLE 3-continued

SNP markers associated with TSS-5.01

| SEQ ID NO. | Chr | MON Map cM | IBM2008 Map IcM |
|---|---|---|---|
| 110 | 5 | 49.5 | 184.6 |
| 111 | 5 | 49.5 | 184.6 |
| 112 | 5 | 49.5 | 184.6 |
| 113 | 5 | 49.6 | 184.8 |
| 114 | 5 | 49.6 | 184.8 |
| 115 | 5 | 49.6 | 184.8 |
| 116 | 5 | 49.6 | 184.8 |
| 117 | 5 | 49.6 | 184.8 |
| 118 | 5 | 49.6 | 184.8 |
| 119 | 5 | 49.6 | 184.8 |
| 120 | 5 | 49.6 | 184.8 |
| 121 | 5 | 49.7 | 185.1 |
| 122 | 5 | 49.7 | 185.1 |
| 123 | 5 | 49.7 | 185.1 |
| 124 | 5 | 49.7 | 185.1 |
| 125 | 5 | 49.7 | 185.1 |

Another QTL associated with the tassel skeletonization trait was mapped to 82.2-116.8 cM on chromosome 3 of a Monsanto internal consensus map and was designated as TSS-3.01. Table 4 lists Monsanto internal SNP markers as well as public markers within the TSS-3.01 region.

TABLE 4

SNP markers associated with TSS-3.01

| Marker | Chromosome | Mon v5.2 (cM) | Neighbors2008 (IcM) |
|---|---|---|---|
| IDP428 | 3 | 82.1 | 225.5 |
| SEQ ID 21 | 3 | 82.2 | 216.8 |
| AY110297 | 3 | 83.8 | 244.7 |
| SEQ ID 3 | 3 | 83.9 | 246.4 |
| csu795 | 3 | 83.9 | 247 |
| phi053 | 3 | 88.9 | 299.6 |
| TIDP3705 | 3 | 93.9 | 322.6 |
| TIDP5268 | 3 | 99.1 | 343 |
| umc2265 | 3 | 103.9 | 354 |
| gpm20 | 3 | 109.1 | 371 |
| IDP4102 | 3 | 114 | 396 |
| IDP7285 | 3 | 115.1 | 399 |
| SEQ ID 27 | 3 | 115.9 | 401.2 |
| umc1027 | 3 | 115.9 | 401.2 |
| agrr271 | 3 | 116.5 | 403.1 |
| SEQ ID 19 | 3 | 116.8 | 404 |
| IDP5975 | 3 | 117.3 | 405.2 |

Example 2

Genome-Wide Association Study (GWAS) of Mapping Population B

Fourteen hundred seventy-five male inbred lines from mapping population B were measured for tassel skeletonization trait on a scale of 0-9, which represents 0%-100% of tassels that were skeletonized on a whole plot basis (Table 5).

TABLE 5

Description of tassel skeletonization rating scale

| Tassel Skeletonization | Score |
|---|---|
| 0-10% | 0 |
| 11-20% | 1 |
| 21-30% | 2 |
| 31-40% | 3 |
| 41-50% | 4 |
| 51-60% | 5 |
| 61-70% | 6 |
| 71-80% | 7 |
| 81-90% | 8 |
| 91-100% | 9 |

Genotyping data was collected from a proprietary database. Each haplotype window covers an approximately 1 cM interval on the Monsanto internal consensus genetic Map. A genome-wide association study was conducted on mapping population B using least absolute shrinkage and selection operator (LASSO) (Li, 2012) and bootstrapping (Visscher, 1996) methods. Table 6 lists top 14 haplotype windows associated with the tassel skeletonization trait identified by GWAS from mapping population B. Each row provides haplotype window ID, chromosome location of the haplotype window, start and end position of the haplotype window, number of SNP markers within the haplotype window, phenotypic variance ($R^2$) explained by the haplotype window, estimated effect of the haplotype window on the tassel skeletonization trait, standard error, t-statistic and p-value corresponding to the t-statistic. Haplotype window e023h0001 that covers the interval of 47.89-49.13 cM on chromosome 5 was identified to be associated with the tassel skeletonization trait. This haplotype window confirmed the TSS-5.01 region identified from mapping population A.

TABLE 6

Top haplotype windows identified by GWAS from mapping population B

| HapID | Chr | stPos | endPos | numMK | $R^2$ | Effect | StdErr | t Stat | p-value |
|---|---|---|---|---|---|---|---|---|---|
| e023h0001 | 5 | 47.89 | 49.13 | 21 | 0.040 | −0.093 | 0.016 | −5.669 | 1.73E−08 |
| e072h0024 | 5 | 114.41 | 115.93 | 29 | 0.028 | 0.149 | 0.055 | 2.714 | 6.73E−03 |
| b055h0002 | 2 | 98.11 | 99.11 | 28 | 0.016 | −0.196 | 0.042 | −4.692 | 2.95E−06 |
| j057h0018 | 10 | 103.85 | 105.31 | 6 | 0.014 | 0.478 | 0.085 | 5.621 | 2.27E−08 |
| e059h0005 | 5 | 97.41 | 98.41 | 62 | 0.013 | 0.114 | 0.024 | 4.777 | 1.96E−06 |
| c083h0012 | 3 | 144.58 | 146.03 | 25 | 0.015 | 0.154 | 0.039 | 3.934 | 8.73E−05 |
| b045h0018 | 2 | 84.15 | 85.2 | 33 | 0.010 | 0.204 | 0.052 | 3.934 | 8.76E−05 |
| e053h0028 | 5 | 88.85 | 90.33 | 210 | 0.010 | 0.363 | 0.098 | 3.694 | 2.29E−04 |
| a070h0031 | 1 | 105.25 | 106.35 | 33 | 0.009 | 0.234 | 0.060 | 3.890 | 1.05E−04 |
| h021h0018 | 8 | 46.05 | 47.36 | 7 | 0.007 | 0.266 | 0.073 | 3.663 | 2.58E−04 |
| b079h0056 | 2 | 121.63 | 123.2 | 33 | 0.006 | 0.263 | 0.078 | 3.389 | 7.21E−04 |
| e105h0005 | 5 | 154.75 | 156.57 | 6 | 0.006 | 0.143 | 0.044 | 3.284 | 1.05E−03 |

TABLE 6-continued

Top haplotype windows identified by GWAS from mapping population B

| HapID | Chr | stPos | endPos | numMK | $R^2$ | Effect | StdErr | t Stat | p-value |
|---|---|---|---|---|---|---|---|---|---|
| g059h0001 | 7 | 104.25 | 105.25 | 10 | 0.005 | 0.263 | 0.085 | 3.080 | 2.11E−03 |
| e018h0014 | 5 | 37.15 | 39.15 | 9 | 0.003 | 0.211 | 0.093 | 2.285 | 2.25E−02 |

Example 3

Validation of TSS-5.01

Five bi-parental populations were developed to evaluate TSS-5.01. Parental lines were selected from non-skeletonizing inbred lines: CV460747, CV707970, and CV319454, and skeletonizing inbred lines: 1208993, CV019026, CV521290, and CV069203 (Table 7). CV460747 is described in U.S. Pat. No. 7,807,893 issued on Oct. 5, 2010. 1208993 is described in U.S. Pat. No. 7,321,087 issued on Jan. 22, 2008. CV707970 is described in U.S. Pat. No. 8,119,880 issued on Feb. 21, 2012. CV521290 is described in U.S. Pat. No. 7,705,220 issued on Apr. 27, 2010. F1 plants derived from CV460747/I208993, CV707970/CV019026, CV707970/CV521290, CV707970/CV069203 and CV019026/CV319454 were self-pollinated to generate F2 seeds. Every individual seed was coded and catalogued. Monsanto's patented seed chipper was used to extract a portion of each seed. The crushed material from the seed chip was analyzed with an automated high-throughput genotyping system and the DNA profile was reconciled with the original seed. F2 seeds homozygous for either favorable or unfavorable alleles at TSS-5.01 region were selected. Favorable alleles were from non-skeletonizing lines and unfavorable alleles from skeletonizing lines as mentioned above. Selected seeds were planted and self-pollinated to generate F3 plants. F3 plants from each population were measured for the tassel skeletonization trait. Both skeletonization intensity and frequency were recorded and used to calculate a tassel skeletonization severity (TSS) scores. TSS score ranges from 0 to 180 with 0 indicating no skeletonization and 180 indicating complete skeletonization. Plants carrying favorable alleles at TSS-5.01 showed a reduction of 16.5-31.9 in TSS score compared to plants carrying unfavorable alleles, depending on the mapping populations (Table 7).

TABLE 7

Validation of TSS-5.01 using bi-parental mapping populations.

| Mapping Population | TSS-5.01 | Number of Lines | Mean (TSS Score) | Efficacy | p-value* |
|---|---|---|---|---|---|
| CV460747/ I208993 | favorable alleles | 43 | 80.9 | 31.9 | 5.60E−11 |
|  | unfavorable alleles | 54 | 112.8 |  |  |
| CV707970/ CV019026 | favorable alleles | 47 | 41.8 | 16.6 | 0.001 |
|  | unfavorable alleles | 46 | 58.4 |  |  |
| CV707970/ CV521290 | favorable alleles | 38 | 46.3 | 20.1 | 7.50E−05 |
|  | unfavorable alleles | 50 | 66.4 |  |  |
| CV707970/ CV069203 | favorable alleles | 45 | 91.4 | 16.5 | 0.004 |
|  | unfavorable alleles | 28 | 107.9 |  |  |
| CV019026/ CV319454 | favorable alleles | 35 | 71.6 | 18.1 | 0.001 |
|  | unfavorable alleles | 41 | 89.7 |  |  |

*p-value was calculated by Student t-test

Table 8 lists primers for amplifying SNP markers mentioned above and the probes used to genotype the corresponding SNP markers. One of skill in the art will recognize that sequences to either side of the given primers can be used in place of the given primers, so long as the primers can amplify a region that includes the allele to be detected. The precise probe used for detection can vary, e.g., any probe that can identify the region of a marker amplicon to be detected can be substituted for those probes exemplified herein. Also, configuration of the amplification primers and detection probes can vary. Thus, the invention is not limited to the primers, probes, or marker sequences specifically recited herein.

TABLE 8

Primers and probes for amplification of SNP markers

| | | SEQ ID NO. | | | |
|---|---|---|---|---|---|
| SEQ ID NO. | SNP Pos. | Fwd Primer | Rev Primer | Probe 1 | Probe 2 |
| 1 | 453 | 126 | 169 | 212 | 255 |
| 2 | 356 | 127 | 170 | 213 | 256 |
| 3 | 1493 | na | na | na | na |
| 4 | 770 | na | na | na | na |
| 5 | 220 | 128 | 171 | 214 | 257 |
| 6 | 237 | 129 | 172 | 215 | 258 |
| 7 | 238 | na | na | na | na |
| 8 | 49 | 130 | 173 | 216 | 259 |
| 9 | 191 | 131 | 174 | 217 | 260 |
| 10 | 66 | 132 | 175 | 218 | 261 |
| 11 | 999 | 133 | 176 | 219 | 262 |
| 12 | 95 | 134 | 177 | 220 | 263 |
| 13 | 316 | 135 | 178 | 221 | 264 |
| 14 | 185 | 136 | 179 | 222 | 265 |
| 15 | 237 | 137 | 180 | 223 | 266 |
| 16 | 248 | 138 | 181 | 224 | 267 |
| 17 | 492 | 139 | 182 | 225 | 268 |
| 18 | 377 | 140 | 183 | 226 | 269 |
| 19 | 1671 | na | na | na | na |
| 20 | 354 | na | na | na | na |
| 21 | 139 | 141 | 184 | 227 | 270 |
| 22 | 408 | 142 | 185 | 228 | 271 |
| 23 | 70 | 143 | 186 | 229 | 272 |
| 24 | 492 | 144 | 187 | 230 | 273 |
| 25 | 108 | 145 | 188 | 231 | 274 |
| 26 | 149 | 146 | 189 | 232 | 275 |
| 27 | 162 | 147 | 190 | 233 | 276 |
| 28 | 393 | na | na | na | na |
| 29 | 392 | 148 | 191 | 234 | 277 |

TABLE 8-continued

Primers and probes for amplification of SNP markers

| SEQ ID NO. | SNP Pos. | Fwd Primer | Rev Primer | Probe 1 | Probe 2 |
|---|---|---|---|---|---|
| 30 | 101 | na | na | na | na |
| 31 | 101 | na | na | na | na |
| 32 | 101 | 149 | 192 | 235 | 278 |
| 33 | 101 | na | na | na | na |
| 34 | 101 | na | na | na | na |
| 35 | 101 | 150 | 193 | 236 | 279 |
| 36 | 155 | 151 | 194 | 237 | 280 |
| 37 | 101 | na | na | na | na |
| 38 | 250 | 152 | 195 | 238 | 281 |
| 39 | 101 | na | na | na | na |
| 40 | 101 | na | na | na | na |
| 41 | 101 | na | na | na | na |
| 42 | 101 | na | na | na | na |
| 43 | 101 | na | na | na | na |
| 44 | 101 | na | na | na | na |
| 45 | 101 | na | na | na | na |
| 46 | 101 | na | na | na | na |
| 47 | 101 | 153 | 196 | 239 | 282 |
| 48 | 591 | na | na | na | na |
| 49 | 650 | 154 | 197 | 240 | 283 |
| 50 | 299 | 155 | 198 | 241 | 284 |
| 51 | 152 | 156 | 199 | 242 | 285 |
| 52 | 101 | na | na | na | na |
| 53 | 101 | na | na | na | na |
| 54 | 101 | na | na | na | na |
| 55 | 101 | na | na | na | na |
| 56 | 101 | na | na | na | na |
| 57 | 101 | na | na | na | na |
| 58 | 101 | na | na | na | na |
| 59 | 101 | na | na | na | na |
| 60 | 101 | na | na | na | na |
| 61 | 101 | 157 | 200 | 243 | 286 |
| 62 | 101 | na | na | na | na |
| 63 | 101 | na | na | na | na |
| 64 | 295 | na | na | na | na |
| 65 | 101 | 158 | 201 | 244 | 287 |
| 66 | 435 | 159 | 202 | 245 | 288 |
| 67 | 180 | 160 | 203 | 246 | 289 |
| 68 | 325 | 161 | 204 | 247 | 290 |
| 69 | 101 | na | na | na | na |
| 70 | 101 | na | na | na | na |
| 71 | 101 | na | na | na | na |
| 72 | 101 | na | na | na | na |
| 73 | 101 | na | na | na | na |
| 74 | 101 | na | na | na | na |
| 75 | 101 | na | na | na | na |
| 76 | 101 | 162 | 205 | 248 | 291 |
| 77 | 101 | na | na | na | na |
| 78 | 101 | na | na | na | na |
| 79 | 101 | na | na | na | na |
| 80 | 101 | na | na | na | na |
| 81 | 101 | na | na | na | na |
| 82 | 221 | 163 | 206 | 249 | 292 |
| 83 | 101 | na | na | na | na |
| 84 | 101 | na | na | na | na |
| 85 | 101 | na | na | na | na |
| 86 | 101 | na | na | na | na |
| 87 | 101 | na | na | na | na |
| 88 | 101 | na | na | na | na |
| 89 | 101 | na | na | na | na |
| 90 | 101 | na | na | na | na |
| 91 | 168 | 164 | 207 | 250 | 293 |
| 92 | 226 | 165 | 208 | 251 | 294 |
| 93 | 953 | na | na | na | na |
| 94 | 101 | na | na | na | na |
| 95 | 101 | 166 | 209 | 252 | 295 |
| 96 | 101 | na | na | na | na |
| 97 | 101 | na | na | na | na |
| 98 | 101 | na | na | na | na |
| 99 | 101 | na | na | na | na |
| 100 | 101 | na | na | na | na |
| 101 | 101 | na | na | na | na |
| 102 | 101 | na | na | na | na |
| 103 | 101 | na | na | na | na |
| 104 | 101 | na | na | na | na |
| 105 | 101 | na | na | na | na |
| 106 | 101 | na | na | na | na |
| 107 | 101 | na | na | na | na |
| 108 | 101 | na | na | na | na |
| 109 | 101 | na | na | na | na |
| 110 | 101 | na | na | na | na |
| 111 | 101 | na | na | na | na |
| 112 | 101 | na | na | na | na |
| 113 | 101 | na | na | na | na |
| 114 | 101 | na | na | na | na |
| 115 | 101 | na | na | na | na |
| 116 | 101 | na | na | na | na |
| 117 | 101 | 167 | 210 | 253 | 296 |
| 118 | 101 | na | na | na | na |
| 119 | 101 | na | na | na | na |
| 120 | 101 | na | na | na | na |
| 121 | 104 | 168 | 211 | 254 | 297 |
| 122 | 101 | na | na | na | na |
| 123 | 101 | na | na | na | na |
| 124 | 101 | na | na | na | na |
| 125 | 101 | na | na | na | na |

Example 4

Candidate Genes within TSS-5.01 Region

Table 9 lists annotated coding sequences within TSS-5.01 region. Each row provides gene ID, gene annotation, chromosome location, genetic position on Monsanto internal consensus map and physical position based on Arizona Genomics Institute B73 RefGen v2 sequence which is publicly available. Transgenic maize with reduced tassel skeletonization and increased yield can be created using these annotated genes as described in the specification.

TABLE 9

Candidate genes within TSS-5.01 interval

| Gene | | | MON | Physical Map Position bp ‡ | |
|---|---|---|---|---|---|
| ID | Annotation | Chr | Map cM † | Start | End |
| 1 | ATP binding protein, putative n = 1 Tax = Ricinus communis RepID = B9SNW7_RICCO (0.0); Pkinase: Protein kinase domain (6.7e–40); Pkinase_Tyr: Protein tyrosine kinase (1.1e–07); Abhydrolase_1: alpha/beta hydrolase fold (4.2e–08); | 5 | 40.05 | 10068082 | 10092446 |

TABLE 9-continued

Candidate genes within TSS-5.01 interval

| Gene ID | Annotation | Chr | MON Map cM † | Physical Map Position bp ‡ Start | End |
|---|---|---|---|---|---|
|  | Dak2: DAK2 domain (6.8e−05); GO_MF:GO:0016301, kinase activity# (0.0); GO_BP:GO:0016301, kinase activity# (0.0); GO_CC:GO:0005886, plasma membrane# (0.0) |  |  |  |  |
| 2 | ATP binding protein, putative n = 1 Tax = Ricinus communis RepID = B9SBX9_RICCO (3e−36); Fip1: Fip1 motif (2.8e−28); GO_MF:GO:0043565, sequence-specific DNA binding# (3e−35); GO_BP:GO:0045449, regulation of transcription# (3e−35); GO_CC:GO:0030288, outer membrane-bounded periplasmic space# (3e−35) | 5 | 40.1 | 9693335 | 9697701 |
| 3 | Putative uncharacterized protein n = 1 Tax = Zea mays RepID = C4J310_MAIZE (8e−24) | 5 | 40.1 | 9997630 | 9997839 |
| 4 | Uncharacterized conserved protein of probably eukaryotic origin n = 1 Tax = Clostridium acetobutylicum RepID = Q97KX3_CLOAB (6e−15); DUF946: Plant protein of unknown function (DUF946) (0); NPP1: Necrosis inducing protein (NPP1) (0.0092); GO_MF:GO:0005488, binding# (1e−140); GO_BP:GO:0006396, RNA processing# (1e−140); GO_CC:GO:0005622, intracellular# (1e−140) | 5 | 40.1 | 10009746 | 10012284 |
| 5 | Phytochrome a n = 19 Tax = Andropogoneae RepID = PHYA_SORBI (0.0); PAS_2: PAS fold (2.1e−66); GAF: GAF domain (6.2e−29); Phytochrome: Phytochrome region (1.2e−119); PAS: PAS domain (6.6e−25); PAS_4: PAS fold (0.0033); PAS: PAS domain (3.7e−27); HisKA: His Kinase A (phosphoacceptor) domain (4.9e−05); HATPase_c: Histidine kinase-, DNA gyrase B-, and HSP90-like ATPase (6e−17); GO_MF:GO:0042803, protein homodimerization activity# (0.0); GO_BP:GO:0050896, response to stimulus# (0.0); GO_CC:GO:0016020, membrane# (0.0) | 5 | 40.15 | 10101025 | 10106762 |
| 6 | Transmembrane and coiled-coil domains protein, putative n = 1 Tax = Ricinus communis RepID = B9SWJ7_RICCO (2e−54); DUF841: Eukaryotic protein of unknown function (DUF841) (1.8e−88); GO_CC:GO:0016021, integral to membrane# (2e−54) | 5 | 40.15 | 9994193 | 9998117 |
| 7 | Histone H2A n = 1 Tax = Sorghum bicolor RepID = C5WMX3_SORBI (2e−59); Histone: Core histone H2A/H2B/H3/H4 (1.9e−30); CBFD_NFYB_HMF: Histone-like transcription factor (CBF/NF-Y) and archaeal histone (0.0039); GO_MF:GO:0003677, DNA binding# (3e−49); GO_BP:GO:0006334, nucleosome assembly# (3e−49); GO_CC:GO:0005694, chromosome# (3e−49) | 5 | 40.2 | 9951622 | 9952597 |
| 8 | OSJNBa0059D20.8 protein n = 1 Tax = Oryza sativa Japonica Group RepID = Q7XSK7_ORYSJ (2e−67); GO_MF:GO:0003964, RNA-directed DNA polymerase, group II intron encoded# (2e−67); GO_BP:GO:0015074, DNA integration# (2e−67); GO_CC:GO:0005634, nucleus# (2e−67) | 5 | 40.2 | 9952665 | 9953574 |
| 9 | Phosphoprotein phosphatase, putative n = 1 Tax = Ricinus communis RepID = B9T6R5_RICCO (4e−77); GO_MF:GO:0016791, phosphatase activity# (3e−79); GO_BP:GO:0016791, phosphatase activity# (3e−79); GO_CC:GO:0005829, IDA#cytosol# (7e−36) | 5 | 40.2 | 9956253 | 9973761 |
| 10 | Putative receptor-like kinase n = 2 Tax = Oryza sativa RepID = Q9LDG0_ORYSJ (1e−53); LRR_1: Leucine Rich Repeat (2); LRR_1: Leucine Rich Repeat (0.58); LRR_1: Leucine Rich Repeat (1.6); GO_MF:GO:0005524, ATP binding# (1e−64); GO_BP:GO:0006468, protein amino acid phosphorylation# (1e−64); GO_CC:GO:0016021, integral to membrane# (9e−40) | 5 | 40.2 | 9984935 | 9986217 |
| 11 | Putative uncharacterized protein n = 1 Tax = Zea mays RepID = C0PE57_MAIZE (6e−61) | 5 | 40.2 | 9974493 | 9975161 |

TABLE 9-continued

Candidate genes within TSS-5.01 interval

| Gene ID | Annotation | Chr | MON Map cM † | Physical Map Position bp ‡ Start | End |
|---|---|---|---|---|---|
| 12 | Putative uncharacterized protein Sb02g010670 n = 1 Tax = *Sorghum bicolor* RepID = C5X534_SORBI (5e-48) | 5 | 40.2 | 9977355 | 9978566 |
| 13 | Putative gag-pol polyprotein n = 1 Tax = *Zea mays* RepID = Q8H6I8_MAIZE (0.0); zf-CCHC: Zinc knuckle (5.2e-06); rve: Integrase core domain (6.8e-56); RVT_2: Reverse transcriptase (RNA-dependent DNA pol (1.2e-159); GO_MF:GO:0003677, DNA binding# (0.0); GO_BP:GO:0015074, DNA integration# (0.0) | 5 | 40.25 | 9935294 | 9940907 |
| 14 | Adenylyl cyclase-associated protein n = 1 Tax = *Oryza sativa Japonica* Group RepID = Q53K24_ORYSJ (0.0); CAP_N: Adenylate cyclase associated (CAP) N (8.6e-53); CAP_C: DE Adenylate cyclase associated (CA (3.4e-91); GO_MF:GO:0005488, binding# (0.0); GO_BP:GO:0007010, cytoskeleton organization# (0.0); GO_CC:GO:0016020, membrane# (1e-53) | 5 | 40.3 | 9900749 | 9908246 |
| 15 | Glucan endo-1,3-beta-glucosidase 7 n = 2 Tax = Andropogoneae RepID = B6TU78_MAIZE (0.0); Glyco_hydro_17: Glycosyl hydrolases family 17 (3.6e-100); GO_MF:GO:0043169, cation binding# (0.0); GO_BP:GO:0008152, metabolic process# (0.0); GO_CC:GO:0031225, TAS#anchored to membrane# (5e-96) | 5 | 40.3 | 9908659 | 9910966 |
| 16 | Putative uncharacterized protein n = 1 Tax = *Zea mays* RepID = C0PPA5_MAIZE (5e-19) | 5 | 40.3 | 9934436 | 9934765 |
| 17 | Serine/threonine-protein kinase PBS1, putative n = 1 Tax = *Ricinus communis* RepID = B9T805_RICCO (1e-125); Pkinase_Tyr: Protein tyrosine kinase (3e-29); Pkinase: Protein kinase domain (6.4e-14); GO_MF:GO:0016301, kinase activity# (1e-151); GO_BP:GO:0016301, kinase activity# (1e-151); GO_CC:GO:0005886, plasma membrane# (1e-113) | 5 | 40.3 | 10117318 | 10118913 |
| 18 | Cell cycle control protein cwf22, putative n = 1 Tax = *Ricinus communis* RepID = B9SWX3_RICCO (6e-98); MIF4G: MIF4G domain (0.0088); MA3: MA3 domain (1.7e-23); GO_MF:GO:0005515, protein binding# (1e-119); GO_BP:GO:0016070, TAS#RNA metabolic process# (1e-119); GO_CC:GO:0016020, membrane# (1e-116) | 5 | 40.4 | 9860685 | 9865219 |
| 19 | Putative uncharacterized protein n = 1 Tax = *Zea mays* RepID = C0PNA0_MAIZE (2e-62) | 5 | 40.4 | 9860115 | 9860633 |
| 20 | Chitin-inducible gibberellin-responsive protein, putative n = 1 Tax = *Ricinus communis* RepID = B9S6I2_RICCO (1e-109); GRAS: GRAS family transcription factor (6.6e-133); GO_MF:GO:0005515, protein binding# (1e-103); GO_BP:GO:0045449, regulation of transcription# (1e-161); GO_CC:GO:0005634, nucleus# (1e-103) | 5 | 40.5 | 9817191 | 9819010 |
| 21 | Protein binding protein, putative n = 1 Tax = *Ricinus communis* RepID = B9RBE9_RICCO (9e-92); GO_MF:GO:0005515, protein binding# (1e-15) | 5 | 40.5 | 9801937 | 9807531 |
| 22 | Putative uncharacterized protein Sb01g009730 n = 1 Tax = *Sorghum bicolor* RepID = C5WMW4_SORBI (2e-44) | 5 | 40.5 | 9811984 | 9813019 |
| 23 | ATP binding protein, putative n = 1 Tax = *Ricinus communis* RepID = B9SBX9_RICCO (5e-33); GO_MF:GO:0043565, sequence-specific DNA binding# (2e-35); GO_BP:GO:0045449, regulation of transcription# (2e-35); GO_CC:GO:0030288, outer membrane-bounded periplasmic space# (2e-35) | 5 | 40.55 | 9709464 | 9713942 |
| 24 | Putative uncharacterized protein Sb01g009700 n = 1 Tax = *Sorghum bicolor* RepID = C5WM42_SORBI (1e-19) | 5 | 40.6 | 9736294 | 9736889 |
| 25 | Putative uncharacterized protein Sb03g017640 n = 1 Tax = *Sorghum bicolor* RepID = C5XLA7_SORBI (1e-12) | 5 | 40.6 | 9730795 | 9731727 |
| 26 | UDP-sugar pyrophosphorylase n = 1 Tax = *Zea mays* RepID = B6UC67_MAIZE (1e-126); GO_MF:GO:0016779, nucleotidyltransferase activity# (1e-126); GO_BP:GO:0008152, metabolic process# (1e-126) | 5 | 40.6 | 9754271 | 9757706 |

TABLE 9-continued

Candidate genes within TSS-5.01 interval

| Gene ID | Annotation | Chr | MON Map cM † | Physical Map Position bp ‡ Start | End |
|---|---|---|---|---|---|
| 27 | MYB transcription factor n = 1 Tax = *Populus trichocarpa* RepID = B9I4W4_POPTR (2e−64); Myb_DNA-binding: Myb-like DNA-binding domain (3.1e−13); Myb_DNA-binding: Myb-like DNA-binding domain (1.1e−10); GO_MF:GO:0003677, DNA binding# (3e−92); GO_BP:GO:0045449, regulation of transcription# (3e−92); GO_CC:GO:0005634, nucleus# (3e−92) | 5 | 40.7 | 10172918 | 10174723 |
| 28 | Putative transposase n = 1 Tax = *Zea mays* RepID = Q8W0Y1_MAIZE (3e−60) | 5 | 40.7 | 10169103 | 10170392 |
| 29 | Putative uncharacterized protein n = 1 Tax = *Zea mays* RepID = C0PHM9_MAIZE (0.0); DUF760: Protein of unknown function (DUF760) (1.3e−177); GO_BP:GO:0010224, response to UV-B# (1e−108); GO_CC:GO:0009507, chloroplast# (7e−69) | 5 | 40.95 | 10230211 | 10233230 |
| 30 | Putative uncharacterized protein Sb01g009990 n = 1 Tax = *Sorghum bicolor* RepID = C5WMZ5_SORBI (3e−12) | 5 | 41 | 10206930 | 10207211 |
| 31 | ZF-HD protein dimerisation region containing protein n = 1 Tax = *Zea mays* RepID = B6U3R0_MAIZE (5e−71); ZF-HD_dimer: ZF-HD protein dimerisation region (8e−24); GO_MF:GO:0003677, DNA binding# (5e−71); GO_BP:GO:0045449, regulation of transcription# (5e−71); GO_CC:GO:0005634, nucleus# (1e−25) | 5 | 41 | 10212826 | 10214020 |
| 32 | 14-3-3-like protein GF14-6 n = 1 Tax = *Zea mays* RepID = B6TJT5_MAIZE (7e−30); GO_MF:GO:0019904, TAS#protein domain specific binding# (4e−64); GO_BP:GO:0006950, response to stress# (2e−25); GO_CC:GO:0005737, cytoplasm# (2e−29) | 5 | 41.2 | 10863898 | 10866507 |
| 33 | DNA binding protein, putative n = 1 Tax = *Ricinus communis* RepID = B9T5F9_RICCO (1e−116); PHD: PHD-finger (1.5e−09); GO_MF:GO:0046872, metal ion binding# (0.0); GO_CC:GO:0005634, nucleus# (1e−115) | 5 | 41.2 | 10436880 | 10440158 |
| 34 | DNA polymerase n = 1 Tax = *Ricinus communis* RepID = B9RF68_RICCO (3e−57); zf-RanBP: Zn-finger in Ran binding protein and others (8.9e−07); zf-RanBP: Zn-finger in Ran binding protein and others (0.0023); GO_MF:GO:0008270, zinc ion binding# (0.0); GO_BP:GO:0006260, DNA replication# (3e−57); GO_CC:GO:0005622, intracellular# (0.0) | 5 | 41.2 | 10939312 | 10955302 |
| 35 | Phosphoglucomutase, cytoplasmic 1 n = 11 Tax = Poaceae RepID = PGMC1_MAIZE (0.0); PGM_PMM_I: Phosphoglucomutase/phosphomannomutase, alpha/beta/alpha domain I (1.1e−48); PGM_PMM_II: Phosphoglucomutase/phosphomannomutase, alpha/beta/alpha domain II (1.4e−27); PGM_PMM_III: Phosphoglucomutase/phosphomannomutase, alpha/beta/alpha domain III (1.8e−35); PGM_PMM_IV: Phosphoglucomutase/phosphomannomutase (3.6e−18); GO_MF:GO:0046872, metal ion binding# (0.0); GO_BP:GO:0006006, glucose metabolic process# (0.0); GO_CC:GO:0005737, cytoplasm# (0.0) | 5 | 41.2 | 10855533 | 10861596 |
| 36 | Putative DNA-binding protein n = 1 Tax = *Oryza sativa* RepID = Q9AUQ8_ORYSA (2e−75); UQ_con: Ubiquitin-conjugating enzyme (7.9e−07); GO_MF:GO:0019787, small conjugating protein ligase activity# (2e−80); GO_BP:GO:0051246, regulation of protein metabolic process# (2e−80); GO_CC:GO:0031372, UBC13-MMS2 complex# (4e−60) | 5 | 41.2 | 10931403 | 10937042 |
| 37 | Putative uncharacterized protein n = 1 Tax = *Zea mays* RepID = C0PF44_MAIZE (4e−18) | 5 | 41.2 | 10935268 | 10936075 |
| 38 | Kinase, putative n = 1 Tax = *Ricinus communis* RepID = B9T5A7_RICCO (0.0); Pkinase_Tyr: | 5 | 41.3 | 10971701 | 10991464 |

TABLE 9-continued

Candidate genes within TSS-5.01 interval

| Gene ID | Annotation | MON Chr | Map cM † | Physical Map Position bp ‡ Start | End |
|---|---|---|---|---|---|
| | Protein tyrosine kinase (4.6e−15); Pkinase: Protein kinase domain (3e−83); APH: Phosphotransferase enzyme family (0.0027); GO_MF:GO:0016740, transferase activity# (0.0); GO_BP:GO:0016301, kinase activity# (0.0); GO_CC:GO:0005694, chromosome# (0.0) | | | | |
| 39 | Retrotransposon protein, putative, unclassified n = 1 Tax = *Oryza sativa Japonica* Group RepID = Q2R1H4_ORYSJ (5e−23); GO_MF:GO:0003677, DNA binding# (3e−21); GO_BP:GO:0015074, DNA integration# (3e−21) | 5 | 41.3 | 10959093 | 10959613 |
| 40 | Atypical receptor-like kinase MARK n = 1 Tax = *Zea mays* RepID = B6U2I0_MAIZE (0.0); LRRNT_2: Leucine rich repeat N-terminal domain (4.3e−08); LRR_1: Leucine Rich Repeat (25); LRR_1: Leucine Rich Repeat (11); LRR_1: Leucine Rich Repeat (15); LRR_1: Leucine Rich Repeat (0.72); LRR_1: Leucine Rich Repeat (5.4); LRR_1: Leucine Rich Repeat (23); Pkinase_Tyr: Protein tyrosine kinase (6e−16); Pkinase: Protein kinase domain (1.4e−21); GO_MF:GO:0016301, kinase activity# (0.0); GO_BP:GO:0016301, kinase activity# (0.0); GO_CC:GO:0016021, integral to membrane# (1e−115) | 5 | 41.4 | 10897518 | 10900786 |
| 41 | Coatomer subunit alpha-1 n = 6 Tax = *Oryza sativa* RepID = COPA1_ORYSJ (0.0); WD40: WD domain, G-beta repeat (14); WD40: WD domain, G-beta repeat (6.6e−09); WD40: WD domain, G-beta repeat (5.1e−11); WD40: WD domain, G-beta repeat (2.2e−12); WD40: WD domain, G-beta repeat (1.6e−08); WD40: WD domain, G-beta repeat (9.4e−08); Coatomer_WDAD: Coalomer WD associated region (1.6e−265); COPI_C: Coalomer (COPI) alpha subunit C-terminu (2.9e−284); GO_MF:GO:0005515, protein binding# (0.0); GO_BP:GO:0016192, vesicle-mediated transport# (0.0); GO_CC:GO:0031410, IDA#cytoplasmic vesicle# (0.0) | 5 | 41.5 | 11087383 | 11092296 |
| 42 | Phosphatase n = 1 Tax = *Zea mays* RepID = B4FL38_MAIZE (1e−27); GO_MF:GO:0016787, hydrolase activity# (6e−20); GO_BP:GO:0008152, metabolic process# (4e−12) | 5 | 41.5 | 10399473 | 10400617 |
| 43 | Putative uncharacterized protein n = 1 Tax = *Zea mays* RepID = C0PG45_MAIZE (2e−21); Linker_histone: linker histone H1 and H5 family (1.7e−06); AT_hook: AT hook motif (1.3); AT_hook: AT hook motif (4.2); AT_hook: AT hook motif (0.14); GO_MF:GO:0016740, transferase activity# (2e−21); GO_BP:GO:0016301, kinase activity# (2e−21); GO_CC:GO:0005694, chromosome# (2e−21) | 5 | 41.5 | 11053076 | 11085439 |
| 44 | Receptor protein kinase, putative n = 1 Tax = *Ricinus communis* RepID = B9SNG9_RICCO (0.0); LRRNT_2: Leucine rich repeat N-terminal domain (2.7e−05); LRR_1: Leucine Rich Repeat (2); LRR_1: Leucine Rich Repeat (3.3); LRR_1: Leucine Rich Repeat (3.8); LRR_1: Leucine Rich Repeat (1.7e+02); LRR_1: Leucine Rich Repeat (2.7); LRR_1: Leucine Rich Repeat (5.3); LRR_1: Leucine Rich Repeat (64); LRRNT_2: Leucine rich repeat N-terminal domain (0.1); LRR_1: Leucine Rich Repeat (1.6e+02); LRR_1: Leucine Rich Repeat (0.15); LRR_1: Leucine Rich Repeat (5.3); Pkinase_Tyr: Protein tyrosine kinase (1.1e−30); Pkinase: Protein kinase domain (3.6e−45); APH: Phosphotransferase enzyme family (0.013); GO_MF:GO:0016301, kinase activity# (0.0); GO_BP:GO:0016301, kinase activity# (0.0); GO_CC:GO:0016021, integral to membrane# (0.0) | 5 | 41.5 | 10414619 | 10418698 |
| 45 | Protein kinase domain containing protein n = 1 Tax = *Oryza sativa Japonica* Group RepID = Q8W318_ORYSJ (4e−94); Pkinase: Protein kinase domain (6.1e−54); Pkinase_Tyr: Protein tyrosine kinase (2.2e−12); APH: Phosphotransferase enzyme family (0.077); GO_MF:GO:0005524, ATP | 5 | 41.6 | 10497391 | 10498371 |

TABLE 9-continued

Candidate genes within TSS-5.01 interval

| Gene ID | Annotation | Chr | MON Map cM † | Physical Map Position bp ‡ Start | End |
|---|---|---|---|---|---|
| | binding# (1e-102); GO_BP:GO:0006468, protein amino acid phosphorylation# (1e-102); GO_CC:GO:0005737, cytoplasm# (3e-49) | | | | |
| 46 | Putative ATP(GTP)-binding protein n = 1 Tax = *Oryza sativa Japonica* Group RepID = Q8W326_ORYSJ (1e-111); ATP_bind_1: Conserved hypothetical ATP binding pro (1.1e-75); GO_MF:GO:0000166, nucleotide binding# (1e-111); GO_CC:GO:0005829, IDA#cytosol# (4e-55) | 5 | 41.8 | 10583916 | 10588381 |
| 47 | Putative dehydratase/deaminase n = 2 Tax = *Oryza sativa* RepID = Q8W314_ORYSJ (1e-16); GO_MF:GO:0030170, pyridoxal phosphate binding# (1e-16); GO_BP:GO:0009097, isoleucine biosynthetic process# (1e-16); GO_CC:GO:0009536, plastid# (2e-13) | 5 | 41.8 | 10808117 | 10808819 |
| 48 | RNA recognition motif containing protein n = 4 Tax = Andropogoneae RepID = B6TAS2_MAIZE (1e-155); RRM_1: RNA recognition motif. (a.k.a. RRM, RB (0.003); GO_MF:GO:0016491, oxidoreductase activity# (1e-155); GO_BP:GO:0055114, oxidation reduction# (1e-155) | 5 | 41.8 | 10541907 | 10545884 |
| 49 | Protein kinase domain containing protein n = 1 Tax = *Oryza sativa Japonica* Group RepID = Q8W318_ORYSJ (1e-113); Pkinase: Protein kinase domain (2.4e-57); Pkinase_Tyr: Protein tyrosine kinase (2.3e-12); GO_MF:GO:0005524, ATP binding# (1e-119); GO_BP:GO:0006468, protein amino acid phosphorylation# (1e-119); GO_CC:GO:0005737, cytoplasm# (5e-59) | 5 | 41.9 | 10708460 | 10709572 |
| 50 | Protein TAPT1 homolog n = 1 Tax = *Dictyostelium discoideum* RepID = TAPT1_DICDI (2e-43); DUF747: Eukaryotic membrane protein (cytomegalovirus gH-receptor) family (8.4e-154); GO_MF:GO:0016520, IDA#growth hormone-releasing hormone receptor activity# (4e-38); GO_BP:GO:0009792, IMP#embryonic development ending in birth or egg hatching# (2e-39); GO_CC:GO:0016021, integral to membrane# (2e-43) | 5 | 41.9 | 10674249 | 10681795 |
| 51 | Putative dehydratase/deaminase n = 2 Tax = *Oryza sativa* RepID = Q8W314_ORYSJ (0.0); PALP: Pyridoxal-phosphate dependent enzyme (3.7e-33); Thr_dehydrat_C: C-terminal regulatory domain of Threonine dehydratase (7.2e-22); Thr_dehydrat_C: C-terminal regulatory domain of Threonine dehydratase (6.8e-05); GO_MF:GO:0030170, pyridoxal phosphate binding# (0.0); GO_BP:GO:0009097, isoleucine biosynthetic process# (0.0); GO_CC:GO:0009536, plastid# (1e-155) | 5 | 41.9 | 10796859 | 10800534 |
| 52 | TGF beta receptor associated protein-like protein n = 1 Tax = *Oryza sativa Japonica* Group RepID = Q8W338_ORYSJ (9e-11); GO_MF:GO:0005488, binding# (5e-11); GO_BP:GO:0005083, small GTPase regulator activity# (5e-11) | 5 | 41.9 | 10704583 | 10704892 |
| 53 | Dynamin, putative n = 1 Tax = *Ricinus communis* RepID = B9SS14_RICCO (0.0); MMR_HSR1: GTPase of unknown function (0.00088); Dynamin_N: Dynamin family (3.5e-87); Dynamin_M: Dynamin central region (8.6e-78); GED: Dynamin GTPase effector domain (2e-33); GO_MF:GO:0005525, GTP binding# (0.0); GO_BP:GO:0051301, cell division# (0.0); GO_CC:GO:0016020, membrane# (0.0) | 5 | 41.95 | 10786474 | 10794509 |
| 54 | NADH-ubiquinone oxidoreductase 75 kDa subunit n = 6 Tax = Poaceae RepID = Q8W317_ORYSJ (0.0); Fer2: 2Fe—2S iron-sulfur cluster binding do (7.6e-12); NADH-G_4Fe—4S_3: NADH-ubiquinone oxidoreductase-G iron (5.4e-22); Molybdopterin: Molybdopterin oxidoreductase (2.9e-135); DUF1982: Domain of unknown function | 5 | 42 | 10781545 | 10785355 |

TABLE 9-continued

Candidate genes within TSS-5.01 interval

| Gene ID | Annotation | Chr | MON Map cM † | Physical Map Position bp ‡ Start | End |
|---|---|---|---|---|---|
| | (DUF1982) (7.3e−20); GO_MF:GO:0051539, 4 iron, 4 sulfur cluster binding# (0.0); GO_BP:GO:0055114, oxidation reduction# (0.0); GO_CC:GO:0016020, membrane# (0.0) | | | | |
| 55 | Pupative polyprotein n = 1 Tax = *Oryza sativa Japonica* Group RepID = Q75IL9_ORYSJ (0.0); rve: Integrase core domain (0.0028); RVT_2: Reverse transcriptase (RNA-dependent DNA pol (9.9e−120); GO_MF:GO:0008270, zinc ion binding# (0.0); GO_BP:GO:0015074, DNA integration# (0.0) | 5 | 42 | 10268308 | 10270413 |
| 56 | Pupative polyprotein n = 1 Tax = *Oryza sativa Japonica* Group RepID = Q75IL9_ORYSJ (1e−151); zf-CCHC: Zinc knuckle (2.8e−07); GO_MF:GO:0008270, zinc ion binding# (1e−151); GO_BP:GO:0015074, DNA integration# (1e−151) | 5 | 42.05 | 10270462 | 10272021 |
| 57 | Phosphatidylinositol 3-and 4-kinase, putative n = 1 Tax = *Oryza sativa Japonica* Group RepID = Q53RI7_ORYSJ (0.0); PI3Ka: Phosphoinositide 3-kinase family, accessory domain (PIK domain) (3.5e−10); PI3_PI4_kinase: Phosphatidylinositol 3- and 4-kinase (1.5e−42); GO_MF:GO:0016773, phosphotransferase activity, alcohol group as acceptor# (0.0); GO_BP:GO:0048015, phosphoinositide-mediated signaling# (0.0); GO_CC:GO:0005886, plasma membrane# (0.0) | 5 | 42.15 | 11344621 | 11371761 |
| 58 | CASP C terminal, putative n = 1 Tax = *Oryza sativa Japonica* Group RepID = Q53RI9_ORYSJ (0.0); CtIP_N: Tumour-suppressor protein CtIP N-term (0.082); CASP_C: CASP C terminal (9.8e−102); GO_MF:GO:0043565, sequence-specific DNA binding# (8e−32); GO_BP:GO:0006891, intra-Golgi vesicle-mediated transport# (0.0); GO_CC:GO:0030173, integral to Golgi membrane# (0.0) | 5 | 42.2 | 11394624 | 11404845 |
| 59 | CCT motif family protein n = 1 Tax = *Zea mays* RepID = B6TFB2_MAIZE (0.0); zf_B_box: B-box zinc finger (5.6e−09); CCT: CCT motif (2.2e−22); GO_MF:GO:0008270, zinc ion binding# (0.0); GO_BP:GO:0045449, regulation of transcription# (3e−45); GO_CC:GO:0005622, intracellular# (0.0) | 5 | 42.2 | 11373302 | 11375135 |
| 60 | CG6282, isoform A n = 4 Tax = *Sophophora* RepID = Q9VSM5_DROME (7e−63); DUF1295: Protein of unknown function (DUF1295) (6.5e−130); GO_MF:GO:0016627, oxidoreductase activity, acting on the CH—CH group of donors# (1e−146); GO_BP:GO:0006629, lipid metabolic process# (1e−146); GO_CC:GO:0016021, integral to membrane# (1e−146) | 5 | 42.2 | 11691037 | 11695508 |
| 61 | Chemocyanin n = 2 Tax = *Zea mays* RepID = B6SNZ1_MAIZE (3e−53); Copper-bind: Copper binding proteins, plastocyanin/az (0.00048); Cu_bind_like: Plastocyanin-like domain (5.1e−38); GO_MF:GO:0009055, electron carrier activity# (3e−53); GO_BP:GO:0048653, IGI#anther development# (9e−31); GO_CC:GO:0048196, IDA#middle lamella-containing extracellular matrix# (9e−31) | 5 | 42.2 | 11490317 | 11491310 |
| 62 | DEAD-box ATP-dependent RNA helicase 21 n = 6 Tax = Poaceae RepID = RH21_ORYSJ (0.0); DUF1777: Protein of unknown function (DUF1777) (0.035); DEAD: DEAD/DEAR box helicase (1.7e−66); Helicase_C: Helicase conserved C-terminal domain (2.6e−35); GO_MF:GO:0016787, hydrolase activity# (0.0); GO_BP:GO:0008380, RNA splicing# (0.0); GO_CC:GO:0005737, cytoplasm# (0.0) | 5 | 42.2 | 11603264 | 11606179 |
| 63 | FK506 binding protein n = 2 Tax = Andropogoneae RepID = B6TP21_MAIZE (1e−102); FKBP_C: FKBP-type peptidyl-prolyl cis-trans isomeras (1.9e−16); GO_MF:GO:0016853, isomerase activity# (1e−102); | 5 | 42.2 | 11689434 | 11690888 |

TABLE 9-continued

Candidate genes within TSS-5.01 interval

| Gene ID | Annotation | Chr | MON Map cM † | Physical Map Position bp ‡ Start | End |
|---|---|---|---|---|---|
| | GO_BP:GO:0006457, protein folding# (1e−102); GO_CC:GO:0009579, thylakoid# (1e−64) | | | | |
| 64 | Histidine kinase n = 4 Tax = Andropogoneae RepID = Q2ACB8_MAIZE (0.0); CHASE: CHASE domain (1.2e−85); HisKA: His Kinase A (phosphoacceptor) domain (2.3e−23); HATPase_c: Histidine kinase-, DNA gyrase B-, and HSP90-like ATPase (3e−36); Response_reg: Response regulator receiver domain (8.6e−26); GO_MF:GO:0016772, transferase activity, transferring phosphorus-containing groups# (0.0); GO_BP:GO:0018106, peptidyl-histidine phosphorylation# (0.0); GO_CC:GO:0016020, membrane# (0.0) | 5 | 42.2 | 10272839 | 10280981 |
| 65 | IFA binding protein n = 1 Tax = *Lilium longiflorum* RepID = A6MGY3_LILLO (3e−24); DUF593: Protein of unknown function, DUF593 (2.3e−49); GO_MF:GO:0003677, DNA binding# (1e−16); GO_BP:GO:0006334, nucleosome assembly# (1e−16); GO_CC:GO:0000786, nucleosome# (1e−16) | 5 | 42.2 | 11596339 | 11600967 |
| 66 | OSIGBa0130K07.2 protein n = 1 Tax = *Oryza sativa* RepID = Q01LK5_ORYSA (1e−17); GLTP: Glycolipid transfer protein (GLTP) (1.6e−29); GO_MF:GO:0051861, glycolipid binding# (2e−94); GO_BP:GO:0046836, glycolipid transport# (2e−94); GO_CC:GO:0005737, cytoplasm# (2e−94) | 5 | 42.2 | 11390627 | 11392718 |
| 67 | Pairing protein meu13-like n = 1 Tax = *Zea mays* RepID = B6TAH2_MAIZE (1e−115); TBPIP: Tat binding protein 1(TBP-1)-interact (2.5e−42); GO_MF:GO:0050681, androgen receptor binding# (2e−25); GO_BP:GO:0007126, IMP#meiosis# (2e−75); GO_CC:GO:0005634, nucleus# (2e−75) | 5 | 42.2 | 11484823 | 11487089 |
| 68 | Putative non-LTR retroelement reverse transcriptase n = 1 Tax = *Sorghum bicolor* RepID = Q1KSC2_SORBI (1e−34); GO_MF:GO:0008270, zinc ion binding# (1e−35); GO_BP:GO:0006278, RNA-dependent DNA replication# (1e−34) | 5 | 42.2 | 11687782 | 11689009 |
| 69 | Putative uncharacterized protein Sb01g010450 n = 4 Tax = Andropogoneae RepID = C5WN46_SORBI (3e−62); GO_CC:GO:0009535, chloroplast thylakoid membrane# (5e−20) | 5 | 42.2 | 11455599 | 11457174 |
| 70 | Retrotransposon protein, putative, unclassified n = 2 Tax = *Oryza sativa Japonica* Group RepID = Q10HY9_ORYSJ (6e−24); GO_MF:GO:0008270, zinc ion binding# (6e−26); GO_BP:GO:0006278, RNA-dependent DNA replication# (6e−24) | 5 | 42.2 | 11377623 | 11381203 |
| 71 | Transcription regulator, putative n = 1 Tax = *Ricinus communis* RepID = B9SYW7_RICCO (5e−18); DUF573: Protein of unknown function, DUF573 (7.3e−08) | 5 | 42.2 | 11590629 | 11592307 |
| 72 | Zn-finger in Ran binding protein and others, putative n = 1 Tax = *Oryza sativa Japonica* Group RepID = Q53RK2_ORYSJ (1e−110); zf-RanBP: Zn-finger in Ran binding protein and others (5.7e−06); zf-RanBP: Zn-finger in Ran binding protein and others (6.4e−05); zf-RanBP: Zn-finger in Ran binding protein and others (0.034); GO_MF:GO:0008270, zinc ion binding# (0.0); GO_BP:GO:0006260, DNA replication# (2e−46); GO_CC:GO:0005622, intracellular# (0.0) | 5 | 42.2 | 11492146 | 11495948 |
| 73 | Autophagy-related protein 3 n = 3 Tax = *Oryza sativa* RepID = B9G6Z8_ORYSJ (3e−81); Autophagy_N: Autophagocytosis associated protein, N-terminal domain (4.3e−68); GO_BP:GO:0015031, protein transport# (3e−81); GO_CC:GO:0005737, cytoplasm# (3e−81) | 5 | 42.5 | 11726703 | 11728081 |
| 74 | Transposon protein n = 2 Tax = *Zea mays* RepID = B6SXI8_MAIZE (4e−42); Pkinase: Protein kinase domain (1.4e−06); GO_MF:GO:0005524, ATP binding# (2e−48); GO_BP:GO:0006468, protein amino acid phosphorylation# (2e−48); GO_CC:GO:0005886, plasma membrane# (4e−43) | 5 | 42.5 | 11722879 | 11723535 |

TABLE 9-continued

Candidate genes within TSS-5.01 interval

| Gene ID | Annotation | Chr | MON Map cM † | Physical Map Position bp ‡ Start | End |
|---|---|---|---|---|---|
| 75 | USP family protein n = 3 Tax = Andropogoneae RepID = B6TBM4_MAIZE (1e−52); GO_MF:GO:0016788, hydrolase activity, acting on ester bonds# (1e−09); GO_BP:GO:0006950, response to stress# (1e−52); GO_CC:GO:0005886, plasma membrane# (2e−27) | 5 | 42.6 | 7975907 | 7976458 |
| 76 | Nucleotide binding protein n = 2 Tax = Andropogoneae RepID = B6SKI8_MAIZE (0.0); WD40: WD domain, G-beta repeat (0.21); WD40: WD domain, G-beta repeat (0.33); WD40: WD domain, G-beta repeat (0.0024); WD40: WD domain, G-beta repeat (2.3e−07); WD40: WD domain, G-beta repeat (0.0038); WD40: WD domain, G-beta repeat (5.8e−06); WD40: WD domain, G-beta repeat (7.8e−11); GO_MF:GO:0016905, myosin heavy chain kinase activity# (1e−132); GO_BP:GO:0016905, myosin heavy chain kinase activity# (1e−132); GO_CC:GO:0005886, plasma membrane# (4e−57) | 5 | 42.7 | 7982533 | 7984518 |
| 77 | Protein fat-free homolog n = 1 Tax = *Dictyostelium discoideum* RepID = FFR_DICDI (1e−42); Vps51: Vps51/Vps67 (5.7e−27); COG5: Golgi transport complex subunit 5 (0.03); GO_MF:GO:0003674, ND#molecular_function# (2e−31); GO_BP:GO:0048193, Golgi vesicle transport# (3e−32); GO_CC:GO:0005794, IDA#Golgi apparatus# (3e−32) | 5 | 42.9 | 7996163 | 8010298 |
| 78 | Putative uncharacterized protein n = 1 Tax = *Zea mays* RepID = C0P437_MAIZE (2e−10) | 5 | 42.9 | 8000295 | 8000634 |
| 79 | Transposon protein, putative, CACTA, En/Spm sub-class n = 1 Tax = *Oryza sativa Japonica* Group RepID = Q2R337_ORYSJ (1e−29); GO_MF:GO:0005524, ATP binding# (2e−16); GO_BP:GO:0006468, protein amino acid phosphorylation# (2e−16) | 5 | 43.15 | 10308888 | 10309348 |
| 80 | Putative amino acid permease (Fragment) n = 1 Tax = *Phyllostachys edulis* RepID = D3IVC1_9POAL (2e−26); GO_MF:GO:0005488, binding# (4e−11); GO_CC:GO:0016021, integral to membrane# (6e−35) | 5 | 43.5 | 8064665 | 8066326 |
| 81 | Magnesium-dependent phosphatase, putative n = 1 Tax = *Ricinus communis* RepID = B9S9I9_RICCO (8e−72); GO_MF:GO:0016787, hydrolase activity# (8e−72); GO_BP:GO:0004725, protein tyrosine phosphatase activity# (8e−72) | 5 | 44.2 | 8134099 | 8137066 |
| 82 | K+-channel ERG and related proteins, contain PAS/PAC sensor domain (ISS) n = 1 Tax = *Ostreococcus tauri* RepID = Q00WW1_OSTTA (7e−12); GO_MF:GO:0008270, zinc ion binding# (0.0); GO_BP:GO:0050896, response to stimulus# (0.0); GO_CC:GO:0005737, cytoplasm# (0.0) | 5 | 44.65 | 8174598 | 8185641 |
| 83 | GRAM domain containing protein n = 2 Tax = Andropogoneae RepID = B4FWB9_MAIZE (9e−39) | 5 | 45 | 11755668 | 11756111 |
| 84 | Putative polyprotein n = 1 Tax = *Zea mays* RepID = Q8SA93_MAIZE (5e−49); GO_MF:GO:0003964, RNA-directed DNA polymerase, group II intron encoded# (5e−49); GO_BP:GO:0015074, DNA integration# (5e−49); GO_CC:GO:0005634, nucleus# (5e−49) | 5 | 45 | 11756148 | 11756699 |
| 85 | Autonomous transposable element EN-1 mosaic protein n = 1 Tax = *Zea mays* RepID = MOSA_MAIZE (1e−49); GO_BP:GO:0045449, regulation of transcription# (1e−49) | 5 | 45.2 | 11771200 | 11775727 |
| 86 | Heat shock protein binding protein, putative n = 1 Tax = *Ricinus communis* RepID = B9RIK9_RICCO (1e−11); GO_MF:GO:0051082, unfolded protein binding# (5e−17); GO_BP:GO:0006950, response to stress# (5e−17) | 5 | 45.2 | 11773940 | 11774350 |
| 87 | DELLA protein DWARF8 n = 6 Tax = Andropogoneae RepID = DWRF8_MAIZE (0.0); GRAS: GRAS family transcription factor (2.6e−201); GO_MF:GO:0005515, protein binding# (1e−147); GO_BP:GO:0045449, regulation of | 5 | 45.3 | 11782001 | 11784651 |

TABLE 9-continued

Candidate genes within TSS-5.01 interval

| Gene ID | Annotation | Chr | MON Map cM † | Physical Map Position bp ‡ Start | End |
|---|---|---|---|---|---|
| | transcription# (0.0); GO_CC:GO:0005634, nucleus# (0.0) | | | | |
| 88 | Putative uncharacterized protein n = 1 Tax = *Zea mays* RepID = B4FGE8_MAIZE (7e−12); GO_MF:GO:0004872, receptor activity# (5e−09); GO_BP:GO:0004872, receptor activity# (5e−09); GO_CC:GO:0016021, integral to membrane# (7e−12) | 5 | 45.3 | 11778209 | 11778515 |
| 89 | RING-HC protein 1 (Fragment) n = 1 Tax = *Oryza sativa Japonica* Group RepID = B4X9S6_ORYSJ (0.0); Tmemb_185A: Transmembrane Fragile-X-F protein (6.9e−145); GO_MF:GO:0046872, metal ion binding# (0.0) | 5 | 45.75 | 11818678 | 11827833 |
| 90 | Putative teosinte branched2 (Fragment) n = 1 Tax = *Zea mays* RepID = Q8SA84_MAIZE (1e−108); TCP: TCP family transcription factor (6.7e−58); GO_MF:GO:0003677, DNA binding# (3e−83); GO_BP:GO:0045449, regulation of transcription# (3e−83); GO_CC:GO:0005634, nucleus# (3e−83) | 5 | 45.95 | 11847079 | 11848514 |
| 91 | Putative uncharacterized protein Z195D10.15 n = 1 Tax = *Zea mays* RepID = Q8SA89_MAIZE (0.0) | 5 | 46.3 | 11881243 | 11883283 |
| 92 | Phosphatidylinositol-4-phosphate 5-kinase, putative n = 1 Tax = *Ricinus communis* RepID = B9RJA3_RICCO (0.0); MORN: MORN repeat (1.8e−06); MORN: MORN repeat (5.5e−08); MORN: MORN repeat (6.2e−06); MORN: MORN repeat (0.00011); MORN: MORN repeat (7.7e−08); MORN: MORN repeat (8.4e−08); MORN: MORN repeat (7e−07); PIP5K: Phosphatidylinositol-4-phosphate 5-Kinase (9.1e−138); GO_MF:GO:0016308, TAS#1-phosphatidylinositol-4-phosphate 5-kinase activity# (0.0); GO_BP:GO:0046488, phosphatidylinositol metabolic process# (0.0); GO_CC:GO:0005886, plasma membrane# (0.0) | 5 | 46.55 | 11904296 | 11908641 |
| 93 | Putative oxysterol binding protein n = 2 Tax = Poaceae RepID = Q8LN57_ORYSJ (0.0); PH: PH domain (6.5e−15); Oxysterol_BP: Oxysterol-binding protein (1.2e−66); GO_BP:GO:0008202, steroid metabolic process# (0.0) | 5 | 46.8 | 11925068 | 11945870 |
| 94 | Histone-lysine N-methyltransferase ASHR1 n = 3 Tax = Andropogoneae RepID = B6TKB7_MAIZE (0.0); SET: SET domain (0.026); zf-MYND: MYND finger (5.7e−08); GO_MF:GO:0046872, metal ion binding# (0.0); GO_BP:GO:0016568, chromatin modification# (1e−152); GO_CC:GO:0005634, nucleus# (1e−152) | 5 | 46.9 | 11949002 | 11954653 |
| 95 | Putative uncharacterized protein Sb01g047170 n = 1 Tax = *Sorghum bicolor* RepID = C5WXZ3_SORBI (3e−45); GO_MF:GO:0046872, metal ion binding# (2e−13); GO_BP:GO:0030001, metal ion transport# (2e−13) | 5 | 46.9 | 11962861 | 11963985 |
| 96 | Lysosomal pro-X carboxypeptidase, putative n = 1 Tax = *Ricinus communis* RepID = B9SX01_RICCO (3e−48); GO_MF:GO:0008236, serine-type peptidase activity# (1e−71); GO_BP:GO:0006508, proteolysis# (1e−71); GO_CC:GO:0005764, lysosome# (2e−30) | 5 | 46.95 | 11976263 | 11978269 |
| 97 | Glycyl-tRNA synthetase n = 1 Tax = *Zea mays* RepID = Q8SA98_MAIZE (3e−10); GO_MF:GO:0005524, ATP binding# (3e−10); GO_BP:GO:0006426, glycyl-tRNA aminoacylation# (3e−10); GO_CC:GO:0005737, cytoplasm# (3e−10) | 5 | 47 | 11983135 | 11985541 |
| 98 | Mitogen-activated protein kinase kinase kinase, putative n = 1 Tax = *Ricinus communis* RepID = B9RJB4_RICCO (1e−108); Pkinase: Protein kinase domain (1.3e−78); Pkinase_Tyr: Protein tyrosine kinase (9.9e−36); GO_MF:GO:0005524, ATP binding# (0.0); GO_BP:GO:0006468, protein amino acid phosphorylation# (0.0); GO_CC:GO:0005634, nucleus# (3e−94) | 5 | 47 | 12032678 | 12038402 |
| 99 | Ornithine carbamoyltransferase n = 4 Tax = Andropogoneae RepID = B6TYF3_MAIZE | 5 | 47 | 11979606 | 11980354 |

TABLE 9-continued

Candidate genes within TSS-5.01 interval

| Gene ID | Annotation | Chr | MON Map cM † | Physical Map Position bp ‡ Start | End |
|---|---|---|---|---|---|
|  | (5e-65); OTCace: Aspartate/ornithine carbamoyltransferase, Asp/Orn binding domain (1.3e-09); GO_MF:GO:0016743, carboxyl- or carbamoyltransferase activity# (5e-65); GO_BP:GO:0006520, cellular amino acid metabolic process# (5e-65); GO_CC:GO:0009348, ornithine carbamoyltransferase complex# (5e-65) |  |  |  |  |
| 100 | Clathrin heavy chain, putative; 28833-19741 n = 14 Tax = Magnoliophyta RepID = Q9SRM1_ARATH (1e-141); Clathrin: Region in Clathrin and VPS (1.1e-11); Clathrin: Region in Clathrin and VPS (1.6e-09); GO_MF:GO:0005515, protein binding# (1e-141); GO_BP:GO:0016192, vesicle-mediated transport# (1e-141); GO_CC:GO:0030132, clathrin coat of coated pit# (1e-141) | 5 | 47.1 | 12067722 | 12072775 |
| 101 | Eukaryotic peptide chain release factor subunit 1-3 n = 15 Tax = Spermatophyta RepID = ERF1Z_ARATH (0.0); eRF1_1: eRF1 domain 1 (2.8e-64); eRF1_2: eRF1 domain 2 (1e-64); eRF1_3: eRF1 domain 3 (7.1e-70); GO_MF:GO:0016149, translation release factor activity, codon specific# (0.0); GO_BP:GO:0016149, translation release factor activity, codon specific# (0.0); GO_CC:GO:0005737, cytoplasm# (0.0) | 5 | 47.2 | 12152026 | 12154962 |
| 102 | Putative uncharacterized protein Sb01g010850 n = 1 Tax = Sorghum bicolor RepID = C5WNT0_SORBI (1e-112) | 5 | 47.2 | 12151183 | 12151842 |
| 103 | Diacylglycerol Cholinephosphotransferase n = 1 Tax = Ricinus communis RepID = B9RLB3_RICCO (2e-36); CDP-OH_P_transf: CDP-alcohol phosphatidyltransferase (0.0044); GO_MF:GO:0016780, phosphotransferase activity, for other substituted phosphate groups# (3e-37); GO_BP:GO:0008654, phospholipid biosynthetic process# (3e-37); GO_CC:GO:0016020, membrane# (3e-37) | 5 | 47.25 | 12192134 | 12198757 |
| 104 | Ethylene receptor n = 4 Tax = Andropogoneae RepID = B5AID0_SACOF (0.0); GAF: GAF domain (1.6e-24); HisKA: His Kinase A (phosphoacceptor) domain (4.7e-23); HATPase_c: Histidine kinase-, DNA gyrase B-, and HSP90-like ATPase (4.4e-34); GO_MF:GO:0016772, transferase activity, transferring phosphorus-containing groups# (0.0); GO_BP:GO:0018106, peptidyl-histidine phosphorylation# (0.0); GO_CC:GO:0016020, membrane# (0.0) | 5 | 47.3 | 12219091 | 12224347 |
| 105 | Mitochondrial glycoprotein n = 1 Tax = Zea mays RepID = B6TJH8_MAIZE (5e-29); GO_CC:GO:0005759, IEP#mitochondrial matrix# (5e-29) | 5 | 47.3 | 12246610 | 12247706 |
| 106 | Os03g0701400 protein n = 4 Tax = Poaceae RepID = C7J050_ORYSJ (3e-14) | 5 | 47.3 | 12226203 | 12226667 |
| 107 | PBD: P21-Rho-binding domain (0.0036) | 5 | 47.3 | 12205194 | 12210281 |
| 108 | Pentatricopeptide repeat protein PPR868-14 n = 2 Tax = Andropogoneae RepID = B6U1A3_MAIZE (0.0); PPR: PPR repeat (0.42); TPR_4: Tetratricopeptide repeat (21); PPR: PPR repeat (3.2e-07); PPR: PPR repeat (3.4); TPR_4: Tetratricopeptide repeat (1.3); PPR: PPR repeat (0.072); TPR_4: Tetratricopeptide repeat (0.99); PPR: PPR repeat (8.2e-08); PPR: PPR repeat (0.48); PPR: PPR repeat (1.7e-08); PPR: PPR repeat (7.3); PPR: PPR repeat (2e-10); PPR: PPR repeat (0.0026); PPR: PPR repeat (1.9); PPR: PPR repeat (3.8); GO_MF:GO:0016787, hydrolase activity# (0.0) | 5 | 47.3 | 12227552 | 12230561 |
| 109 | Pinin/SDK/memA/ protein conserved region containing protein n = 2 Tax = Andropogoneae RepID = B6TZE8_MAIZE (1e-169); Pinin_SDK_memA: pinin/SDK/memA/ protein conserved reg (8.6e-07) | 5 | 47.3 | 12213021 | 12216524 |
| 110 | Transposon protein, putative, CACTA, En/Spm sub-class n = 1 Tax = Oryza sativa Japonica Group | 5 | 47.3 | 12230943 | 12240202 |

TABLE 9-continued

Candidate genes within TSS-5.01 interval

| Gene ID | Annotation | Chr | MON Map cM † | Physical Map Position bp ‡ Start | End |
|---|---|---|---|---|---|
| | RepID = Q2QVS8_ORYSJ (0.0); PRP4: pre-mRNA processing factor 4 (PRP4) li (2.2e−10); Prp18: Prp18 domain (5.2e−86); Transposase_21: Transposase family tnp2 (2.6e−125); GO_MF:GO:0008234, cysteine-type peptidase activity# (0.0); GO_BP:GO:0006508, proteolysis# (0.0); GO_CC:GO:0005634, nucleus# (0.0) | | | | |
| 111 | Ethylene insensitive 2 n = 2 Tax = Andropogoneae RepID = Q6JN48_MAIZE (1e−138); Nramp: Natural resistance-associated macrophage protein (1.1e−06); DUF846: Eukaryotic protein of unknown function (DUF846) (0.1); GO_MF:GO:0005215, transporter activity# (1e−156); GO_BP:GO:0006810, transport# (1e−156); GO_CC:GO:0016020, membrane# (1e−156) | 5 | 47.35 | 12267646 | 12272650 |
| 112 | Oleosin Zm-II n = 2 Tax = Zea mays RepID = OLEO3_MAIZE (2e−35); Oleosin: Oleosin (2e−56); GO_CC:GO:0016021, integral to membrane# (2e−35) | 5 | 47.35 | 12290664 | 12291897 |
| 113 | Putative uncharacterized protein n = 1 Tax = Zea mays RepID = B4FS85_MAIZE (7e−10) | 5 | 47.4 | 12293065 | 12293648 |
| 114 | Lipoxygenase n = 6 Tax = Andropogoneae RepID = C5WNU8_SORBI (0.0); Lipoxygenase: Lipoxygenase (0); GO_MF:GO:0046872, metal ion binding# (0.0); GO_BP:GO:0055114, oxidation reduction# (0.0); GO_CC:GO:0005737, cytoplasm# (0.0) | 5 | 47.5 | 12274159 | 12279086 |
| 115 | Pescadillo n = 3 Tax = Andropogoneae RepID = B6SHE5_MAIZE (2e−12); GO_BP:GO:0042254, ribosome biogenesis# (9e−13); GO_CC:GO:0005730, IDA#nucleolus# (9e−13) | 5 | 47.5 | 12287057 | 12289068 |
| 116 | Alkaline phytoceramidase, putative n = 1 Tax = Ricinus communis RepID = B9RXD0_RICCO (1e−109); aPHC: Alkaline phytoceramidase (aPHC) (1.6e−105); GO_MF:GO:0016787, hydrolase activity# (2e−25); GO_BP:GO:0071602, IDA#phytosphingosine biosynthetic process# (1e−24); GO_CC:GO:0005783, IDA#endoplasmic reticulum#(1e−106) | 5 | 47.8 | 12386676 | 12391874 |
| 117 | Putative glycerol 3-phosphate permease n = 1 Tax = Zea mays RepID = Q7FS87_MAIZE (4e−94); GO_MF:GO:0003964, RNA-directed DNA polymerase, group II intron encoded# (4e−94); GO_BP:GO:0055085, transmembrane transport# (4e−94); GO_CC:GO:0042719, mitochondrial intermembrane space protein transporter complex# (3e−31) | 5 | 47.8 | 12285238 | 12285897 |
| 118 | Zinc finger CCCH domain-containing protein 24 n = 4 Tax = Poaceae RepID = C3H24_ORYSJ (0.0); Ank: Ankyrin repeat (0.027); Ank: Ankyrin repeat (1.2e−07); zf-CCCH: Zinc finger C-x8-C-x5-C-x3-H type (and similar) (0.00014); GO_MF:GO:0046872, metal ion binding# (0.0); GO_BP:GO:0045449, regulation of transcription# (1e−159); GO_CC:GO:0005737, cytoplasm# (1e−129) | 5 | 47.8 | 12381419 | 12384900 |
| 119 | Cell division cycle protein cdt2 n = 2 Tax = Andropogoneae RepID = B6TYC2_MAIZE (0.0); WD40: WD domain, G-beta repeat (7.5); WD40: WD domain, G-beta repeat (3.4e−07); WD40: WD domain, G-beta repeat (7.7e−11); WD40: WD domain, G-beta repeat (4.4); WD40: WD domain, G-beta repeat (0.73); WD40: WD domain, G-beta repeat (0.68); WD40: WD domain, G-beta repeat (2.8e−07); GO_MF:GO:0005515, protein binding# (1e−54); GO_BP:GO:0051301, cell division# (0.0); GO_CC:GO:0031965, nuclear membrane# (1e−54) | 5 | 48 | 12397184 | 12400838 |
| 120 | Putative uncharacterized protein n = 1 Tax = Zea mays RepID = D1ME33_MAIZE (3e−10) | 5 | 48 | 12546422 | 12548059 |
| 121 | LvsC-like n = 1 Tax = Oryza sativa Japonica Group RepID = Q655H8_ORYSJ (7e−26); Beach: Beige/BEACH domain (1.8e−06); GO_MF:GO:0005488, binding# (4e−24); | 5 | 48.15 | 12554684 | 12555416 |

TABLE 9-continued

Candidate genes within TSS-5.01 interval

| Gene ID | Annotation | Chr | MON Map cM † | Physical Map Position bp ‡ Start | End |
|---|---|---|---|---|---|
| | GO_BP:GO:0008150, ND#biological_process# (2e–16); GO_CC:GO:0005739, mitochondrion# (5e–23) | | | | |
| 122 | Putative ABC transporter n = 1 Tax = *Oryza sativa Japonica* Group RepID = Q851S1_ORYSJ (1e–123); GO_MF:GO:0016740, transferase activity# (2e–38); GO_BP:GO:0016301, kinase activity# (2e–38); GO_CC:GO:0005576, extracellular region# (2e–38) | 5 | 48.2 | 12528795 | 12531980 |
| 123 | Putative ABC transporter n = 1 Tax = *Oryza sativa Japonica* Group RepID = Q851S1_ORYSJ (7e–50) | 5 | 48.2 | 12524473 | 12525802 |
| 124 | Putative uncharacterized protein Sb01g011180 n = 1 Tax = *Sorghum bicolor* RepID = C5WNW3_SORBI (7e–28); zf-C2H2: Zinc finger, C2H2 type (0.044); zf-C2H2: Zinc finger, C2H2 type (0.55) | 5 | 48.2 | 12533769 | 12535195 |
| 125 | Chloroplast heat shock protein 70 n = 2 Tax = Poaceae RepID = A4ZYQ0_PENAM (0.0); MreB_Mbl: MreB/Mbl protein (7.8e–07); HSP70: Hsp70 protein (0); GO_MF:GO:0051082, unfolded protein binding# (0.0); GO_BP:GO:0006950, response to stress# (0.0); GO_CC:GO:0009570, IDA#chloroplast stroma# (0.0) | 5 | 48.3 | 12580120 | 12585761 |
| 126 | Proteasome subunit beta type n = 5 Tax = Andropogoneae RepID = C5WNX2_SORBI (1e–111); Proteasome: Proteasome A-type and B-type (4.5e–51); GO_MF:GO:0016787, hydrolase activity# (1e–104); GO_BP:GO:0051603, proteolysis involved in cellular protein catabolic process# (1e–104); GO_CC:GO:0005839, proteasome core complex# (1e–104) | 5 | 48.3 | 12565088 | 12568390 |
| 127 | Putative uncharacterized protein n = 1 Tax = *Zea mays* RepID = B4FZ37_MAIZE (1e–86); DUF1517: Protein of unknown function (DUF1517) (1.1e–17) | 5 | 48.3 | 12569937 | 12576194 |
| 128 | Putative uncharacterized protein n = 3 Tax = *Zea mays* RepID = B6TA41_MAIZE (4e–73); Hin1: Harpin-induced protein 1 (Hin1) (2.6e–05); GO_MF:GO:0005524, ATP binding# (4e–13); GO_BP:GO:0006468, protein amino acid phosphorylation# (4e–13) | 5 | 48.3 | 12558697 | 12562009 |
| 129 | OSIGBa0114M03.4 protein n = 1 Tax = *Oryza sativa* RepID = Q01M69_ORYSA (5e–50); GO_MF:GO:0003964, RNA-directed DNA polymerase, group II intron encoded# (3e–51); GO_BP:GO:0015074, DNA integration# (3e–51); GO_CC:GO:0005634, nucleus# (3e–51) | 5 | 48.4 | 12683304 | 12685155 |
| 130 | OSJNBa0027G07.10 protein n = 1 Tax = *Oryza sativa Japonica* Group RepID = Q7XMY6_ORYSJ (5e–32); hATC: hAT family dimerisation domain (3.9e–29); GO_MF:GO:0046983, protein dimerization activity# (5e–32) | 5 | 48.4 | 13171495 | 13172245 |
| 131 | Putative centromere protein n = 1 Tax = *Solanum lycopersicum* RepID = Q949K0_SOLLC (4e–56) | 5 | 48.4 | 13143462 | 13165411 |
| 132 | Putative uncharacterized protein n = 1 Tax = *Zea mays* RepID = B4FJ43_MAIZE (1e–28) | 5 | 48.4 | 13137932 | 13139095 |
| 133 | Putative uncharacterized protein Sb01g011340 n = 4 Tax = Andropogoneae RepID = C5WNY1_SORBI (3e–28); GO_MF:GO:0003735, structural constituent of ribosome# (1e–23); GO_BP:GO:0006412, translation# (1e–23); GO_CC:GO:0005840, ribosome# (1e–23) | 5 | 48.4 | 12645162 | 12648452 |
| 134 | Putative uncharacterized protein Sb01g011510 n = 1 Tax = *Sorghum bicolor* RepID = C5WPH9_SORBI (1e–110) | 5 | 48.4 | 13142037 | 13143429 |
| 135 | Mitogen-activated protein kinase kinase 3 n = 3 Tax = *Oryza sativa* RepID = A3FK65_ORYSI (0.0); Pkinase_Tyr: Protein tyrosine kinase (2.9e–10); Pkinase: Protein kinase domain (1.9e–27); GO_MF:GO:0005524, ATP binding# (0.0); GO_BP:GO:0006468, protein amino acid phosphorylation# (0.0); GO_CC:GO:0005622, intracellular# (1e–75) | 5 | 48.45 | 12680045 | 12706814 |

TABLE 9-continued

Candidate genes within TSS-5.01 interval

| Gene ID | Annotation | Chr | MON Map cM † | Physical Map Position bp ‡ Start | End |
|---|---|---|---|---|---|
| 136 | Phosphoglucomutase, putative n = 1 Tax = *Ricinus communis* RepID = B9T3D2_RICCO (2e−24); GO_MF:GO:0016868, intramolecular transferase activity, phosphotransferases# (2e−33); GO_BP:GO:0005975, carbohydrate metabolic process# (2e−33); GO_CC:GO:0009507, chloroplast# (7e−23) | 5 | 48.5 | 12734486 | 12734788 |
| 137 | Phosphoglucomutase, putative n = 1 Tax = *Ricinus communis* RepID = B9T3D2_RICCO (4e−23); GO_MF:GO:0016868, intramolecular transferase activity, phosphotransferases# (1e−32); GO_BP:GO:0005975, carbohydrate metabolic process# (1e−32); GO_CC:GO:0009507, chloroplast# (1e−21) | 5 | 48.5 | 12742666 | 12743577 |
| 138 | Protein yippee-like n = 3 Tax = Andropogoneae RepID = B6T8M4_MAIZE (4e−66); Yippee: Yippee putative zinc-binding protein (1.1e−73) | 5 | 48.5 | 12364285 | 12366594 |
| 139 | Putative auxin-regulated protein n = 1 Tax = *Oryza sativa Japonica* Group RepID = Q6YYY6_ORYSJ (9e−37); DUF966: Domain of unknown function (DUF966) (1.4e−163); GO_CC:GO:0005886, plasma membrane# (9e−33) | 5 | 48.5 | 13074678 | 13076704 |
| 140 | Putative uncharacterized protein n = 1 Tax = *Zea mays* RepID = B4FG98_MAIZE (1e−131); GO_MF:GO:0005515, protein binding# (5e−51); GO_BP:GO:0031047, IMP#gene silencing by RNA# (5e−51) | 5 | 48.6 | 12832672 | 12834763 |
| 141 | DEAD box ATP-dependent RNA helicase, putative n = 2 Tax = *Perkinsus marinus* ATCC 50983 RepID = C5LQP0_9ALVE (1e−09); DUF1336: Protein of unknown function (DUF1336) (1.1e−137); GO_MF:GO:0016787, hydrolase activity# (1e−09); GO_CC:GO:0005886, plasma membrane# (1e−136) | 5 | 48.7 | 12920656 | 12927459 |
| 142 | Putative uncharacterized protein Sb01g011440 n = 6 Tax = Andropogoneae RepID = C5WPH2_SORBI (4e−73); DUF538: Protein of unknown function, DUF538 (6.2e−53); GO_MF:GO:0043565, sequence-specific DNA binding# (5e−18); GO_BP:GO:0045449, regulation of transcription# (5e−18); GO_CC:GO:0005773, IDA#vacuole# (2e−28) | 5 | 48.7 | 13047985 | 13051250 |
| 143 | Transposon protein, putative, Mutator sub-class n = 2 Tax = *Oryza sativa Japonica* Group RepID = Q10K32_ORYSJ (7e−31); MuDR: MuDR family transposase (0.0015); GO_MF:GO:0008270, zinc ion binding# (7e−31) | 5 | 48.7 | 12922760 | 12923541 |
| 144 | ComA operon protein (Competence protein) n = 1 Tax = *Syntrophomonas wolfei* subsp. *wolfei* str. Goettingen RepID = Q0AWL3_SYNWW (4e−16); 4HBT: Thioesterase superfamily (1.5e−18); GO_MF:GO:0016787, hydrolase activity# (8e−57); GO_CC:GO:0005777, IDA#peroxisome# (1e−51) | 5 | 48.75 | 13179000 | 13182566 |
| 145 | ER degradation-enhancing alpha-mannosidase-like 1 n = 1 Tax = *Zea mays* RepID = B6SH10_MAIZE (7e−51); Glyco_hydro_47: Glycosyl hydrolase family 47 (0.056); GO_MF:GO:0005509, calcium ion storage activity# (7e−51); GO_BP:GO:0008152, metabolic process# (1e−41); GO_CC:GO:0016020, membrane# (7e−51) | 5 | 48.8 | 12982953 | 12984914 |
| 146 | Transposon protein, putative, CACTA, En/Spm sub-class n = 2 Tax = *Oryza sativa Japonica* Group RepID = Q10FD4_ORYSJ (1e−42); DUF1336: Protein of unknown function (DUF1336) (4.6e−53); GO_MF:GO:0004803, transposase activity# (3e−43); GO_BP:GO:0006313, transposition, DNA-mediated# (3e−43); GO_CC:GO:0005886, plasma membrane# (3e−55) | 5 | 48.8 | 13042088 | 13045337 |
| 147 | Transposon protein, putative, CACTA, En/Spm sub-class n = 2 Tax = *Oryza sativa Japonica* Group RepID = Q10FD4_ORYSJ (3e−48); | 5 | 48.8 | 13038588 | 13043359 |

TABLE 9-continued

Candidate genes within TSS-5.01 interval

| Gene ID | Annotation | Chr | MON Map cM † | Physical Map Position bp ‡ Start | End |
|---|---|---|---|---|---|
| | GO_MF:GO:0003735, structural constituent of ribosome# (0.0); GO_BP:GO:0006412, translation# (0.0); GO_CC:GO:0005840, ribosome# (0.0) | | | | |
| 148 | Calcium-dependent protein kinase 1 n = 1 Tax = *Datura metel* RepID = A9Z0P8_DATME (0.0); APH: Phosphotransferase enzyme family (0.069); Kdo: Lipopolysaccharide kinase (Kdo) (0.01); Pkinase: Protein kinase domain (5.6e−103); Pkinase_Tyr: Protein tyrosine kinase (7.6e−11); efhand: EF hand (7.6e−08); efhand: EF hand (0.00021); efhand: EF hand (9.1e−05); efhand: EF hand (1.1e−08); GO_MF:GO:0016740, transferase activity# (0.0); GO_BP:GO:0016301, kinase activity# (0.0); GO_CC:GO:0016020, membrane# (0.0) | 5 | 48.9 | 13273415 | 13276346 |
| 149 | ELL-associated factor, putative n = 1 Tax = *Ricinus communis* RepID = B9SYJ2_RICCO (1e−57); EAF: ELL-associated factor (5.3e−63) | 5 | 48.9 | 13187272 | 13193188 |
| 150 | Isoamylase N-terminal domain containing protein n = 2 Tax = *Oryza sativa Japonica* Group RepID = Q6AVV5_ORYSJ (2e−59) | 5 | 48.9 | 13308841 | 13314483 |
| 151 | Metal ion transporter-like protein n = 1 Tax = *Hordeum vulgare* RepID = B4YHA7_HORVU (5e−30); GO_MF:GO:0046873, metal ion transmembrane transporter activity# (4e−33); GO_BP:GO:0055085, transmembrane transport# (4e−33); GO_CC:GO:0016021, integral to membrane# (4e−33) | 5 | 48.9 | 13246516 | 13250631 |
| 152 | Nitrate transporter, putative n = 3 Tax = Poaceae RepID = Q6AVV6_ORYSJ (0.0); MFS_1: Major Facilitator Superfamily (0.0095); PTR2: POT family (7.7e−80); GO_MF:GO:0005215, transporter activity# (0.0); GO_BP:GO:0006857, oligopeptide transport# (0.0); GO_CC:GO:0016020, membrane# (0.0) | 5 | 48.9 | 13303170 | 13308605 |
| 153 | OSJNBa0033G16.15 protein n = 3 Tax = *Oryza sativa* RepID = Q7X6C3_ORYSJ (1e−75); GO_CC:GO:0005739, mitochondrion# (7e−47) | 5 | 48.9 | 13253146 | 13257717 |
| 154 | Putative uncharacterized protein Sb01g011420 n = 1 Tax = *Sorghum bicolor* RepID = C5WPH0_SORBI (1e−45); DUF1336: Protein of unknown function (DUF1336) (1.3e−05); GO_CC:GO:0005886, plasma membrane# (8e−39) | 5 | 48.9 | 13011015 | 13011555 |
| 155 | Putative uncharacterized protein Sb01g011640 n = 3 Tax = Andropogoneae RepID = C5WPJ3_SORBI (1e−120); GRP: Glycine rich protein family (0.091) | 5 | 48.9 | 13280268 | 13284527 |
| 156 | Glycosyl transferase family 8 protein-like n = 2 Tax = *Oryza sativa* RepID = Q652K2_ORYSJ (0.0); Glyco_transf_8: Glycosyl transferase family 8 (2.7e−117); GO_MF:GO:0016757, transferase activity, transferring glycosyl groups# (0.0); GO_BP:GO:0006468, protein amino acid phosphorylation# (0.0); GO_CC:GO:0005886, plasma membrane# (0.0) | 5 | 49 | 13227422 | 13232004 |
| 157 | Defense-related protein n = 1 Tax = *Zea mays* RepID = B6TR53_MAIZE (1e−142); Peptidase_C26: Peptidase C26 (0.00016); GATase: Glutamine amidotransferase class-I (7.2e−05); GO_MF:GO:0003824, catalytic activity# (1e−142); GO_BP:GO:0006541, glutamine metabolic process# (1e−114); GO_CC:GO:0005737, cytoplasm# (8e−53) | 5 | 49.05 | 13396126 | 13399562 |
| 158 | HPP n = 1 Tax = *Zea mays* RepID = B6TMS3_MAIZE (1e−124); HPP: HPP family (1.2e−53); GO_CC:GO:0009941, IDA#chloroplast envelope# (7e−54) | 5 | 49.5 | 13503339 | 13506716 |
| 159 | Putative ubiquitin protein ligase n = 1 Tax = *Oryza sativa* RepID = Q9AUK0_ORYSA (0.0); HECT: HECT-domain (ubiquitin-transferase) (7.5e−143); GO_MF:GO:0016881, acid-amino acid ligase activity# (0.0); GO_BP:GO:0006464, protein modification process# (0.0); GO_CC:GO:0005622, intracellular# (0.0) | 5 | 49.5 | 13579060 | 13592029 |

TABLE 9-continued

Candidate genes within TSS-5.01 interval

| Gene ID | Annotation | Chr | MON Map cM † | Physical Map Position bp ‡ Start | End |
|---|---|---|---|---|---|
| 160 | Putative uncharacterized protein n = 1 Tax = *Zea mays* RepID = B6SUB9_MAIZE (1e−62) | 5 | 49.5 | 13557223 | 13557751 |
| 161 | Serine/threonine-protein phosphatase n = 1 Tax = *Zea mays* RepID = C4J6S0_MAIZE (2e−29); DnaJ: DnaJ domain (0.052); GO_MF:GO:0016787, hydrolase activity# (1e−29); GO_BP:GO:0004721, phosphoprotein phosphatase activity# (4e−25); GO_CC:GO:0005737, cytoplasm# (7e−22) | 5 | 49.5 | 13584096 | 13587179 |
| 162 | Smr domain containing protein n = 2 Tax = Andropogoneae RepID = B6SWQ7_MAIZE (7e−73); DUF1771: Domain of unknown function (DUF1771) (3.6e−09); Smr: Smr domain (2.4e−08); GO_MF:GO:0005515, protein binding# (7e−54); GO_BP:GO:0055114, oxidation reduction# (1e−11); GO_CC:GO:0005737, cytoplasm# (2e−11) | 5 | 49.5 | 13571302 | 13572951 |
| 163 | Ulp1 protease family, C-terminal catalytic domain containing protein n = 2 Tax = *Oryza sativa Japonica* Group RepID = Q109R5_ORYSJ (2e−15); GO_MF:GO:0008234, cysteine-type peptidase activity# (2e−15); GO_BP:GO:0006508, proteolysis# (2e−15) | 5 | 49.5 | 13567734 | 13569041 |
| 164 | Ulp1 protease family, C-terminal catalytic domain containing protein n = 2 Tax = *Oryza sativa Japonica* Group RepID = Q109R5_ORYSJ (2e−30); Peptidase_C48: Ulp1 protease family, C-terminal catalytic domain (8.8e−07); GO_MF:GO:0008234, cysteine-type peptidase activity# (1e−133); GO_BP:GO:0006508, proteolysis# (1e−133) | 5 | 49.5 | 13565952 | 13567333 |
| 165 | Protein argonaute 12 n = 1 Tax = *Oryza sativa Japonica* Group RepID = AGO12_ORYSJ (0.0); DUF1785: Domain of unknown function (DUF1785) (5.2e−29); PAZ: PAZ domain (2.4e−42); Piwi: Piwi domain (9.1e−141); GO_MF:GO:0003676, nucleic acid binding# (0.0); GO_BP:GO:0031047, IMP#gene silencing by RNA# (0.0); GO_CC:GO:0005737, cytoplasm# (0.0) | 5 | 49.55 | 13600503 | 13607401 |
| 166 | Ferredoxin-6 n = 2 Tax = *Zea mays* RepID = B6SU48_MAIZE (6e−41); GO_MF:GO:0051536, iron-sulfur cluster binding# (6e−41); GO_BP:GO:0022900, electron transport chain# (4e−18) | 5 | 49.6 | 13427619 | 13428506 |
| 167 | Ferredoxin-6 n = 2 Tax = *Zea mays* RepID = B6SU48_MAIZE (7e−34); Fer2: 2Fe—2S iron-sulfur cluster binding do (0.017); GO_MF:GO:0051536, iron-sulfur cluster binding# (2e−34); GO_BP:GO:0015074, DNA integration# (2e−34) | 5 | 49.6 | 13410180 | 13419773 |
| 168 | Glycine-rich RNA-binding protein, putative n = 1 Tax = *Ricinus communis* RepID = B9T555_RICCO (6e−31); RRM_1: RNA recognition motif, (a.k.a. RRM, RB (2.1e−24); zf-CCHC: Zinc knuckle (8.1e−07); GO_MF:GO:0008270, zinc ion binding# (8e−77); GO_BP:GO:0009631, IEP#cold acclimation# (2e−23); GO_CC:GO:0005730, IDA#nucleolus# (4e−28) | 5 | 49.6 | 13608604 | 13613429 |
| 169 | SpoU rRNA Methylase family protein n = 3 Tax = Andropogoneae RepID = B6TZF3_MAIZE (2e−10); GO_MF:GO:0008173, RNA methyltransferase activity# (2e−10); GO_BP:GO:0006396, RNA processing# (2e−10) | 5 | 49.6 | 13409304 | 13409905 |
| 170 | SpoU rRNA Methylase family protein n = 3 Tax = Andropogoneae RepID = B6TZF3_MAIZE (7e−75); SpoU_methylase: SpoU rRNA Methylase family (6.7e−24); GO_MF:GO:0008173, RNA methyltransferase activity# (7e−75); GO_BP:GO:0006396, RNA processing# (7e−75) | 5 | 49.6 | 13407708 | 13409045 |
| 171 | BEL1-related homeotic protein 30 n = 2 Tax = Andropogoneae RepID = B6SWM4_MAIZE (0.0); POX: Associated with HOX (3.4e−74); Homeobox: Homeobox domain (0.0071); GO_MF:GO:0043565, sequence-specific DNA | 5 | 49.7 | 13660180 | 13666305 |

TABLE 9-continued

Candidate genes within TSS-5.01 interval

| Gene | | MON | | Physical Map Position bp ‡ | |
|---|---|---|---|---|---|
| ID | Annotation | Chr | Map cM † | Start | End |
| | binding# (0.0); GO__BP:GO:0045449, regulation of transcription# (0.0); GO__CC:GO:0005634, nucleus# (0.0) | | | | |
| 172 | Ubiquitin-conjugating enzyme E2 W n = 1 Tax = Zea mays RepID = B6T455_MAIZE (5e-53); UQ_con: Ubiquitin-conjugating enzyme (7e-41); GO_MF:GO:0019787, small conjugating protein ligase activity# (8e-52); GO__BP:GO:0051246, regulation of protein metabolic process# (8e-52) | 5 | 49.7 | 13646747 | 13649777 |

† cM = centiMorgans.
†† bp = base pair of Arizona Genomics Institute B73 RefGen_v2 sequence.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents. All patent and non-patent documents cited in this specification are incorporated herein by reference in their entireties.

What is claimed is:

1. A method of obtaining a corn plant with reduced tassel skeletonization severity, comprising:

a) providing a population of corn plants;

b) obtaining at least one nucleic acid sample from at least one plant within said population;

c) detecting in the nucleic acid sample the presence of a reduced tassel skeletonization allele comprising SEQ ID NO: 27, wherein N at nucleotide position 162 is a nucleotide that is associated with the presence of the reduced tassel skeletonization severity trait;

d) selecting a corn plant from said population of corn plants based on the presence of the reduced tassel skeletonization allele in the nucleic acid sample; and e) crossing the corn plant comprising the reduced tassel skeletonization allele with a second corn plant to produce progeny plants, wherein at least one progeny plant comprises the reduced tassel skeletonization allele and exhibits reduced tassel skeletonization severity when compared to a plant lacking said allele.

2. The method of claim 1, wherein step (a) of providing comprises crossing a first corn plant comprising a reduced tassel skeletonization allele with a second corn plant to produce a population of corn plants.

3. The method of claim 2, wherein producing the population of corn plants comprises backcrossing.

4. The method of claim 1, wherein step (c) of detecting comprises the use of an oligonucleotide probe.

5. A method of producing a corn plant with reduced tassel skeletonization severity, comprising:
a) crossing a first corn plant comprising a reduced tassel skeletonization allele with a second corn plant of a different genotype to produce one or more progeny plants; and
b) using marker-assisted selection to select a progeny plant based on the presence of said allele, wherein said allele comprises SEQ ID NO: 27, wherein N at nucleotide position 162 is a nucleotide that is associated with the presence of the reduced tassel skeletonization severity trait;
wherein said allele confers reduced tassel skeletonization severity compared to a plant lacking said allele.

6. The method of claim 5, further comprising:
c) crossing said progeny plant with itself or a second plant to produce one or more further progeny plants; and
d) selecting a further progeny plant comprising said allele.

7. The method of claim 6, wherein step (d) of selecting comprises marker-assisted selection.

8. The method of claim 7, wherein said marker-assisted selection comprises selecting a progeny plant based on the presence of a reduced tassel skeletonization allele, wherein said allele comprises SEQ ID NO: 27 and wherein N at nucleotide position 162 is a nucleotide that is associated with the presence of the reduced tassel skeletonization severity trait.

9. The method of claim 6, wherein said further progeny plant is an F2-F7 progeny plant.

10. The method of claim 9, wherein producing the progeny plant comprises backcrossing.

11. The method of claim 10, wherein backcrossing comprises from 2-7 generations of backcrosses.

12. The method of claim 10, wherein backcrossing comprises marker-assisted selection.

13. The method of claim 12, wherein backcrossing comprises marker-assisted selection in at least two generations.

14. The method of claim 13, wherein backcrossing comprises marker-assisted selection in all generations.

15. The method of claim 12, wherein marker-assisted selection comprises selecting a progeny plant based on the presence of a reduced tassel skeletonization allele, wherein said allele comprises SEQ ID NO: 27 and wherein N at nucleotide position 162 is a nucleotide that is associated with the presence of the reduced tassel skeletonization severity trait.

16. The method of claim 5, wherein said first corn plant is an inbred or a hybrid.

17. The method of claim 5, wherein said second corn plant is an agronomically elite corn plant.

18. The method of claim 17, wherein said agronomically elite corn plant is an inbred or a hybrid.

19. A method of obtaining a corn plant with reduced tassel skeletonization severity, comprising:
a) providing a population of corn plants;
b) obtaining at least one nucleic acid sample from at least one plant within said population;
c) detecting in the nucleic acid sample the presence of a reduced tassel skeletonization allele, wherein said reduced tassel skeletonization allele comprises at least one of SEQ ID NOs: 1 or 13, wherein N at nucleotide position 453 of SEQ ID NO: 1 or N at nucleotide position 316 of SEQ ID NO: 13 is a nucleotide that is associated with the presence of the reduced tassel skeletonization severity trait;
d) selecting a corn plant from said population of corn plants based on the presence of the reduced tassel skeletonization allele in the nucleic acid sample;
e) crossing the corn plant comprising the reduced tassel skeletonization allele with a second corn plant to produce progeny plants, wherein at least one progeny plant comprises the reduced tassel skeletonization allele and exhibits reduced tassel skeletonization severity when compared to a plant lacking said allele; and
f) phenotypically selecting said at least one progeny plant based on the reduced tassel skeletonization severity trait.

20. The method of claim 19, wherein step (a) of providing comprises crossing a first corn plant comprising a reduced tassel skeletonization allele with a second corn plant to produce a population of corn plants.

21. The method of claim 20, wherein producing the population of corn plants comprises backcrossing.

22. The method of claim 19, wherein step (c) of detecting comprises the use of an oligonucleotide probe.

23. A method of producing a corn plant with reduced tassel skeletonization severity, comprising:
a) crossing a first corn plant with a genotypically different second corn plant to produce one or more progeny plants, wherein the first corn plant phenotypically exhibits the trait of reduced tassel skeletonization severity compared to the second corn plant, and wherein said first corn plant comprises at least one reduced tassel skeletonization severity allele conferring said reduced tassel skeletonization severity; and
b) using marker-assisted selection to select a progeny plant based on the presence of said allele, wherein said allele comprises at least one of SEQ ID NOs: 1 or 13, wherein N at nucleotide position 453 of SEQ ID NO: 1 or N at nucleotide position 316 of SEQ ID NO: 13 is a nucleotide that is associated with the presence of the reduced tassel skeletonization severity trait.

24. The method of claim 23, further comprising:
c) crossing said progeny plant with itself or a second plant to produce one or more further progeny plants; and
d) selecting a further progeny plant comprising said allele.

25. The method of claim 24, wherein step (d) of selecting comprises marker-assisted selection.

26. The method of claim 25, wherein said marker-assisted selection comprises selecting a progeny plant based on the presence of at least one reduced tassel skeletonization allele, wherein said allele comprises at least one of SEQ ID NOs: 1 or 13, wherein N at nucleotide position 453 of SEQ ID NO: 1 or N at nucleotide position 316 of SEQ ID NO: 13 is a nucleotide that is associated with the presence of the reduced tassel skeletonization severity trait.

27. The method of claim 24, wherein said further progeny plant is an F2-F7 progeny plant.

28. The method of claim 27, wherein producing the progeny plant comprises backcrossing.

29. The method of claim 28, wherein backcrossing comprises from 2-7 generations of backcrosses.

30. The method of claim 28, wherein backcrossing comprises marker-assisted selection.

31. The method of claim 30, wherein backcrossing comprises marker-assisted selection in at least two generations.

32. The method of claim 31, wherein backcrossing comprises marker-assisted selection in all generations.

33. The method of claim 30, wherein marker-assisted selection comprises selecting a progeny plant based on the presence of at least one reduced tassel skeletonization allele, wherein said allele comprises at least one of SEQ ID NOs: 1 or 13, wherein N at nucleotide position 453 of SEQ ID NO: 1 or N at nucleotide position 316 of SEQ ID NO: 13 is a nucleotide that is associated with the presence of the reduced tassel skeletonization severity trait.

34. The method of claim 23, wherein said first corn plant is an inbred or a hybrid.

35. The method of claim 23, wherein said second corn plant is an agronomically elite corn plant.

36. The method of claim 35, wherein said agronomically elite corn plant is an inbred or a hybrid.

\* \* \* \* \*